US011555072B2

(12) United States Patent
Wu et al.

(10) Patent No.: US 11,555,072 B2
(45) Date of Patent: Jan. 17, 2023

(54) A33 ANTIBODY COMPOSITIONS AND METHODS OF USING THE SAME IN RADIOIMMUNOTHERAPY

(71) Applicant: MEMORIAL SLOAN KETTERING CANCER CENTER, New York, NY (US)

(72) Inventors: Zhihao Wu, New York, NY (US); Hong Xu, New York, NY (US); Nai-Kong Cheung, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 128 days.

(21) Appl. No.: 16/649,617

(22) PCT Filed: Sep. 21, 2018

(86) PCT No.: PCT/US2018/052253
§ 371 (c)(1),
(2) Date: Mar. 20, 2020

(87) PCT Pub. No.: WO2019/060750
PCT Pub. Date: Mar. 28, 2019

(65) Prior Publication Data
US 2020/0291112 A1 Sep. 17, 2020

Related U.S. Application Data

(60) Provisional application No. 62/562,374, filed on Sep. 23, 2017, provisional application No. 62/562,373, filed on Sep. 23, 2017.

(51) Int. Cl.
*A61P 35/00* (2006.01)
*C07K 16/28* (2006.01)
*A61K 39/00* (2006.01)

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/622* (2013.01); *C07K 2317/73* (2013.01); *C07K 2317/92* (2013.01)

(58) Field of Classification Search
CPC .......... C07K 2317/24; C07K 2317/565; A61P 35/00; A61K 2039/505
USPC .......................................... 424/133.1, 135.1
See application file for complete search history.

(56) References Cited

U.S. PATENT DOCUMENTS 6,307,026 B1  10/2001  King et al.
2002/0062009 A1   5/2002  Taylor

FOREIGN PATENT DOCUMENTS

WO   WO-98/52976 A1    11/1998
WO   WO-2016/054005 A1  4/2016
WO   WO-2016/130539 A2  8/2016
WO   WO-2016/164308 A1  10/2016

OTHER PUBLICATIONS

Wu et al (Mol. Cancer Ther Oct. 2018;17(10):2164-2175; Epub Aug. 6, 2018).*
Almagro & Franssen, Frontiers in Bioscience, 13:1619-33 (2008).*
Edwards et al., J Mol Biol 334:103-118 (2003).*
Marchalonis et al., Dev & Comp Immunol. 30:223-247 (2006).*
Lippow et al., "Computational design of antibody-affinity improvement beyond in vivo maturation," Nature Biotechnology, 25(10):1171-1176 (2007).*
Sulea et al., "Application of Assisted Design of Antibody and Protein Therapeutics (ADAPT) improves efficacy of a Clostridium difficile toxin A single-domain antibody," Scientific Reports, 8(260):1-11 (2018).*
Hasegawa et al., "Single amino acid substitution in LC-CDR1 induces Russell body phenotype that attenuates cellular protein synthesis through eIF2a phosphorylation and thereby downregulates IgG secretion despite operational secretory pathway traffic," MABS, vol. 9, No. 5, pp. 854-873 (2017).*
Altshuler et al., "Generation of Recombinant Antibodies and Means for Increasing Their Affinity," Biochemistry (Moscow), 75(13):1584-1605 (2010) at p. 1600, col. 1, para. 2, lines 1-5.*
Vajda et al., "Progress toward improved understanding of antibody maturation," Current Opinion in Structural Biology, 67 pp. 226-231 (2021).*
Marks et al., "How repertoire data are changing antibody science," J. Biol. Chem. 295(29) 9823-9837 (2020).*
Akbar et al., Cell Reports 34, 108856, Mar. 16, 2021.*
Lo et al., "Conformational epitope matching and prediction based on protein surface spiral features," BMC Genomics vol. 22, Article No. 116 (2021).*
International Search Report and Written Opinion, PCT/US2018/052253, Memorial Sloan Kettering Cancer Center (dated Apr. 8, 2019).
King et al., "Preparation and Preclinical Evaluation of Humanised A33 Immunoconjugates for Radioimmunology," British Journal of Cancer, vol. 72, No. 6, pp. 1364-1372 (Dec. 1, 1995).

* cited by examiner

*Primary Examiner* — Lynn A Bristol
(74) *Attorney, Agent, or Firm* — Foley & Lardner LLP

(57) ABSTRACT

The present disclosure relates generally to immunoglobulin-related compositions such as antibodies or antigen binding fragments thereof that can bind to and neutralize the activity of A33 protein. The antibodies of the present technology are useful in methods for detecting and treating an A33-positive cancer in a subject in need thereof.

21 Claims, 47 Drawing Sheets

Specification includes a Sequence Listing.

Figure 1
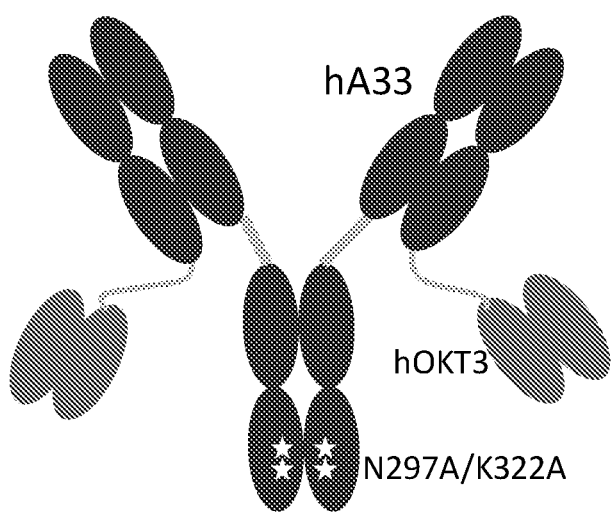
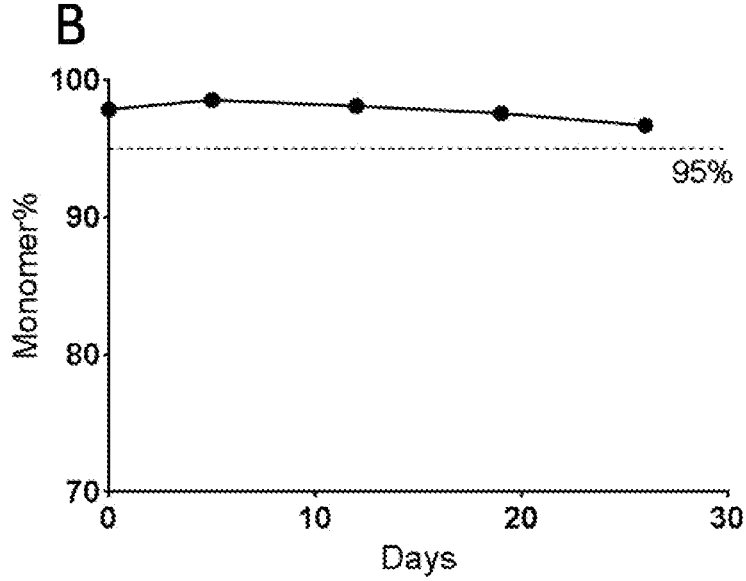

Figure 1 (contd.)
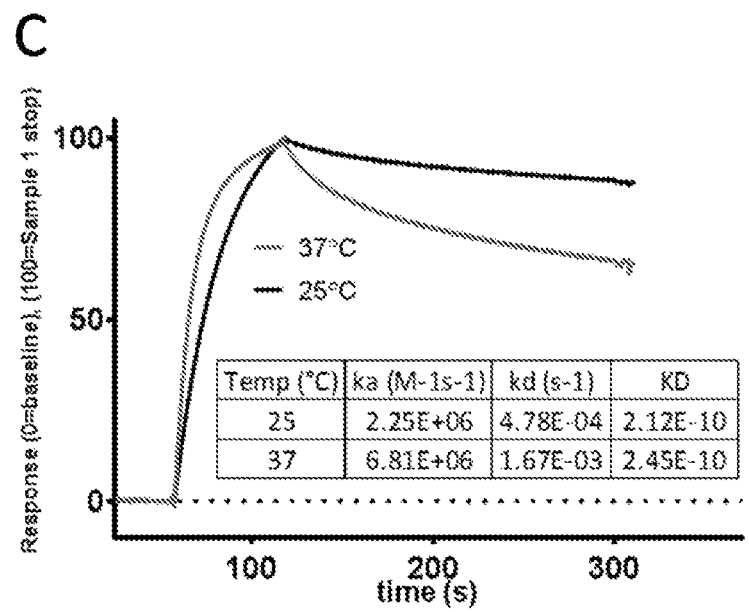
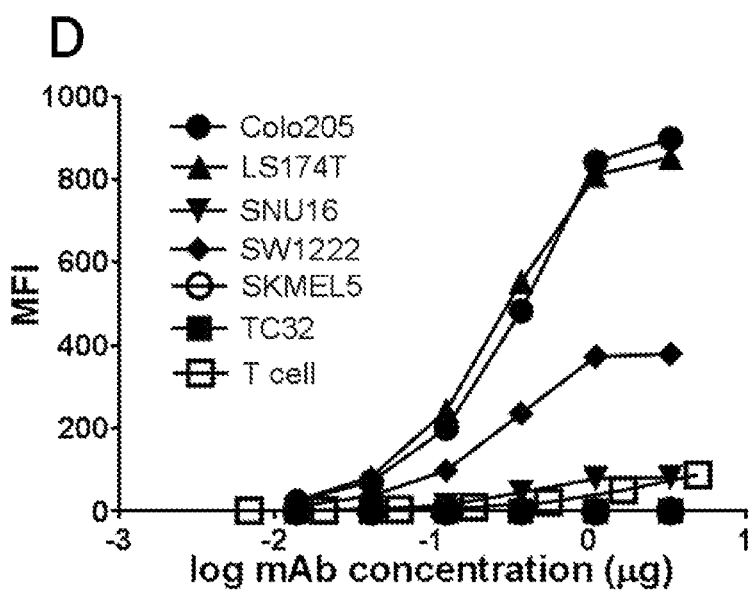

Figure 2
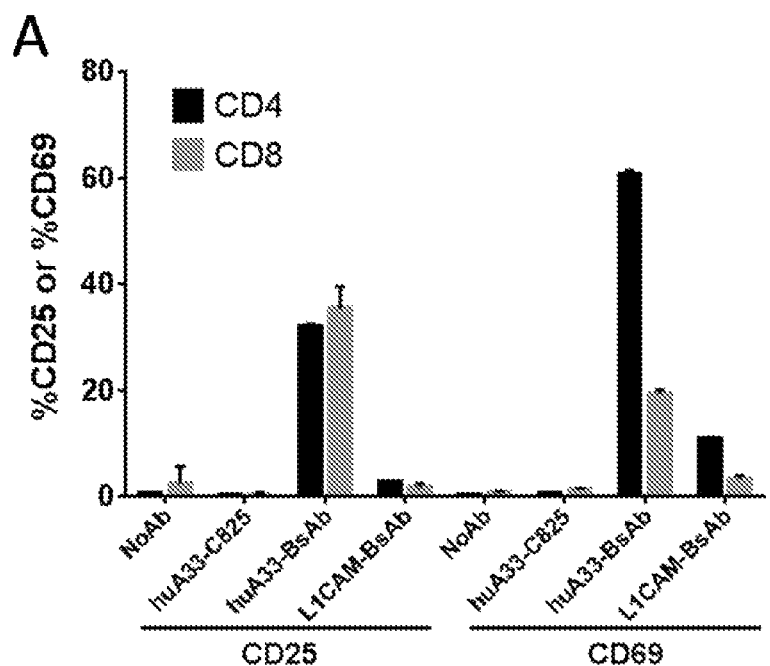
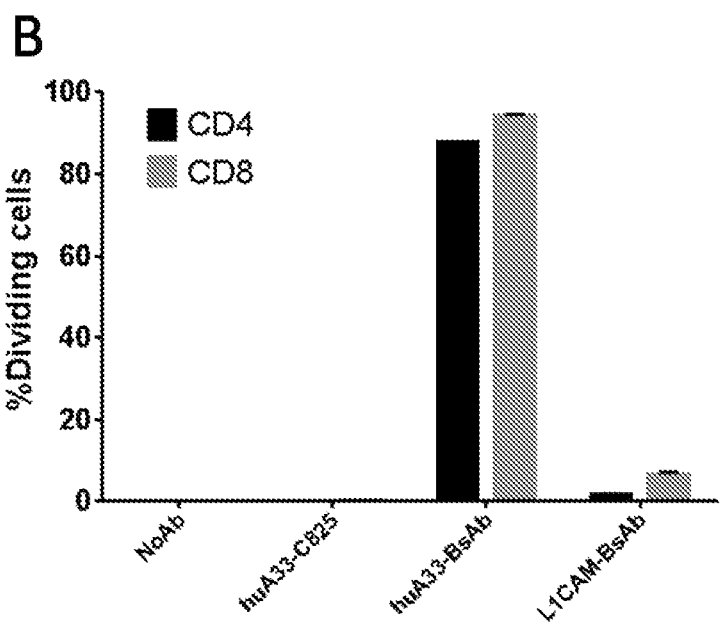

Figure 2 (contd.)
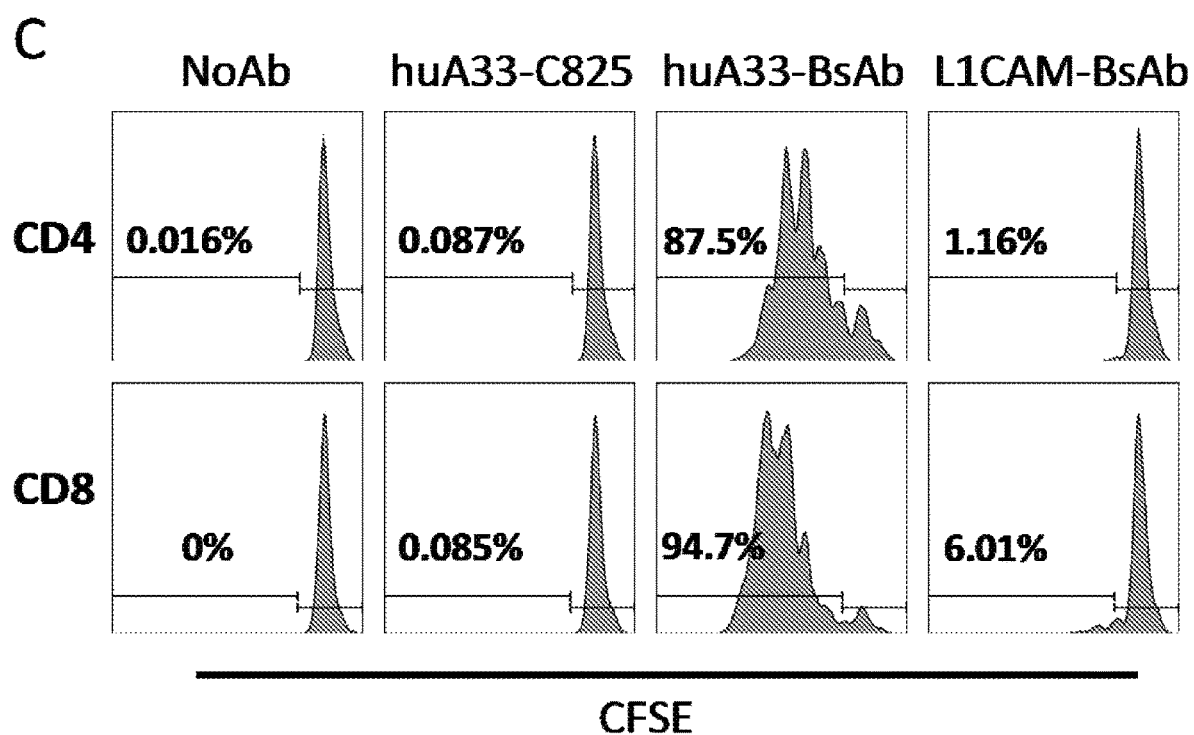

Figure 2 (contd.)
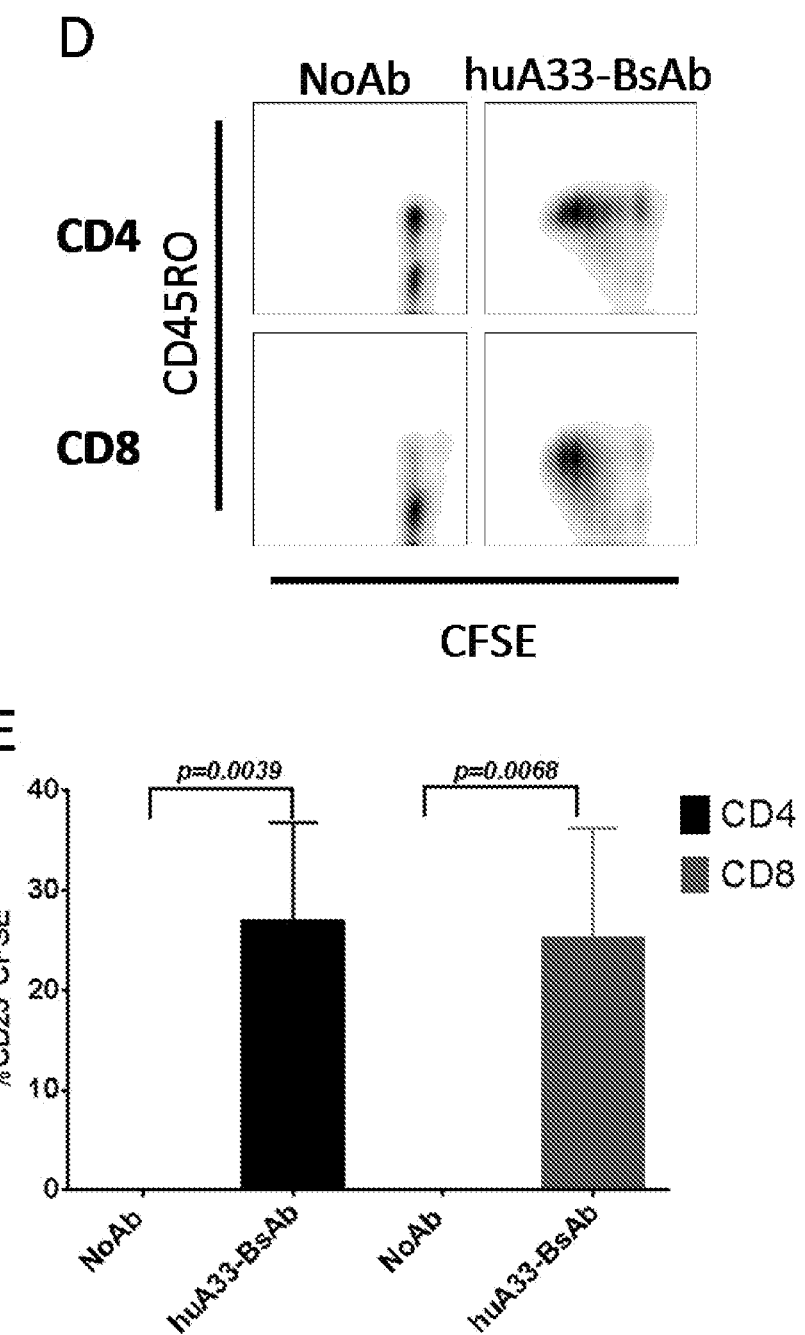

Figure 4
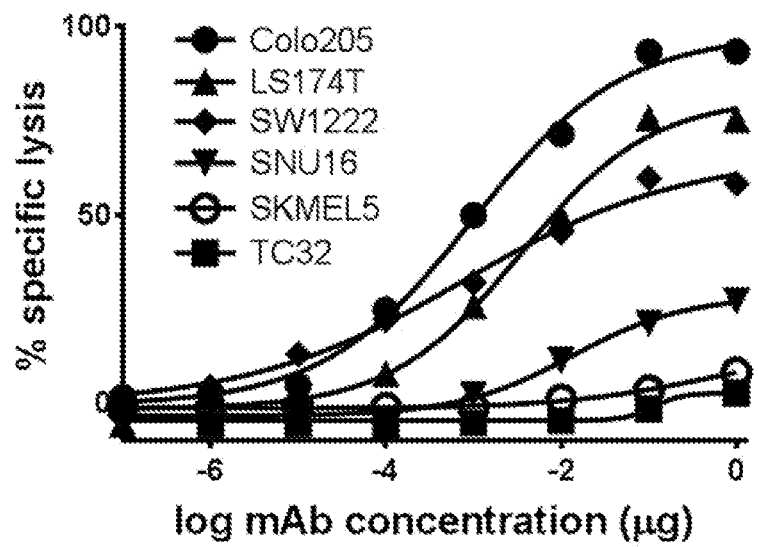
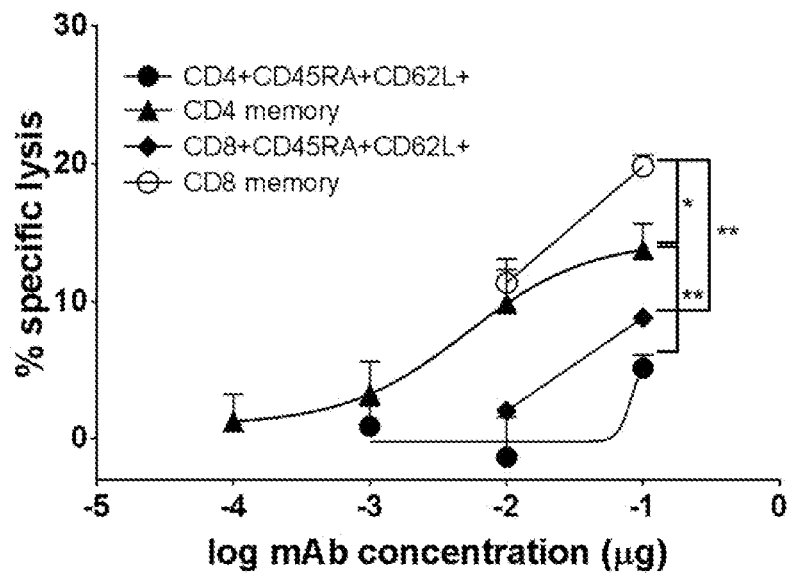

A

| Clones | Heavy Chain | | | | | | | Light Chain | | | | | | |
|---|---|---|---|---|---|---|---|---|---|---|---|---|---|---|
| | | | CDR1 | CDR2 | | | | | CDR1 | CDR2 | | CDR3 | | |
| | 5 | 13 | 28 | 32 | 52 | 53 | 107 | 18 | 31 | 32 | 53 | 83 | 90 | 91 |
| | V | K | A | Y | S | S | W | R | T | V | N | F | Q | H |
| 31 | | E | T | | | | | | | | | | | |
| 32 | E | | T | | | | | | | | | | | Y |
| 48 | | | | | | | | | | | D | | | Y |
| 49 | | | T | | | | | | L | | | | | |
| 53 | | | T | | | | | | | | | | | Y |
| 56 | | | | | | | R | | L | | | | | Y |
| 57 | | | T | | | | | S | | | | V | | Y |

B

| | $K_D$ | Fold difference/Parental |
|---|---|---|
| A33 31 | 3.87E-11 | 4.3 |
| A33 32 | 5.64E-12 | 29.7 |
| A33 48 | 3.29E-12 | 51.0 |
| A33 49 | 2.20E-11 | 7.6 |
| A33 53 | 1.75E-11 | 9.6 |
| A33 56 | 2.43E-11 | 6.9 |
| A33 57 | 1.56E-11 | 10.7 |
| A33-BsAb | 1.68E-10 | 1.0 |

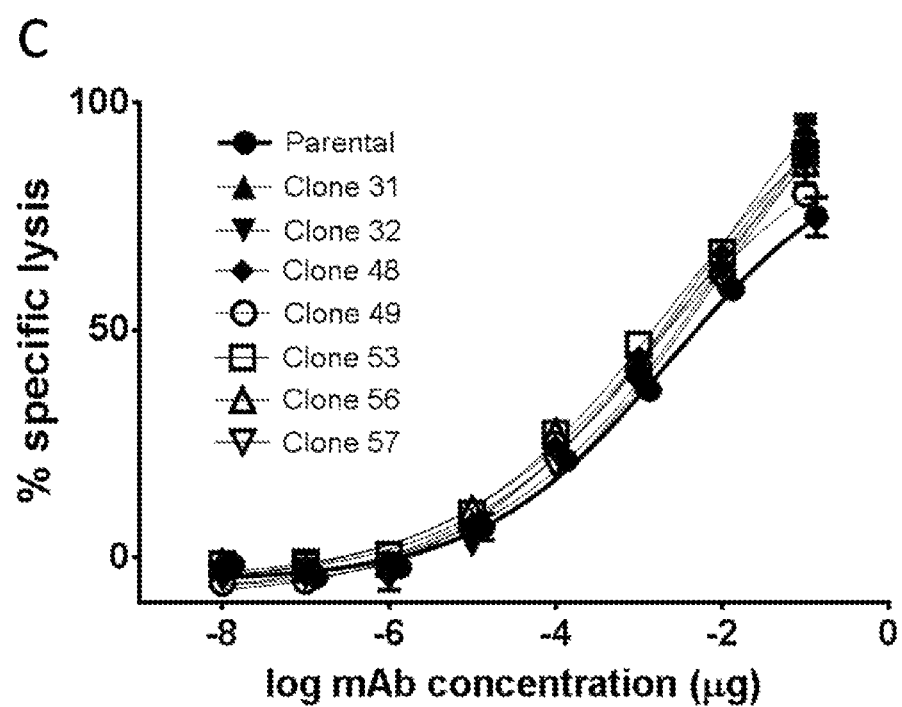
Figure 5 (contd.)

Figure 6
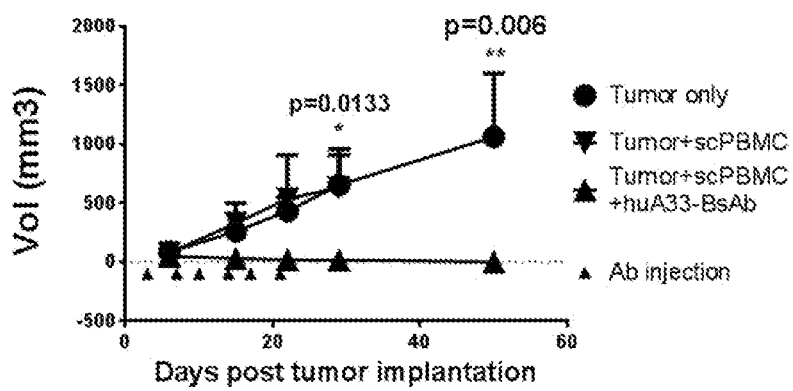
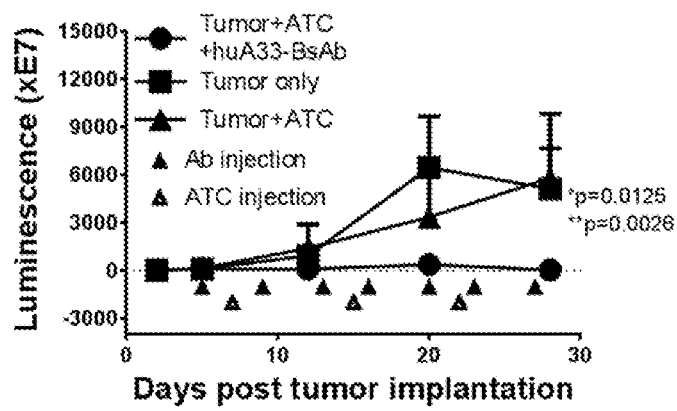
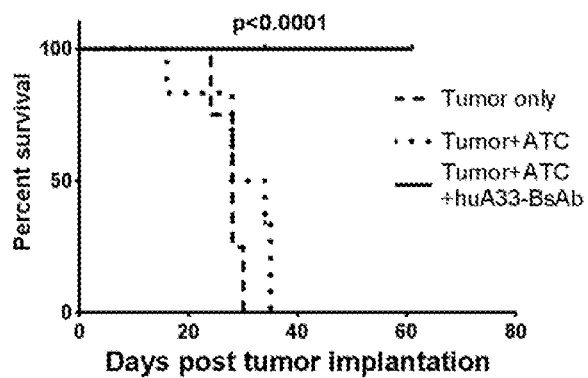

Figure 6 (contd.)
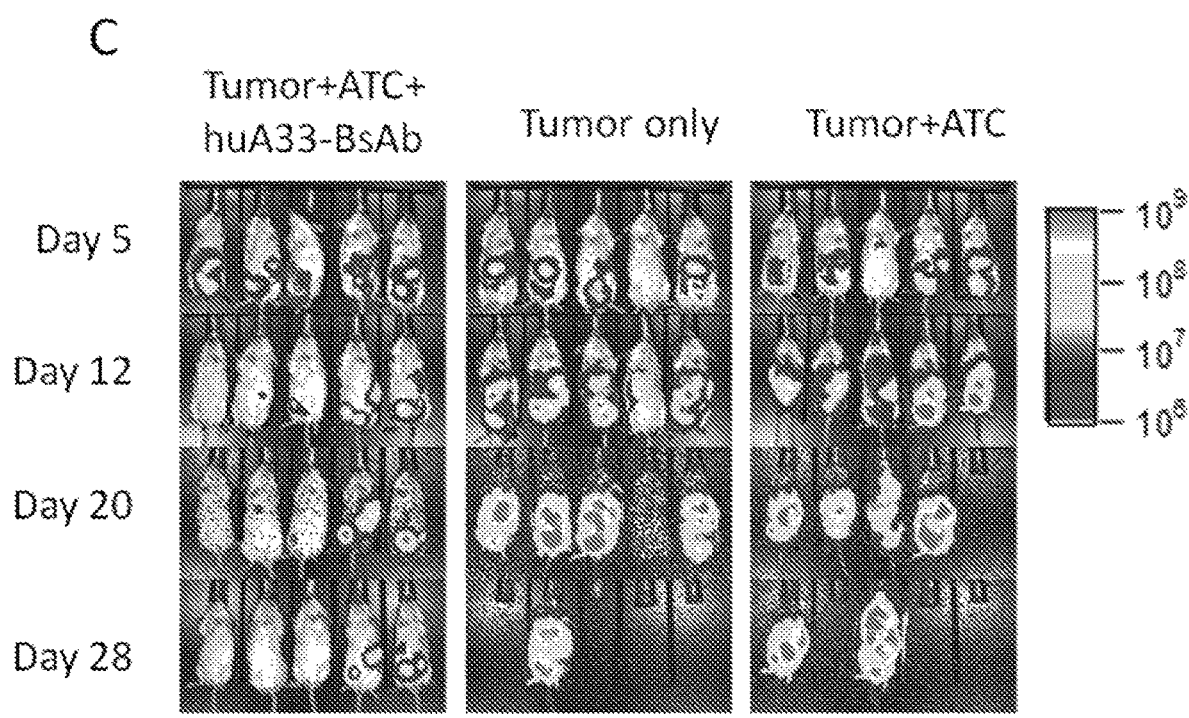

Figure 7 (contd.)
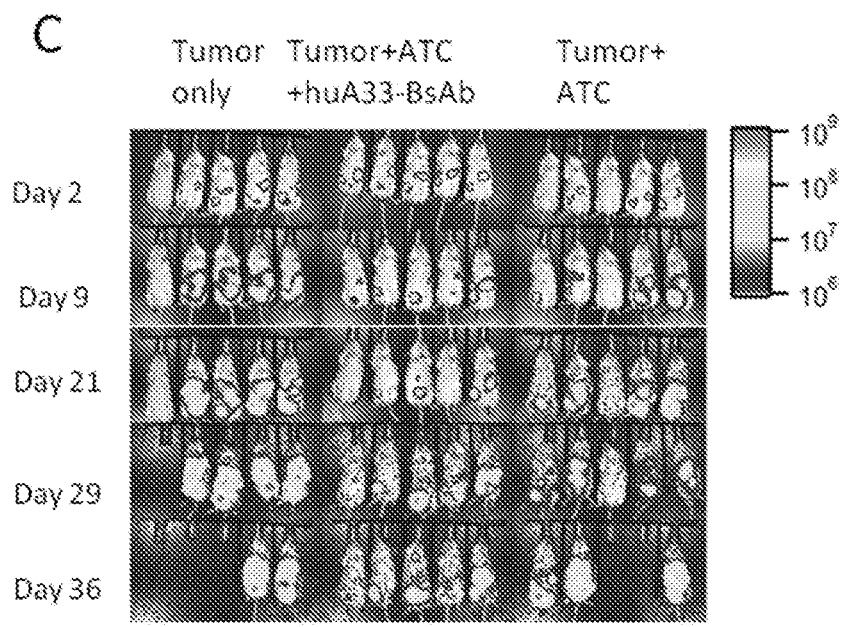
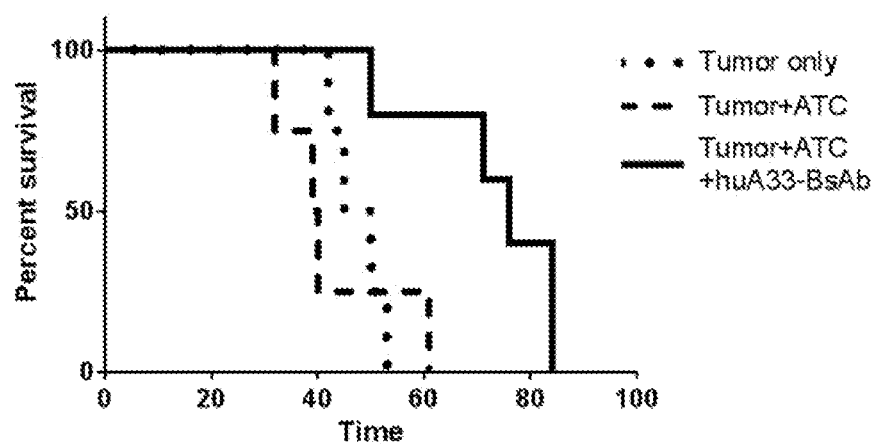

Figure 8
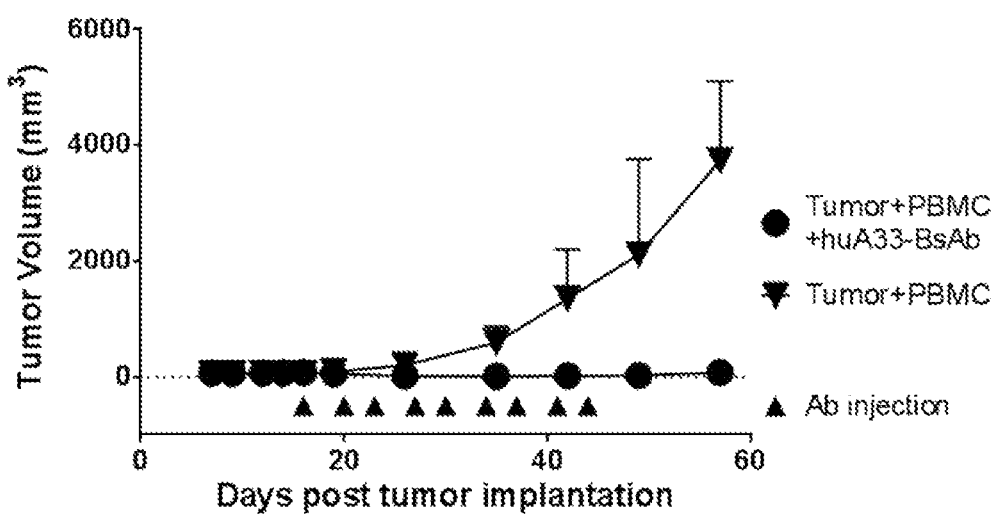
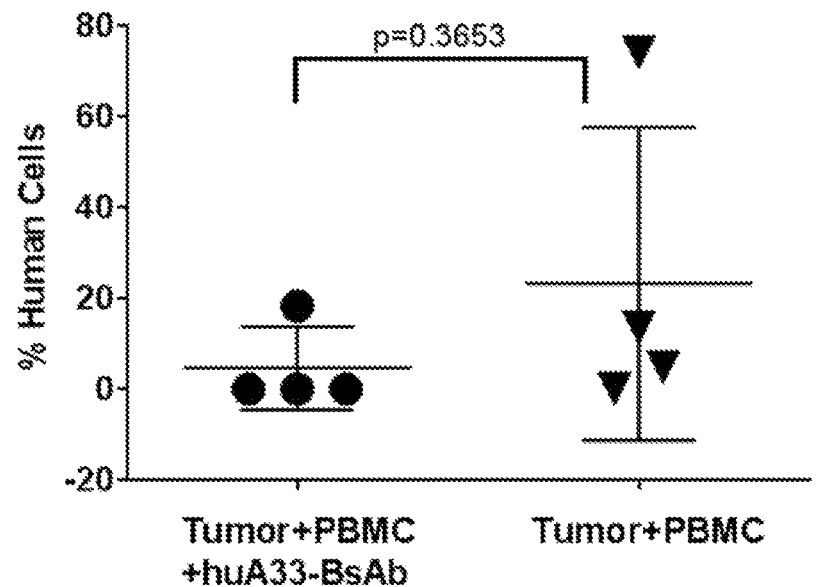

SPR

Figure 10
FACS

| Tumor Types | Cell lines | MFI |
|---|---|---|
| Breast CA | HTB-26 | 11 |
| Colorectal cancer | Colo205 | 3900 |
| Colorectal cancer | SW1222 | 1513 |
| Colorectal cancer | LS174T | 4776 |
| Ewing sarcoma | SK-E-LP | 6 |
| Ewing sarcoma | TC-32 | 6 |
| Ewing sarcoma | SKEAW | 7 |
| Ewing sarcoma | SK-E-RT | 8 |
| Ewing sarcoma | A4573 | 8 |
| Ewing sarcoma | SK-ES-1 | 9 |
| Gastric carcinoma | NCI-N87 | 7 |
| Gastric carcinoma | SNU16 | 303 |
| Lymphoma | NALM6 LUC_GFP | 5 |
| Melanoma | CRL-1424 G-361 | 13 |
| Melanoma | M14 LUC_GFP C11 | 6 |
| Melanoma | SKMEL5 | 9 |
| Melanoma | OCM1 LUC | 14 |
| mesothelioma | CRL-5915 NCI-H2052 | 7 |
| NB | IMR32 LUC | 4 |
| NB | NGP | 5 |
| NB | LS | 5 |
| NB | NMB7 | 6 |
| NB | BE(2)S | 6 |
| NB | 66N | 6 |
| NB | BE(2)M17 | 6 |
| NB | SKNSH | 7 |
| NB | SKNHM | 7 |
| NB | BE(2)N | 7 |
| NB | SKNAB | 7 |
| NB | NB5 | 7 |
| NB | BE(2)C | 9 |
| NB | 6S | 9 |
| NB | SKNAS | 10 |
| NB | SKNDZ | 10 |
| NB | SKNJB | 10 |
| NB | SKNZB | 10 |
| NB | SKNJC2 | 11 |
| NB | SH-EP1 | 12 |
| Non-SCLC | CRL-2882 NCI-H3255 | 6 |
| Non-SCLC | CRL-5810 NCI-H522 | 6 |
| Non-SCLC | CRL-5800 NCI-H23 | 8 |
| Non-SCLC | CRL-5875 NCI-H1563 | 9 |
| Non-SCLC | CRL-2868 HCC827 | 14 |
| Non-SCLC | CRL-5914 NCI-H2030 | 15 |
| Non-SCLC | CRL-5807 NCI-H358 | 18 |
| osteosarcoma | U2OS LUC_GFP | 7 |
| osteosarcoma | SAOS2 LUC_GFP | 8 |
| osteosarcoma | HOS LUC_GFP | 8 |
| osteosarcoma | 143B LUC_GFP | 9 |
| osteosarcoma | CRL-1427 LUC_GFP | 13 |
| ovarian CA | SKOV3 LUC | 12 |
| pancreas | CRL-1918 CFPAC-1 | 6 |
| pancreas | CRL-1997 HPAF-II | 6 |
| pancreas | CRL-1469 Panc1 | 7 |
| pancreas | CRL-2547 Panc 10.05 | 7 |
| pancreas | CRL-2172 SW 1990 | 7 |
| pancreas | HTB-80 Capan-2 | 10 |
| prostate | LNCaP | 7 |
| prostate | DU145 | 23 |
| SCLC | HTB-180 NCI-H345 | 7 |
| SCLC | NCI-N417 | 9 |

Figure 11
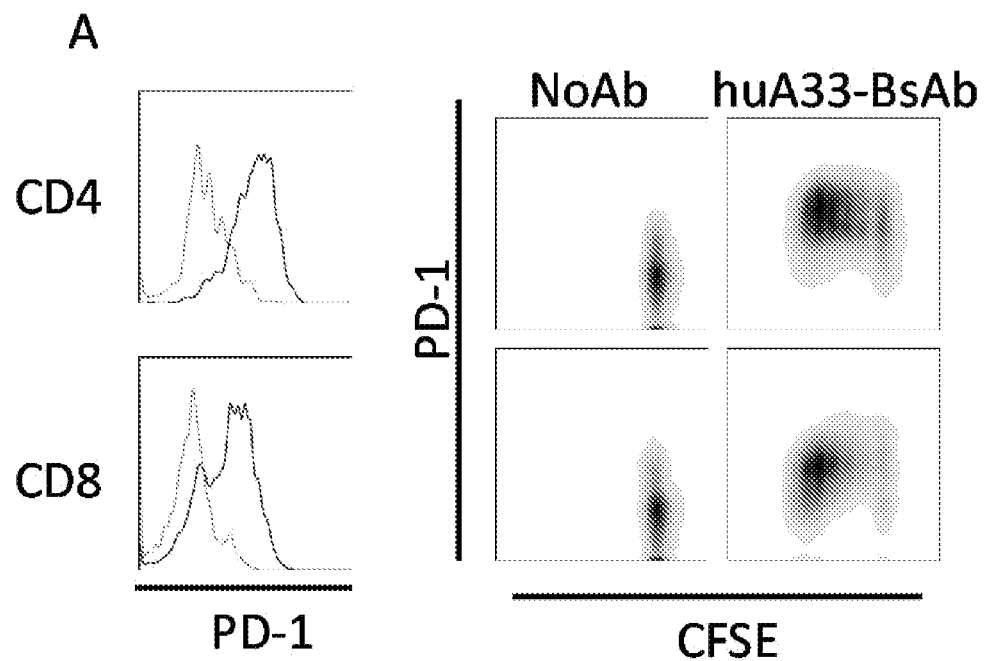
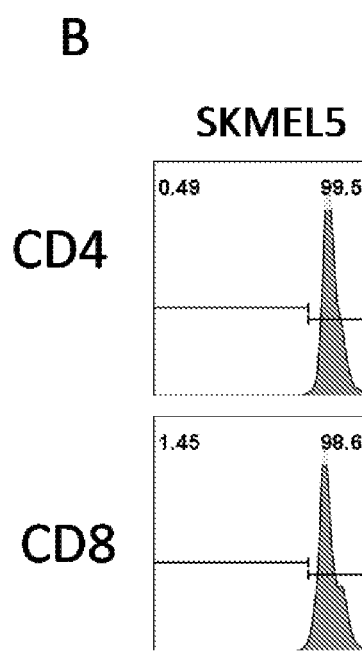

Figure 11 (contd.)
C
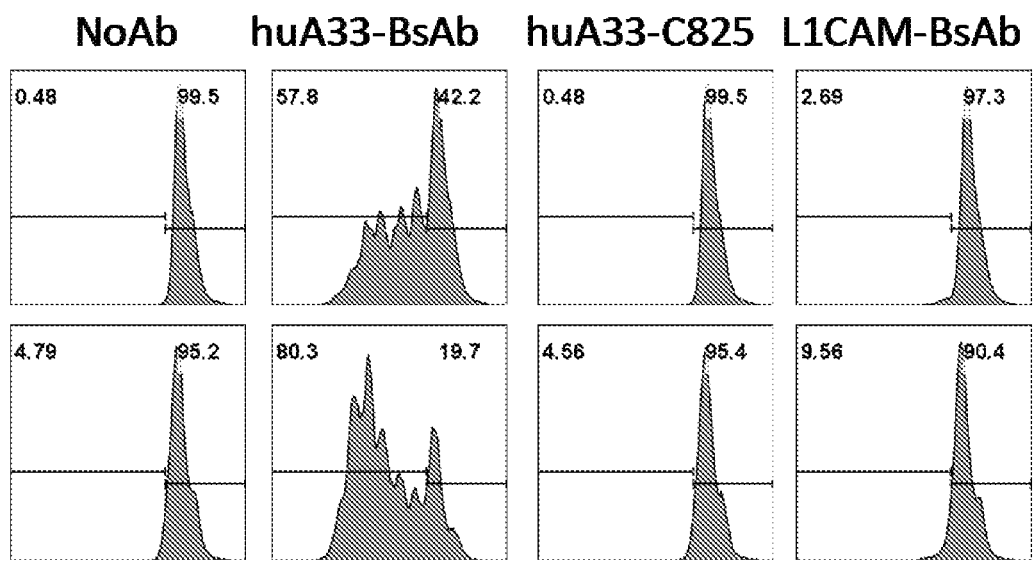

Figure 14 mA33-VH
EVKLVESGGGLVKPGGSLKLSCAASGFAFSTYDMSWVRQTPEKRLEWVA**TISS
GGSYTYYLDSVKGRFTISRDSARNTLYLQMSSLRSEDTALYYCAPTTVVPFAY**
WGQGTLVTVSA (SEQ ID NO: 1)

**IGHV3-21*01-IGHJ4*01 (most homolgous human sequence)**
EVQLVESGGGLVKPGGSLRLSCAASGFTFSSYSMNWVRQAPGKGLEWVSSISS
SSSYIYYADSVKGRFTISRDNAKNSLYLQMNSLRAEDTAVYYCARYFDYWGQGTL
VTVSS (SEQ ID NO: 2)

mA33-VL
DIVMTQSQKFMSTSVGDRVSITCKASQNVRTVVAWYQQKPGQSPKTLIY**LAS
NRHTGVPDRFTGSGSGTDFTLTISNVQSEDLADYFCLQHWSYPLT**FGSGTKLE
VKR (SEQ ID NO: 3)

**IGKV1-17*02-IGKJ2*01 (most homologous human sequence)**
DIQMTQSPSSLSASVGDRVTITCRASQGIRNDLGWYQQKPGKAPKRLIYAASSL
QSGVPSRFSGSG..SGTEFTLTISNLQPEDFATYYCLQHNSYPYTFGQGTKLEIK
(SEQ ID NO: 4)

Figure 15 huA33-H1 (3A3-H1)(SEQ ID NO: 5)
EVKLVESGGGLVKPGGSLRLSCAASGFAFSTYDMSWVRQAPEKRLEWVATISSGGSY
TYYLDSVKGRFTISRDSAKNSLYLQMNSLRAEDTALYYCAPTTVVPFAYWGQGTLVTV
SS huA33-H2 (3A3-H2) (SEQ ID NO: 6)
EVQLVESGGGLVKPGGSLRLSCAASGFAFSTYDMSWVRQAPGKRLEWVATISSGGSY
TYYLDSVKGRFTISRDNAKNSLYLQMNSLRAEDTAVYYCAPTTVVPFAYWGQGTLVTV
SS

Figure 16 huA33-H1 (3A3-H1) (SEQ ID NO: 7)
GAAGTGAAGCTGGTGGAATCTGGCGGCGGACTCGTGAAGCCTGGCGGCTCTCTGAGACTGTCTTGTGC
CGCCTCTGGCTTCGCCTTCTCCACCTACGACATGTCCTGGGTGCGACAGGCCCCTGAGAAGCGGCTGG
AATGGGTGGCCACAATCTCCTCCGGCGGCTCCTACACCTACTACCTGGACTCTGTGAAGGGCCGGTTCA
CCATCTCCCGGGACTCCGCCAAGAACTCCCTGTACCTGCAGATGAACAGCCTGCGGGCCGAGGACACC
GCCCTGTACTATTGTGCTCCCACCACCGTGGTGCCCTTCGCCTATTGGGGACAGGGCACCCTCGTGACC
GTGTCCTCT huA33-H2 (3A3-H2) (SEQ ID NO: 8)
GAGGTGCAGCTGGTGGAATCTGGCGGCGGACTCGTGAAGCCTGGCGGCTCTCTGAGACTGTCTTGTGC
CGCCTCTGGCTTCGCCTTCTCCACCTACGACATGTCCTGGGTGCGACAGGCCCCTGGCAAGAGACTGG
AATGGGTGGCCACAATCTCCTCCGGCGGCTCCTACACCTACTACCTGGACTCTGTGAAGGGCCGGTTCA
CCATCTCCCGGGACAACGCCAAGAACTCCCTGTACCTGCAGATGAACAGCCTGCGGGCCGAGGACACC
GCCGTGTACTATTGTGCTCCCACCACCGTGGTGCCCTTCGCCTATTGGGGACAGGGCACCCTCGTGACC
GTGTCCTCT

Figure 17 huA33-L1 (3A3-L1) (SEQ ID NO: 9)
DIQMTQSQSFMSTSVGDRVTITCKASQNVRTVVAWYQQKPGKSPKTLIYLASNRHT
GVPDRFSGSGSGTEFTLTISNVQSEDFADYFCLQHWSYPLTFGSGTKLEIKR huA33-L2 (3A3-L2) (SEQ ID NO: 10)
DIQMTQSQSSLSTSVGDRVTITCKASQNVRTVVAWYQQKPGKSPKTLIYLASNRHT
GVPSRFSGSGSGTEFTLTISNVQPEDFADYFCLQHWSYPLTFGSGTKLEIKR

Figure 18 huA33-L1 (3A3-L1)(SEQ ID NO: 11)
GACATCCAGATGACCCAGTCCCAGTCCTTCATGTCCACCTCCGTGGGCGACAGAGTGACCATCACA
TGCAAGGCCTCCCAGAACGTGCGGACCGTGGTGGCCTGGTATCAGCAGAAGCCTGGCAAGTCCC
CCAAGACCCTGATCTACCTGGCCTCCAACAGACACACCGGCGTGCCCGACAGATTCTCCGGCTCT
GGCTCTGGCACCGAGTTCACCCTGACCATCTCCAACGTGCAGTCCGAGGACTTCGCCGACTACTTC
TGTCTGCAACACTGGTCCTACCCCCTGACCTTCGGCTCCGGCACCAAGCTGGAAATCAAGAGA huA33-L2 (3A3-L2)(SEQ ID NO: 12)
GACATCCAGATGACCCAGTCCCAGTCCTCCCTGTCCACCTCCGTGGGCGACAGAGTGACCATCACA
TGCAAGGCCTCCCAGAACGTGCGGACCGTGGTGGCCTGGTATCAGCAGAAGCCTGGCAAGTCCC
CCAAGACCCTGATCTACCTGGCCTCCAACAGACACACCGGCGTGCCCTCCAGATTCTCCGGCTCTG
GCTCTGGCACCGAGTTCACCCTGACCATCTCCAACGTGCAGCCCGAGGACTTCGCCGACTACTTCT
GTCTGCAACACTGGTCCTACCCCCTGACCTTCGGCTCCGGCACCAAGCTGGAAATCAAGAGA

Figure 20

|         | $k_a$ (1/Ms) | $k_d$ (1/s) | $K_D$ (M) |
|---------|--------------|-------------|-----------|
| 3A3-chA33 | 2.03E+06 | 6.28E-04 | 3.10E-10 |
| 3A3-H1L1  | 1.71E+06 | 3.70E-04 | 2.17E-10 |
| 3A3-H1L2  | 2.64E+06 | 6.10E-04 | 2.32E-10 |
| 3A3-H2L1  | 1.48E+06 | 2.90E-04 | 1.96E-10 |
| 3A3-H2L2  | 2.15E+06 | 3.63E-04 | 1.69E-10 |

Figure 22

|  | $k_a$ (1/Ms) | $k_d$ (1/s) | $K_D$ (M) |
|---|---|---|---|
| huA33 (3A3-H2L2) | 2.15E+06 | 3.63E-04 | 1.69E-10 |
| hA33-mC825 | 1.85E+06 | 2.94E-03 | 1.59E-09 |

Figure 23

| Antibody | Target | Code | H1 | H2 | L1 | L2 |
|---|---|---|---|---|---|---|
| huA33 | A33 | 3A3 | 79.95737 | 83.24797 | 73.68187 | 77.13647 |

|  | VH | VL |
|---|---|---|
| hA33 | 83.07697 | 80.59097 |

Figure 24 chA33-IgG1

*Light chain* (SEQ ID NO: 13)
DIVMTQSQKFMSTSVGDRVSITCKASQNVRTVVAWYQQKPGQSPKTLIYLASNRHTGVP
DRFTGSGSGTDFTLTISNVQSEDLADYFCLQHWSYPLTFGSGTKLEVKRTVAAPSVFIFPP
SDEQLKSGTASVVCLLNNFYPREAKVQWKVDNALQSGNSQESVTEQDSKDSTYSLSSTL
TLSKADYEKHKVYACEVTHQGLSSPVTKSFNRGEC

*Heavy chain* (SEQ ID NO: 14)
EVKLVESGGGLVKPGGSLKLSCAASGFAFSTYDMSWVRQTPEKRLEWVATISSGGSYTYY
LDSVKGRFTISRDSARNTLYLQMSSLRSEDTALYYCAPTTVVPFAYWGQGTLVTVSAASTK
GPSVFPLAPSSKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPELLGGPSVFLF
PPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFS
CSVMHEALHNHYTQKSLSLSPGK

Figure 25 huA33-IgG1 (H2L2) Heavy Chain

*Amino acid:* (SEQ ID NO: 15)
EVQLVESGGGLVKPGGSLRLSCAASGFAFSTYDMSWVRQAPGKRLEWVATISSGGSYTYYLDSVKGRFTISRDNAKNSLYL
QMNSLRAEDTAVYYCAPTTVVPFAYWGQGTLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK

*cDNA:* (SEQ ID NO: 16)
GAGGTGCAGCTGGTGGAATCTGGCGGCGGACTCGTGAAGCCTGGCGGCTCTCTGAGACTGTCTTGTGCCGCCTCTGGCT
TCGCCTTCTCCACCTACGACATGTCCTGGGTGCGACAGGCCCCTGGCAAGAGACTGGAATGGGTGGCCACAATCTCCTC
CGGCGGCTCCTACACCTACTACCTGGACTCTGTGAAGGGCCGGTTCACCATCTCCCGGGACAACGCCAAGAACTCCCTGT
ACCTGCAGATGAACAGCCTGCGGGCCGAGGACACCGCCGTGTACTATTGTGCTCCCACCACCGTGGTGCCCTTCGCCTAT
TGGGGACAGGGCACCCTCGTGACCGTGTCCTCTGCTTCTACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCCGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACACCAAGGTGG
ACAAGAGAGTTGAGCCCAAATCTTGTGACAAAACTCACACATGCCCACCGTGCCCAGCACCTGAACTCCTGGGGGGACC
GTCAGTCTTCCTCTTCCCCCCAAAACCCAAGGACACCCTCATGATCTCCCGGACCCCTGAGGTCACATGCGTGGTGGTGG
ACGTGAGCCACGAAGACCCTGAGGTCAAGTTCAACTGGTACGTGGACGGCGTGGAGGTGCATAATGCCAAGACAAAGCC
GCGGGAGGAGCAGTACAACAGCACGTACCGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCCAAAGGGCAGCCC
CGAGAACCACAGGTGTACACCCTGCCCCCATCCCGGGATGAGCTGACCAAGAACCAGGTCAGCCTGACCTGCCTGGTCA
AAGGCTTCTATCCCAGCGACATCGCCGTGGAGTGGGAGAGCAATGGGCAGCCGGAGAACAACTACAAGACCACGCCTCC
CGTGCTGGACTCCGACGGCTCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCCCTGTCTCCGGGTAAA

Figure 26 huA33-IgG1 (H2L2) light chain

*Amino acid:* (SEQ ID NO: 17)
DIQMTQSQSSLSTSVGDRVTITCKASQNVRTVVAWYQQKPGKSPKTLIYLASNRHTGVPSRFSGSGSGTEFTLTISNVQ
PEDFADYFCLQHWSYPLTFGSGTKLEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

*cDNA:* (SEQ ID NO: 18)
GACATCCAGATGACCCAGTCCCAGTCCTCCCTGTCCACCTCCGTGGGCGACAGAGTGACCATCACATGCAAGGCCTC
CCAGAACGTGCGGACCGTGGTGGCCTGGTATCAGCAGAAGCCTGGCAAGTCCCCCAAGACCCTGATCTACCTGGCCT
CCAACAGACACACCGGCGTGCCCTCCAGATTCTCCGGCTCTGGCTCTGGCACCGAGTTCACCCTGACCATCTCCAAC
GTGCAGCCCGAGGACTTCGCCGACTACTTCTGTCTGCAACACTGGTCCTACCCCCTGACCTTCGGCTCCGGCACCAA
GCTGGAAATCAAGAGAACCGTGGCCGCTCCCTCCGTGTTCATCTTCCCACCTTCCGACGAGCAGCTGAAGTCCGGCA
CCGCTTCTGTCGTGTGCCTGCTGAACAACTTCTACCCCCGCGAGGCCAAGGTGCAGTGGAAGGTGGACAACGCCCTG
CAGTCCGGCAACTCCCAGGAATCCGTGACCGAGCAGGACTCCAAGGACAGCACCTACAGCCTGTCCTCTACCCTGAC
CCTGTCCAAGGCCGACTACGAGAAGCACAAGGTGTACGCCTGCGAAGTGACCCACCAGGGCCTGTCTAGCCCCGTG
ACCAAGTCTTTCAACCGGGGCGAGTGC

Figure 27 huA33-BsAb (H2L2) Heavy Chain

*Amino acid:* (SEQ ID NO: 19)
EVQLVESGGGLVKPGGSLRLSCAASGFAFSTYDMSWVRQAPGKRLEWVATISSGGSYTYYLDSVKGRFTISRDNAKNSLYL
QMNSLRAEDTAVYYCAPTTVVPFAYWGQGTLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYASTYRVVSVLTVLHQDWLNGKEYKCAVSNKA
LPAPIEKTISKAKGQPREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGK

*cDNA:* (SEQ ID NO: 20)
GAGGTGCAGCTGGTGGAATCTGGCGGCGGACTCGTGAAGCCTGGCGGCTCTCTGAGACTGTCTTGTGCCGCCTCTGGCT
TCGCCTTCTCCACCTACGACATGTCCTGGGTGCGACAGGCCCCTGGCAAGAGACTGGAATGGGTGGCCACAATCTCCTC
CGGCGGCTCCTACACCTACTACCTGGACTCTGTGAAGGGCCGGTTCACCATCTCCCGGGACAACGCCAAGAACTCCCTGT
ACCTGCAGATGAACAGCCTGCGGGCCGAGGACACCGCCGTGTACTATTGTGCTCCCACCACCGTGGTGCCCTTCGCCTAT
TGGGGACAGGGCACCCTCGTGACCGTGTCCTCTGCTTCTACCAAGGGCCCCTCTGTGTTTCCTCTGGCCCCCTCCAGCAA
GTCCACCTCTGGTGGAACAGCCGCCCTGGGCTGCCTCGTGAAGGACTACTTTCCCGAGCCCGTGACCGTGTCCTGGAAC
TCTGGCGCTCTGACCTCTGGCGTGCACACCTTCCCTGCTGTGCTGCAGTCTAGCGGCCTGTACTCCCTGTCCTCCGTCGT
GACAGTGCCCTCCAGCTCTCTGGGCACCCAGACCTACATCTGCAACGTGAACCACAAGCCCTCCAATACCAAGGTGGAC
AAGCGGGTGGAACCCAAGTCCTGCGACAAGACCCACACCTGTCCCCCTTGTCCTGCCCCTGAACTGCTGGGCGGACCTT
CCGTGTTCCTGTTCCCCCCAAAGCCCAAGGACACCCTGATGATCTCCCGGACCCCCGAAGTGACCTGCGTGGTGGTGGA
TGTGTCCCACGAGGACCCTGAAGTGAAGTTCAATTGGTACGTGGACGGCGTGGAAGTGCACAACGCCAAGACCAAGCCT
AGAGAGGAACAGTACGCCTCCACCTACCGGGTGGTGTCCGTGCTGACAGTGCTGCACCAGGACTGGCTGAACGGCAAA
GAGTACAAGTGCGCCGTGTCCAACAAGGCCCTGCCTGCCCCCATCGAAAAGACCATCTCCAAGGCCAAGGGCCAGCCCC
GGGAACCCCAGGTGTACACACTGCCCCCTAGCAGGGACGAGCTGACCAAGAACCAGGTGTCCCTGACCTGTCTCGTGAA
AGGCTTCTACCCCTCCGATATCGCCGTGGAATGGGAGTCCAACGGCCAGCCTGAGAACAACTACAAGACCACCCCCCCT
GTGCTGGACTCCGACGGCTCATTCTTCCTGTACAGCAAGCTGACCGTGGACAAGTCCCGGTGGCAGCAGGGCAACGTGT
TCTCCTGCTCCGTGATGCACGAGGCCCTGCACAACCACTACACCCAGAAGTCCCTGTCCCTGAGCCCCGGCAAA

Figure 28 huA33-BsAb (H2L2) light chain – huOKT3scFv

*Amino acid* (SEQ ID NO: 21)
DIQMTQSQSSLSTSVGDRVTITCKASQNVRTVVAWYQQKPGKSPKTLIYLASNRHTGVPSRFSGSGSGTEFTLTISNVQPEDFA
DYFCLQHWSYPLTFGSGTKLEIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGECTSGGGGSGGGGSGGGGSQVQLVQSGGGVVQPGRSLR
LSCKASGYTFTRYTMHWVRQAPGKCLEWIGYINPSRGYTNYNQKFKDRFTISRDNSKNTAFLQMDSLRPEDTGVYFCARYYDD
HYSLDYWGQGTPVTVSSGGGGSGGGGSGGGGSGGGGSGGGGSDIQMTQSPSSLSASVGDRVTITCSASSSVSYM
NWYQQTPGKAPKRWIYDTSKLASGVPSRFSGSGSGTDYTFTISSLQPEDIATYYCQQWSSNPFTFGCGTKLQITR

*cDNA:* (SEQ ID NO: 22)
GACATCCAGATGACCCAGTCCCAGTCCTCCCTGTCCACCTCCGTGGGCGACAGAGTGACCATCACATGCAAGGCCTCCCAGA
ACGTGCGGACCGTGGTGGCCTGGTATCAGCAGAAGCCTGGCAAGTCCCCCAAGACCCTGATCTACCTGGCCTCCAACAGAC
ACACCGGCGTGCCCTCCAGATTCTCCGGCTCTGGCTCTGGCACCGAGTTCACCCTGACCATCTCCAACGTGCAGCCCGAGG
ACTTCGCCGACTACTTCTGTCTGCAACACTGGTCCTACCCCCTGACCTTCGGCTCCGGCACCAAGCTGGAAATCAAGAGAAC
CGTGGCCGCTCCCTCCGTGTTCATCTTCCCACCTTCCGACGAGCAGCTGAAGTCCGGCACCGCTTCTGTCGTGTGCCTGCTG
AACAACTTCTACCCCGCGAGGCCAAGGTGCAGTGGAAGGTGGACAACGCCCTGCAGTCCGGCAACTCCCAGGAATCCGTG
ACCGAGCAGGACTCCAAGGACAGCACCTACAGCCTGTCCTCTACCCTGACCCTGTCCAAGGCCGACTACGAGAAGCACAAG
GTGTACGCCTGCGAAGTGACCCACCAGGGCCTGTCTAGCCCCGTGACCAAGTCTTTCAACCGGGGCGAGTGCACTAGTGGC
GGCGGAGGATCTGGCGGAGGTGGAAGCGGAGGCGGAGGATCTCAGGTGCAGCTGGTGCAGAGCGGAGGCGGAGTGGTG
CAGCCTGGCAGATCCCTGAGACGTGCCTGCAAGGCCCTCCGGCTACACCTTCACCCGGTACACCATGCACTGGGTGCGACAG
GCCCCTGGCAAGTGCCTGGAATGGATCGGCTACATCAACCCCTCCCGGGGCTACACCAACTACAACCAGAAGTTCAAGGAC
CGGTTCACCATCTCCCGGGACAACTCCAAGAACACCGCCTTTCTGCAGATGGACTCCCTGCGGCCTGAGGATACCGGCGTGT
ACTTCTGCGCCCGGTACTACGACGACCACTACTCCCTGGACTACTGGGGCCAGGGAACCCCTGTGACAGTGTCATCTGGTGG
CGGAGGAAGTGGGGGAGGCGGATCAGGTGGTGGTGGATCAGGCGGGGAGGTTCAGGGGGTGGCGGTTCTGGGGGAGG
GGGCTCTGATATTCAGATGACTCAGAGCCCTTCCAGCCTGAGCGCCTCCGTGGGAGATCGCGTGACAATTACCTGCTCTGCC
TCCTCCTCCGTGTCTTACATGAATTGGTATCAGCAGACCCCTGGGAAGGCTCCTAAGCGGTGGATCTACGACACCTCCAAGCT
GGCCTCTGGCGTGCCCAGCAGGTTTTCTGGCTCCGGCAGCGGCACAGATTATACCTTCACCATCAGCTCCCTGCAGCCAGAA
GATATCGCTACCTATTATTGTCAGCAGTGGTCCTCCAACCCTTTCACCTTCGGCTGCGGCACAAAGCTGCAGATCACAAGA

Figure 29

| LOCATION OF MODIFICATION | DESCRIPTION |
|---|---|
| Heavy chain | Mutation to reduce binding to the Fc receptor (as an example, N297A mutation) |
| | Mutation to destroy a glycosylation site (as an example, N297A mutation) |
| | Mutation to reduce C1q binding (as an example, K322A mutation) |
| Linker conjugating the light chain to the huOKT3 scFv | Increase or decrease the length of the linker |
| huOKT3 scFv $V_H$ | Mutation to increase stabilization and/or reduce aggregation (as an example, introduce disulfide binding between $V_H 40$ and $V_L 100$ (according to Kabat numbering), as an example, $V_H$ G44C and $V_L$ Q100C) |
| | Reduce aggregation (as an example, C105S mutation) |
| huOKT3 scFv $V_L$ | Mutation to increase stabilization and/or reduce aggregation (as an example,, introduce disulfide binding between $V_H 40$ and $V_L 100$ (according to Kabat numbering), as an example, $V_H$ G44C and $V_L$ Q100C) |
| huOKT3 intra-scFv linker | Increase or decrease the length of the linker (5 aa – 30 aa) |

Figure 30 huA33-BsAb (H2L2) – Clone 31 Heavy Chain (SEQ ID NO: 23)

EVQLVESGGGLVEPGGSLRLSCAASGFTFSTYDMSWVRQAPGKRLEWVATISSGGSYTYYLDSVKGRFT
ISRDNAKNSLYLQMNSLRAEDTAVYYCAPTTVVPFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCAVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK huA33-BsAb (H2L2) – Clone 31 light chain – huOKT3scFv (SEQ ID NO: 24)

DIQMTQSQSSLSTSVGDRVTITCKASQNVRTVVAWYQQKPGKSPKTLIYLASNRHTGVPSRFSGSGSGT
EFTLTISNVQPEDFADYFCLQHWSYPLTFGSGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNR
GECTSGGGGSGGGGSGGGGSQVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVYFCARYYDDHYSLDYWGQGTPV
TVSSGGGGSGGGGSGGGGSGGGGSGGGGSDIQMTQSPSSLSASVGDRVTITCSASSSVSYM
NWYQQTPGKAPKRWIYDTSKLASGVPSRFSGSGSGTDYTFTISSLQPEDIATYYCQQWSSNPFTFGCGT
KLQITR

Figure 31 huA33-BsAb (H2L2) – Clone 32 Heavy Chain (SEQ ID NO: 25)

EVQLEESGGGLVKPGGSLRLSCAASGFTFSTYDMSWVRQAPGKRLEWVATISSGGSYTYYLDSVKGRFT
ISRDNAKNSLYLQMNSLRAEDTAVYYCAPTTVVPFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCAVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK huA33-BsAb (H2L2) – Clone 32 light chain – huOKT3scFv(SEQ ID NO: 26)

DIQMTQSQSSLSTSVGDRVTITCKASQNVRTVVAWYQQKPGKSPKTLIYLASNRHTGVPSRFSGSGSGT
EFTLTISNVQPEDFADYFCLQYWSYPLTFGSGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNR
GECTSGGGGSGGGGSGGGGSQVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVYFCARYYDDHYSLDYWGQGTPV
TVSSGGGGSGGGGSGGGGSGGGGSGGGGSGGGGSDIQMTQSPSSLSASVGDRVTITCSASSSVSYM
NWYQQTPGKAPKRWIYDTSKLASGVPSRFSGSGSGTDYTFTISSLQPEDIATYYCQQWSSNPFTFGCGT
KLQITR

Figure 32 huA33-BsAb (H2L2) – Clone 48 Heavy Chain (SEQ ID NO: 27)

EVQLVESGGGLVKPGGSLRLSCAASGFAFSTYDMSWVRQAPGKRLEWVATISSGGSYTYYLDSVKGRFTI
SRDNAKNSLYLQMNSLRAEDTAVYYCAPTTVVPFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCAVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK huA33-BsAb (H2L2) – Clone 48 light chain - huOKT3scFv (SEQ ID NO: 28)

DIQMTQSQSSLSTSVGDRVTITCKASQNVRTVVAWYQQKPGKSPKTLIYLASDRHTGVPSRFSGSGSGT
EFTLTISNVQPEDFADYFCLQYWSYPLTFGSGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNR
GECTSGGGGSGGGGSGGGGSQVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVYFCARYYDDHYSLDYWGQGTPV
TVSSGGGGSGGGGSGGGGSGGGGSGGGGSDIQMTQSPSSLSASVGDRVTITCSASSSVSYM
NWYQQTPGKAPKRWIYDTSKLASGVPSRFSGSGSGTDYTFTISSLQPEDIATYYCQQWSSNPFTFGCGT
KLQITR

Figure 33 huA33-BsAb (H2L2) – Clone 49 Heavy Chain (SEQ ID NO: 29)

EVQLVESGGGLVKPGGSLRLSCAASGFTFSTYDMSWVRQAPGKRLEWVATISSGGSYTYYLDSVKGRFT
ISRDNAKNSLYLQMNSLRAEDTAVYYCAPTTVVPFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCAVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK huA33-BsAb (H2L2) – Clone 49 light chain - huOKT3scFv (SEQ ID NO: 30)

DIQMTQSQSSLSTSVGDRVTITCKASQNVRTLVAWYQQKPGKSPKTLIYLASNRHTGVPSRFSGSGSGT
EFTLTISNVQPEDFADYFCLQHWSYPLTFGSGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNR
GECTSGGGGSGGGGSGGGGSQVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVYFCARYYDDHYSLDYWGQGTPV
TVSSGGGGSGGGGSGGGGSGGGGSGGGGSGGGGSDIQMTQSPSSLSASVGDRVTITCSASSSVSYM
NWYQQTPGKAPKRWIYDTSKLASGVPSRFSGSGSGTDYTFTISSLQPEDIATYYCQQWSSNPFTFGCGT
KLQITR

Figure 34 huA33-BsAb (H2L2) – Clone 53 Heavy Chain (SEQ ID NO: 31)

EVQLVESGGGLVKPGGSLRLSCAASGFTFSTYDMSWVRQAPGKRLEWVATISSGGSYTYYLDSVKGRFT
ISRDNAKNSLYLQMNSLRAEDTAVYYCAPTTVVPFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCAVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK huA33-BsAb (H2L2) – Clone 53 light chain – huOKT3scFv(SEQ ID NO: 32)

DIQMTQSQSSLSTSVGDRVTITCKASQNVRTVVAWYQQKPGKSPKTLIYLASNRHTGVPSRFSGSGSGT
EFTLTISNVQPEDFADYFCLQYWSYPLTFGSGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNR
GECTSGGGGSGGGGSGGGGSQVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVYFCARYYDDHYSLDYWGQGTPV
TVSSGGGGSGGGGSGGGGSGGGGSGGGGSGGGGSDIQMTQSPSSLSASVGDRVTITCSASSSVSYM
NWYQQTPGKAPKRWIYDTSKLASGVPSRFSGSGSGTDYTFTISSLQPEDIATYYCQQWSSNPFTFGCGT
KLQITR

Figure 35 huA33-BsAb (H2L2) – Clone 56 Heavy Chain (SEQ ID NO: 33)

EVQLVESGGGLVKPGGSLRLSCAASGFAFSTYDMSWVRQAPGKRLEWVATISSGGSYTYYLDSVKGRFTI
SRDNAKNSLYLQMNSLRAEDTAVYYCAPTTVVPFAY<u>R</u>GQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCAVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK huA33-BsAb (H2L2) – Clone 56 light chain – huOKT3scFv (SEQ ID NO: 34)

DIQMTQSQSSLSTSVGDRVTITCKASQNVRT<u>L</u>VAWYQQKPGKSPKTLIYLASNRHTGVPSRFSGSGSGT
EFTLTISNVQPEDFADYFCLQ<u>Y</u>WSYPLTFGSGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNR
GECTS<u>GGGGSGGGGSGGGGS</u>QVQLVQSGGGVVQPGRSLRLSCKASGYTFTRYTMHWVRQAPGKCLE
WIGYINPSRGYTNYNQKFKDRFTISRDNSKNTAFLQMDSLRPEDTGVYFCARYYDDHYSLDYWGQGTPV
TVSS<u>GGGGSGGGGSGGGGSGGGGSGGGGSGGGGS</u>DIQMTQSPSSLSASVGDRVTITCSASSSVSYM
NWYQQTPGKAPKRWIYDTSKLASGVPSRFSGSGSGTDYTFTISSLQPEDIATYYCQQWSSNPFTFGCGT
KLQITR

Figure 36 huA33-BsAb (H2L2) – Clone 57 Heavy Chain (SEQ ID NO: 35)

EVQLVESGGGLVKPGGSLRLSCAASGFTFSTYDMSWVRQAPGKRLEWVATISSGGSYTYYLDSVKGRFT
ISRDNAKNSLYLQMNSLRAEDTAVYYCAPTTVVPFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCAVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK huA33-BsAb (H2L2) – Clone 57 light chain - huOKT3scFv (SEQ ID NO: 36)

DIQMTQSQSSLSTSVGDSVTITCKASQNVRTVVAWYQQKPGKSPKTLIYLASNRHTGVPSRFSGSGSGT
EFTLTISNVQPEDVADYFCLQYWSYPLTFGSGTKLEIKRTVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSFN
RGECTSGGGGSGGGGSGGGGSQVQLVQSGGGVVQPGRSLRLSCKASGYTFTRYTMHWVRQAPGKCL
EWIGYINPSRGYTNYNQKFKDRFTISRDNSKNTAFLQMDSLRPEDTGVYFCARYYDDHYSLDYWGQGTP
VTVSSGGGGSGGGGSGGGGSGGGGSGGGGSGGGGSDIQMTQSPSSLSASVGDRVTITCSASSSVSY
MNWYQQTPGKAPKRWIYDTSKLASGVPSRFSGSGSGTDYTFTISSLQPEDIATYYCQQWSSNPFTFGCG
TKLQITR

Figure 37 huA33-huC825 (H2L2) Heavy Chain

*Amino acid:* (SEQ ID NO: 58)
EVQLVESGGGLVKPGGSLRLSCAASGFAFSTYDMSWVRQAPGKRLEWVATISSGGSYTYYLDSVKGRFTISRDNAKNSLYL
QMNSLRAEDTAVYYCAPTTVVPFAYWGQGTLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYASTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGK

*cDNA:* (SEQ ID NO: 59)
GAGGTGCAGCTGGTGGAATCTGGCGGCGGACTCGTGAAGCCTGGCGGCTCTCTGAGACTGTCTTGTGCCGCCTCTGGCT
TCGCCTTCTCCACCTACGACATGTCCTGGGTGCGACAGGCCCCTGGCAAGAGACTGGAATGGGTGGCCACAATCTCCTC
CGGCGGCTCCTACACCTACTACCTGGACTCTGTGAAGGGCCGGTTCACCATCTCCCGGGACAACGCCAAGAACTCCCTGT
ACCTGCAGATGAACAGCCTGCGGGCCGAGGACACCGCCGTGTACTATTGTGCTCCCACCACCGTGGTGCCCTTCGCCTAT
TGGGGACAGGGCACCCTCGTGACCGTGTCCTCTGCTTCTACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACACCAAGGTGG
ACAAGAGAGTTGAGCCCAAATCTTGTGACAAAACTCACACATGCCCACCGTGCCCAGCACCTGAACTCCTGGGGGGACC
GTCAGTCTTCCTCTTCCCCCCAAAACCCAAGGACACCCTCATGATCTCCCGGACCCCTGAGGTCACATGCGTGGTGGTGG
ACGTGAGCCACGAAGACCCTGAGGTCAAGTTCAACTGGTACGTGGACGGCGTGGAGGTGCATAATGCCAAGACAAAGCC
GCGGGAGGAGCAGTACGCCAGCACGTACCGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCCAAAGGGCAGCCC
CGAGAACCACAGGTGTACACCCTGCCCCCATCCCGGGATGAGCTGACCAAGAACCAGGTCAGCCTGACCTGCCTGGTCA
AAGGCTTCTATCCCAGCGACATCGCCGTGGAGTGGGAGAGCAATGGGCAGCCGGAGAACAACTACAAGACCACGCCTCC
CGTGCTGGACTCCGACGGCTCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCCCTGTCTCCGGGTAAA

Figure 38 huA33-huC825 (H2L2) light chain – huC825scFv

*Amino acid:* (SEQ ID NO: 60)
DIQMTQSQSSLSTSVGDRVTITCKASQNVRTVVAWYQQKPGKSPKTLIYLASNRHTGVPSRFSGSGSGTEFTLTISNVQPEDFA
DYFCLQHWSYPLTFGSGTKLEIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGECTSGGGGSGGGGSGGGGSGGGGSHVQLVESGGGLVQPGGSLR
LSCAASGFSLTDYGVHWVRQAPGKGLEWLGVIWSGGGTAYNTALISRFTISRDNSKNTLYLQMNSLRAEDTAVYYCARRGSYPY
NYFDAWGCGTLVTVSSGGGGSGGGGSGGGGSGGGGSGGGGSQAVVTQEPSLTVSPGGTVTLTCGSSTGAVTASNY
ANWVQQKPGQCPRGLIGGHNNRPPGVPARFSGSLLGGKAALTLLGAQPEDEAEYYCALWYSDHWVIGGGTKLTVLG

*cDNA:* (SEQ ID NO: 61)
GACATCCAGATGACCCAGTCCCAGTCCTCCCTGTCCACCTCCGTGGGCGACAGAGTGACCATCACATGCAAGGCCTCCCAGA
ACGTGCGGACCGTGGTGGCCTGGTATCAGCAGAAGCCTGGCAAGTCCCCCAAGACCCTGATCTACCTGGCCTCCAACAGAC
ACACCGGCGTGCCCTCCAGATTCTCCGGCTCTGGCTCTGGCACCGAGTTCACCCTGACCATCTCCAACGTGCAGCCCGAGG
ACTTCGCCGACTACTTCTGTCTGCAACACTGGTCCTACCCCCTGACCTTCGGCTCCGGCACCAAGCTGGAAATCAAGAGAAC
CGTGGCCGCTCCCTCCGTGTTCATCTTCCCACCTTCCGACGAGCAGCTGAAGTCCGGCACCGCTTCTGTCGTGTGCCTGCTG
AACAACTTCTACCCCCGCGAGGCCAAGGTGCAGTGGAAGGTGGACAACGCCCTGCAGTCCGGCAACTCCCAGGAATCCGTG
ACCGAGCAGGACTCCAAGGACAGCACCTACAGCCTGTCCTCTACCCCTGACCCTGTCCAAGGCCGACTACGAGAAGCACAAG
GTGTACGCCTGCGAAGTGACCCACCAGGGCCTGTCTAGCCCCGTGACCAAGTCTTTCAACCGGGGCGAGTGCACTAGTGGC
GGCGGAGGATCTGGCGGAGGTGGAAGTGGGGGAGGCGGATCTCATGTGCAGCTGGTGGAAAGCGGAGGCGGCCTGGTGC
AGCCTGGGGGATCTCTGAGACTGTCTTGTGCCGCCAGCGGCTTCTCCCTGACCGATTATGGCGTGCACTGGGTGCGACAGG
CCCCTGGCAAAGGACTGGAATGGCTGGGAGTGATTTGGAGTGGCGGAGGCACCGCCTACAACACCGCCCTGATCTCCCGGT
TCACCATCAGCCGGGACAACTCCAAGAACACCCTGTACCTGCAGATGAACTCCCTGCGGGCCGAGGACACCGCTGTGTACT
ACTGCGCCAGACGGGGCTCCTACCCCTACAACTACTTCGACGCTTGGGGCTGCGGCACCCTCGTGACAGTGTCTAGCGGAG
GGGGAGGTTCTGGGGGCGGAGGTTCAGGTGGTGGTGGTTCCGGGGGTGGTGGCTCTGGTGGCGGTGGTTCTGGCGGTGG
CGGATCTCAGGCTGTCGTGACCCAGGAACCCAGCCTGACTGTGTCTCCTGGCGGAACCGTGACCCTGACCTGCGGATCTTCT
ACCGGCGCTGTGACCGCCAGCAACTACGCCAATTGGGTGCAGCAGAAACCTGGACAGTGCCCTAGAGGCCTGATCGGCGG
CCACAACAACAGACCTCCAGGCGTGCCAGCCCGGTTCTCTGGATCTCTGCTGGGCGGAAAGGCCGCTCTGACACTGCTGGG
TGCTCAGCCTGAGGACGAGGCCGAGTACTACTGTGCCCTGTGGTACTCCGACCACTGGGTCATCGGAGGCGGGACCAAGCT
GACCGTGCTGGGA

Figure 39 huA33-mC825 (H2L2) Heavy Chain (SEQ ID NO: 62)

EVQLVESGGGLVKPGGSLRLSCAASGFAFSTYDMSWVRQAPGKRLEWVATISSGGSYTYYLDSVKGRFTI
SRDNAKNSLYLQMNSLRAEDTAVYYCAPTTVVPFAYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK huA33-mC825 (H2L2) light chain – mC825scFv (SEQ ID NO: 63)

DIQMTQSQSSLSTSVGDRVTITCKASQNVRTVVAWYQQKPGKSPKTLIYLASNRHTGVPSRFSGSGSGT
EFTLTISNVQPEDFADYFCLQHWSYPLTFGSGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNR
GECTSGGGGSGGGGSGGGGSHVKLQESGPGLVQPSQSLSLTCTVSGFSLTDYGVHWVRQSPGKGLEW
LGVIWSGGGTAYNTALISRLNIYRDNSKNQVFLEMNSLQAEDTAMYYCARRGSYPYNYFDAWGCGTTVT
VSSGGGGSGGGGSGGGGSGGGGSGGGGSGGGGSQAVVIQESALTTPPGETVTLTCGSSTGAVTASNY
ANWVQEKPDHCFTGLIGGHNNRPPGVPARFSGSLIGDKAALTIAGTQTEDEAIYFCALWYSDHWVIGGG
TRLTVLG

SEQUENCE LISTING

```
<160> NUMBER OF SEQ ID NOS: 76

<210> SEQ ID NO 1
<211> LENGTH: 117
<212> TYPE: PRT
<213> ORGANISM: Mus sp.

<400> SEQUENCE: 1

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Thr Tyr
                20                  25                  30

Asp Met Ser Trp Val Arg Gln Thr Pro Glu Lys Arg Leu Glu Trp Val
            35                  40                  45

Ala Thr Ile Ser Ser Gly Gly Ser Tyr Thr Tyr Tyr Leu Asp Ser Val
        50                  55                  60

Lys Gly Arg Phe Thr Ile Ser Arg Asp Ser Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala
        115

<210> SEQ ID NO 2
<211> LENGTH: 113
<212> TYPE: PRT
<213> ORGANISM: Homo sapiens

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 3
<211> LENGTH: 108
<212> TYPE: PRT
<213> ORGANISM: Mus sp.
```

```
<400> SEQUENCE: 3

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Val
            20                  25                  30

Val Ala Trp Tyr Gln Gln Lys Pro Gly Gln Ser Pro Lys Thr Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Ser Tyr Pro Leu
                85                  90                  95

Thr Phe Gly Ser Gly Thr Lys Leu Glu Val Lys Arg
            100                 105

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Lys Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Glu Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ala Lys Asn Ser Leu Tyr
65                  70                  75                  80
```

```
Leu Gln Met Asn Ser Leu Arg Ala Glu Asp Thr Ala Leu Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser
        115

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser
        115

<210> SEQ ID NO 7
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaagtgaagc tggtggaatc tggcggcgga ctcgtgaagc ctggcggctc tctgagactg      60
tcttgtgccg cctctggctt cgccttctcc acctacgaca tgtcctgggt gcgacaggcc     120
cctgagaagc ggctggaatg ggtggccaca atctcctccg gcggctccta cacctactac     180
ctggactctg tgaagggccg gttcaccatc tcccgggact ccgccaagaa ctccctgtac     240
ctgcagatga acagcctgcg ggccgaggac accgccctgt actattgtgc tcccaccacc     300
gtggtgccct cgcctattg ggacagggc accctcgtga ccgtgtcctc t                351

<210> SEQ ID NO 8
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 8
gaggtgcagc tggtggaatc tggcggcgga ctcgtgaagc ctggcggctc tctgagactg       60
tcttgtgccg cctctggctt cgccttctcc acctacgaca tgtcctgggt gcgacaggcc      120
cctggcaaga gactggaatg ggtggccaca atctcctccg gcggtcctta cacctactac      180
ctggactctg tgaagggccg gttcaccatc tcccgggaca acgccaagaa ctccctgtac      240
ctgcagatga acagcctgcg ggccgaggac accgccgtgt actattgtgc tcccaccacc      300
gtggtgccct cgcctattg gggacagggc accctcgtga ccgtgtcctc t                351

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg
            100                 105

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Gln Ser Phe Met Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Asp Arg Phe Ser Gly
    50                  55                  60

Ser Gly Ser Gly Thr Glu Phe Thr Leu Thr Ile Ser Asn Val Gln Ser
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg
            100                 105
```

<210> SEQ ID NO 11
<211> LENGTH: 324
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 11

```
gacatccaga tgacccagtc ccagtccttc atgtccacct ccgtgggcga cagagtgacc      60
atcacatgca aggcctccca gaacgtgcgg accgtggtgg cctggtatca gcagaagcct     120
ggcaagtccc ccaagaccct gatctacctg gcctccaaca gacacaccgg cgtgcccgac     180
agattctccg gctctggctc tggcaccgag ttcaccctga ccatctccaa cgtgcagtcc     240
gaggacttcg ccgactactt ctgtctgcaa cactggtcct acccccctga cttcggctcc     300
ggcaccaagc tggaaatcaa gaga                                            324
```

<210> SEQ ID NO 12
<211> LENGTH: 324
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 12

```
gacatccaga tgacccagtc ccagtcctcc ctgtccacct ccgtgggcga cagagtgacc      60
atcacatgca aggcctccca gaacgtgcgg accgtggtgg cctggtatca gcagaagcct     120
ggcaagtccc ccaagaccct gatctacctg gcctccaaca gacacaccgg cgtgccctcc     180
agattctccg gctctggctc tggcaccgag ttcaccctga ccatctccaa cgtgcagccc     240
gaggacttcg ccgactactt ctgtctgcaa cactggtcct acccccctga cttcggctcc     300
ggcaccaagc tggaaatcaa gaga                                            324
```

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 13

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Val
            20                  25                  30

Val Ala Trp Tyr Gln Gln Lys Pro Gly Gln Ser Pro Lys Thr Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Ser Tyr Pro Leu
                85                  90                  95

Thr Phe Gly Ser Gly Thr Lys Leu Glu Val Lys Arg Thr Val Ala Ala
            100                 105                 110
```

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Thr Tyr
            20                  25                  30

Asp Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 15
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 16
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gaggtgcagc tggtggaatc tggcggcgga ctcgtgaagc ctggcggctc tctgagactg      60
tcttgtgccg cctctggctt cgccttctcc acctacgaca tgtcctgggt gcgacaggcc     120
cctggcaaga gactggaatg ggtggccaca atctcctccg gcggtcctta cacctactac     180
ctggactctg tgaagggccg gttcaccatc tcccgggaca cgccaagaa ctccctgtac     240 ctgcagatga acagcctgcg ggccgaggac accgccgtgt actattgtgc tcccaccacc     300

```
gtggtgccct cgcctattg gggacagggc accctcgtga ccgtgtcctc tgcttctacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggccgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341
```

<210> SEQ ID NO 17
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gacatccaga tgacccagtc ccagtcctcc ctgtccacct ccgtgggcga cagagtgacc     60
atcacatgca aggcctccca gaacgtgcgg accgtggtgg cctggtatca gcagaagcct    120
ggcaagtccc ccaagaccct gatctacctg gcctccaaca gacacaccgg cgtgccctcc    180
agattctccg gctctggctc tggcaccgag ttcaccctga ccatctccaa cgtgcagccc    240
gaggacttcg ccgactactt ctgtctgcaa cactggtcct accccctgac cttcggctcc    300
ggcaccaagc tggaaatcaa agaaccgtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctaca gcctgtcctc tacccctgacc    540 ctgtccaagg ccgactacga gaagcacaag gtgtacgcct gcgaagtgac ccaccagggc    600
ctgtctagcc ccgtgaccaa gtctttcaac cggggcgagt gc                       642

<210> SEQ ID NO 19
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 20
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gaggtgcagc tggtggaatc tggcggcgga ctcgtgaagc ctggcggctc tctgagactg      60
tcttgtgccg cctctggctt cgccttctcc acctacgaca tgtcctgggt gcgacaggcc     120
cctggcaaga gactggaatg ggtggccaca atcctcctcc gcggctccta cacctactac     180
ctggactctg tgaagggccg gttcaccatc tcccgggaca acgccaagaa ctccctgtac     240

```
ctgcagatga acagcctgcg ggccgaggac accgccgtgt actattgtgc tcccaccacc    300
gtggtgccct cgccta ttg gggacagggc accctcgtga ccgtgcctc tgcttctacc    360 aagggcccct ctgtgtttcc tctggcccc tccagcaagt ccacctctgg tggaacagcc    420
gccctgggct gcctcgtgaa ggactacttt cccgagcccg tgaccgtgtc ctggaactct    480
ggcgctctga cctctggcgt gcacaccttc cctgctgtgc tgcagtctag cggcctgtac    540
tccctgtcct ccgtcgtgac agtgccctcc agctctctgg caccagac ctacatctgc    600 aacgtgaacc acaagccctc caataccaag gtggacaagc gggtggaacc caagtcctgc    660
gacaagaccc acacctgtcc ccttgtcct gcccctgaac tgctgggcgg accttccgtg    720
ttcctgttcc ccccaaagcc caaggacacc ctgatgatct cccggacccc cgaagtgacc    780
tgcgtggtgg tggatgtgtc ccacgaggac cctgaagtga agttcaattg gtacgtggac    840
ggcgtggaag tgcacaacgc caagaccaag cctagagagg aacagtacgc ctccacctac    900
cgggtggtgt ccgtgctgac agtgctgcac caggactggc tgaacggcaa agagtacaag    960
tgcgccgtgt ccaacaaggc cctgcctgcc cccatcgaaa agaccatctc caaggccaag   1020
ggccagcccc gggaacccca ggtgtacaca ctgccccta gcaggacga gctgaccaag   1080 aaccaggtgt ccctgacctg tctcgtgaaa ggcttctacc cctccgatat cgccgtggaa   1140
tgggagtcca acggccagcc tgagaacaac tacaagacca ccccccctgt gctggactcc   1200
gacggctcat tcttcctgta cagcaagctg accgtggaca gtccggtg gcagcagggc   1260 aacgtgttct cctgctccgt gatgcacgag gccctgcaca accactacac ccagaagtcc   1320
ctgtccctga gccccggcaa a                                             1341
```

<210> SEQ ID NO 21
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly Gly
    210                 215                 220

Gly Ser Gly Gly Gly Ser Gln Val Gln Leu Val Gln Ser Gly Gly
225             230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Asp Ile Gln Met
    370                 375                 380

Thr Gln Ser Pro Ser Ser Leu Ser Ala Ser Val Gly Asp Arg Val Thr
385                 390                 395                 400

Ile Thr Cys Ser Ala Ser Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
        435                 440                 445

Asp Tyr Thr Phe Thr Ile Ser Ser Leu Gln Pro Glu Asp Ile Ala Thr
    450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
                485

<210> SEQ ID NO 22
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gacatccaga tgacccagtc ccagtcctcc ctgtccacct ccgtgggcga cagagtgacc      60
atcacatgca aggcctccca gaacgtgcgg accgtggtgg cctggtatca gcagaagcct     120

```
ggcaagtccc ccaagaccct gatctacctg cctccaaca gacacaccgg cgtgccctcc    180
agattctccg gctctggctc tggcaccgag ttcacccctga ccatctccaa cgtgcagccc   240
gaggacttcg ccgactactt ctgtctgcaa cactggtcct accccctgac cttcggctcc   300
ggcaccaagc tggaaatcaa gagaaccgtg gccgctccct ccgtgttcat cttcccacct   360
tccgacgagc agctgaagtc cggcaccgct tctgtcgtgt gcctgctgaa caacttctac   420
ccccgcgagg ccaaggtgca gtggaaggtg acaacgccc tgcagtccgg caactcccag    480
gaatccgtga ccgagcagga ctccaaggac agcacctaca gcctgtcctc taccctgacc   540
ctgtccaagg ccgactacga aagcacaag gtgtacgcct cgaagtgac ccaccagggc     600 ctgtctagcc ccgtgaccaa gtctttcaac cggggcgagt gcactagtgg cggcggagga   660
tctggcggag gtggaagcgg agggggagga tctcaggtgc agctggtgca gagcggaggc   720
ggagtggtgc agcctggcag atccctgaga ctgtcctgca aggcctccgg ctacaccttc   780
acccggtaca ccatgcactg ggtgcgacag gcccctggca agtgcctgga atggatcggc   840
tacatcaacc cctcccgggg ctacaccaac tacaaccaga gttcaagga ccggttcacc    900 atctcccggg acaactccaa gaacaccgcc tttctgcaga tggactccct gcggcctgag   960
gataccggcg tgtacttctg cgcccggtac tacgacgacc actactccct ggactactgg  1020
ggccagggaa cccctgtgac agtgtcatct ggtggcggag aagtggggg aggcggatca   1080 ggtggtggtg gatcaggcgg gggaggttca gggggtggcg gttctggggg aggggctct   1140 gatattcaga tgactcagag cccttccagc ctgagcgcct ccgtgggaga tcgcgtgaca   1200
attacctgct ctgcctcctc ctccgtgtct tacatgaatt ggtatcagca gacccctggg   1260
aaggctccta gcggtggat ctacgacacc tccaagctgg cctctggcgt gcccagcagg    1320
ttttctggct ccggcagcgg cacagattat accttcacca tcagctccct gcagccagaa   1380
gatatcgcta cctattattg tcagcagtgg tcctccaacc ctttcacctt cggctgcggc   1440
acaaagctgc agatcacaag a                                              1461
```

<210> SEQ ID NO 23
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 24
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Gln Ser Ser Leu Ser Thr Ser Val Gly
1               5                   10                  15

-continued

```
Asp Arg Val Thr Ile Thr Cys Lys Ala Ser Gln Asn Val Arg Thr Val
            20                  25                  30
Val Ala Trp Tyr Gln Gln Lys Pro Gly Lys Ser Pro Lys Thr Leu Ile
        35                  40                  45
Tyr Leu Ala Ser Asn Arg His Thr Gly Val Pro Ser Arg Phe Ser Gly
 50                  55                  60
Ser Gly Ser Gly Thr Glu Phe Thr Leu Thr Ile Ser Asn Val Gln Pro
 65                  70                  75                  80
Glu Asp Phe Ala Asp Tyr Phe Cys Leu Gln His Trp Ser Tyr Pro Leu
                85                  90                  95
Thr Phe Gly Ser Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Ser Gly Gly Gly Ser Gly Gly Gly
210                 215                 220
Gly Ser Gly Gly Gly Ser Gln Val Gln Leu Val Gln Ser Gly Gly
225                 230                 235                 240
Gly Val Val Gln Pro Gly Arg Ser Leu Arg Leu Ser Cys Lys Ala Ser
                245                 250                 255
Gly Tyr Thr Phe Thr Arg Tyr Thr Met His Trp Val Arg Gln Ala Pro
            260                 265                 270
Gly Lys Cys Leu Glu Trp Ile Gly Tyr Ile Asn Pro Ser Arg Gly Tyr
        275                 280                 285
Thr Asn Tyr Asn Gln Lys Phe Lys Asp Arg Phe Thr Ile Ser Arg Asp
290                 295                 300
Asn Ser Lys Asn Thr Ala Phe Leu Gln Met Asp Ser Leu Arg Pro Glu
305                 310                 315                 320
Asp Thr Gly Val Tyr Phe Cys Ala Arg Tyr Tyr Asp Asp His Tyr Ser
                325                 330                 335
Leu Asp Tyr Trp Gly Gln Gly Thr Pro Val Thr Val Ser Ser Gly Gly
            340                 345                 350
Gly Gly Ser Gly Gly Gly Gly Ser Gly Gly Gly Gly Ser Gly Gly Gly
        355                 360                 365
Gly Ser Gly Gly Gly Gly Ser Gly Gly Gly Ser Asp Ile Gln Met
        370                 375                 380
Thr Gln Ser Pro Ser Ser Leu Ser Ala Ser Val Gly Asp Arg Val Thr
385                 390                 395                 400
Ile Thr Cys Ser Ala Ser Ser Val Ser Tyr Met Asn Trp Tyr Gln
                405                 410                 415
Gln Thr Pro Gly Lys Ala Pro Lys Arg Trp Ile Tyr Asp Thr Ser Lys
            420                 425                 430
```

```
Leu Ala Ser Gly Val Pro Ser Arg Phe Ser Gly Ser Gly Thr
            435                 440                 445

Asp Tyr Thr Phe Thr Ile Ser Ser Leu Gln Pro Glu Asp Ile Ala Thr
450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
            485

<210> SEQ ID NO 25
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Glu Glu Ser Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 26
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln Tyr Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys Thr Ser Gly Gly Gly Ser Gly Gly
        210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
                260                 265                 270

Gly Lys Cys Leu Glu Trp Ile Gly Tyr Ile Asn Pro Ser Arg Gly Tyr
            275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Ser Gly Gly Gly Ser Gly Gly Gly
            355                 360                 365

Gly Ser Gly Gly Gly Ser Gly Gly Gly Ser Asp Ile Gln Met
370                 375                 380

Thr Gln Ser Pro Ser Ser Leu Ser Ala Ser Val Gly Asp Arg Val Thr
385                 390                 395                 400

Ile Thr Cys Ser Ala Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
                420                 425                 430

Leu Ala Ser Gly Val Pro Ser Arg Phe Ser Gly Ser Gly Ser Gly Thr
            435                 440                 445

Asp Tyr Thr Phe Thr Ile Ser Ser Leu Gln Pro Glu Asp Ile Ala Thr
    450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
                485

<210> SEQ ID NO 27
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 28
<211> LENGTH: 487
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 28

```
Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asp Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln Tyr Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Ser Gly Gly Gly Ser Gly Gly
        355                 360                 365

Gly Ser Gly Gly Gly Ser Gly Gly Gly Ser Asp Ile Gln Met
    370                 375                 380

Thr Gln Ser Pro Ser Ser Leu Ser Ala Ser Val Gly Asp Arg Val Thr
385                 390                 395                 400
```

```
Ile Thr Cys Ser Ala Ser Ser Val Ser Tyr Met Asn Trp Tyr Gln
            405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
            435                 440                 445

Asp Tyr Thr Phe Thr Ile Ser Ser Leu Gln Pro Glu Asp Ile Ala Thr
            450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
                485

<210> SEQ ID NO 29
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

-continued

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 30
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Leu
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
            245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
            275                 280                 285

Thr Asn Tyr Asn Gln Lys Phe Lys Asp Arg Phe Thr Ile Ser Arg Asp
        290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
            325                 330                 335

Leu Asp Tyr Trp Gly Gln Gly Thr Pro Val Thr Val Ser Ser Gly Gly
            340                 345                 350

Gly Gly Ser Gly Gly Gly Gly Ser Gly Gly Gly Gly Ser Gly Gly Gly
            355                 360                 365

Gly Ser Gly Gly Gly Gly Ser Gly Gly Gly Gly Ser Asp Ile Gln Met
        370                 375                 380

Thr Gln Ser Pro Ser Ser Leu Ser Ala Ser Val Gly Asp Arg Val Thr
385                 390                 395                 400

Ile Thr Cys Ser Ala Ser Ser Ser Val Ser Tyr Met Asn Trp Tyr Gln
            405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
            435                 440                 445

Asp Tyr Thr Phe Thr Ile Ser Ser Leu Gln Pro Glu Asp Ile Ala Thr
            450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
            485

<210> SEQ ID NO 31
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asp Met Ser Trp Val Arg Gln Ala Pro Gly Lys Arg Leu Glu Trp Val
            35                  40                  45

Ala Thr Ile Ser Ser Gly Gly Ser Tyr Thr Tyr Tyr Leu Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
 130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
 210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Ala Ser Thr Tyr Arg Val Val Ser
 290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
 370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 32
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln Tyr Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Ser Gly Gly Gly Ser Gly Gly
        355                 360                 365

Gly Ser Gly Gly Gly Ser Gly Gly Gly Ser Asp Ile Gln Met
        370                 375                 380

Thr Gln Ser Pro Ser Ser Leu Ser Ala Ser Val Gly Asp Arg Val Thr
385                 390                 395                 400

Ile Thr Cys Ser Ala Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
                420                 425                 430

Leu Ala Ser Gly Val Pro Ser Arg Phe Ser Gly Ser Gly Ser Gly Thr
                435                 440                 445

Asp Tyr Thr Phe Thr Ile Ser Ser Leu Gln Pro Glu Asp Ile Ala Thr
                450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
                485

<210> SEQ ID NO 33
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Arg Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

```
Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Ala Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 34
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Leu
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln Tyr Trp Ser Tyr Pro Leu
                85                  90                  95

Thr Phe Gly Ser Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Ser Gly Gly Gly Ser Gly Gly Gly
        355                 360                 365

Gly Ser Gly Gly Gly Ser Gly Gly Gly Ser Asp Ile Gln Met
    370                 375                 380

Thr Gln Ser Pro Ser Ser Leu Ser Ala Ser Val Gly Asp Arg Val Thr
385                 390                 395                 400

Ile Thr Cys Ser Ala Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
        435                 440                 445

Asp Tyr Thr Phe Thr Ile Ser Ser Leu Gln Pro Glu Asp Ile Ala Thr
    450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
                485

<210> SEQ ID NO 35
<211> LENGTH: 447
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 35

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Lys | Pro | Gly |
| 1 | | | | 5 | | | | | 10 | | | | | 15 |
| Gly | Ser | Leu | Arg | Leu | Ser | Cys | Ala | Ala | Ser | Gly | Phe | Thr | Phe | Ser |
| | | | 20 | | | | | 25 | | | | | 30 | |
| Thr | Tyr | Asp | Met | Ser | Trp | Val | Arg | Gln | Ala | Pro | Gly | Lys | Arg | Leu |
| | | | 35 | | | | | 40 | | | | | 45 | |
| Glu | Trp | Val | Ala | Thr | Ile | Ser | Ser | Gly | Gly | Ser | Tyr | Thr | Tyr | Tyr |
| | | | 50 | | | | | 55 | | | | | 60 | |
| Leu | Asp | Ser | Val | Lys | Gly | Arg | Phe | Thr | Ile | Ser | Arg | Asp | Asn | Ala |
| 65 | | | | | 70 | | | | | 75 | | | | | 80 |
| Lys | Asn | Ser | Leu | Tyr | Leu | Gln | Met | Asn | Ser | Leu | Arg | Ala | Glu | Asp |
| | | | | 85 | | | | | 90 | | | | | 95 |
| Thr | Ala | Val | Tyr | Tyr | Cys | Ala | Pro | Thr | Thr | Val | Val | Pro | Phe | Ala |
| | | | | 100 | | | | | 105 | | | | | 110 |
| Tyr | Trp | Gly | Gln | Gly | Thr | Leu | Val | Thr | Val | Ser | Ser | Ala | Ser | Thr |
| | | | | 115 | | | | | 120 | | | | | 125 |
| Lys | Gly | Pro | Ser | Val | Phe | Pro | Leu | Ala | Pro | Ser | Ser | Lys | Ser | Thr |
| | | | | 130 | | | | | 135 | | | | | 140 |
| Ser | Gly | Gly | Thr | Ala | Ala | Leu | Gly | Cys | Leu | Val | Lys | Asp | Tyr | Phe |
| 145 | | | | | 150 | | | | | 155 | | | | | 160 |
| Pro | Glu | Pro | Val | Thr | Val | Ser | Trp | Asn | Ser | Gly | Ala | Leu | Thr | Ser |
| | | | | 165 | | | | | 170 | | | | | 175 |
| Gly | Val | His | Thr | Phe | Pro | Ala | Val | Leu | Gln | Ser | Ser | Gly | Leu | Tyr |
| | | | | 180 | | | | | 185 | | | | | 190 |
| Ser | Leu | Ser | Ser | Val | Val | Thr | Val | Pro | Ser | Ser | Ser | Leu | Gly | Thr |
| | | | | 195 | | | | | 200 | | | | | 205 |
| Gln | Thr | Tyr | Ile | Cys | Asn | Val | Asn | His | Lys | Pro | Ser | Asn | Thr | Lys |
| | | | | 210 | | | | | 215 | | | | | 220 |
| Val | Asp | Lys | Arg | Val | Glu | Pro | Lys | Ser | Cys | Asp | Lys | Thr | His | Thr |
| 225 | | | | | 230 | | | | | 235 | | | | | 240 |
| Cys | Pro | Pro | Cys | Pro | Ala | Pro | Glu | Leu | Leu | Gly | Gly | Pro | Ser | Val |
| | | | | 245 | | | | | 250 | | | | | 255 |
| Phe | Leu | Phe | Pro | Pro | Lys | Pro | Lys | Asp | Thr | Leu | Met | Ile | Ser | Arg |
| | | | | 260 | | | | | 265 | | | | | 270 |
| Thr | Pro | Glu | Val | Thr | Cys | Val | Val | Val | Asp | Val | Ser | His | Glu | Asp |
| | | | | 275 | | | | | 280 | | | | | 285 |
| Pro | Glu | Val | Lys | Phe | Asn | Trp | Tyr | Val | Asp | Gly | Val | Glu | Val | His |
| | | | | 290 | | | | | 295 | | | | | 300 |
| Asn | Ala | Lys | Thr | Lys | Pro | Arg | Glu | Glu | Gln | Tyr | Ala | Ser | Thr | Tyr |
| 305 | | | | | 310 | | | | | 315 | | | | | 320 |
| Arg | Val | Val | Ser | Val | Leu | Thr | Val | Leu | His | Gln | Asp | Trp | Leu | Asn |
| | | | | 325 | | | | | 330 | | | | | 335 |
| Gly | Lys | Glu | Tyr | Lys | Cys | Ala | Val | Ser | Asn | Lys | Ala | Leu | Pro | Ala |
| | | | | 340 | | | | | 345 | | | | | 350 |
| Pro | Ile | Glu | Lys | Thr | Ile | Ser | Lys | Ala | Lys | Gly | Gln | Pro | Arg | Glu |
| | | | | 355 | | | | | 360 | | | | | 365 |
| Pro | Gln | Val | Tyr | Thr | Leu | Pro | Pro | Ser | Arg | Asp | Glu | Leu | Thr | Lys |
| 370 | | | | | 375 | | | | | 380 | | | | | |
| Asn | Gln | Val | Ser | Leu | Thr | Cys | Leu | Val | Lys | Gly | Phe | Tyr | Pro | Ser |
| 385 | | | | | 390 | | | | | 395 | | | | | 400 |
| Asp | Ile | Ala | Val | Glu | Trp | Glu | Ser | Asn | Gly | Gln | Pro | Glu | Asn | Asn |
| | | | | | | | | | | | | | | |
| Tyr | Lys | Thr | Thr | Pro | Pro | Val | Leu | Asp | Ser | | | | | |

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 36
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Gln Ser Leu Ser Thr Ser Val Gly
1               5                   10                  15

Asp Ser Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Val Ala Asp Tyr Phe Cys Leu Gln Tyr Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

```
Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
            325                 330                 335

Leu Asp Tyr Trp Gly Gln Gly Thr Pro Val Thr Val Ser Ser Gly Gly
        340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Ser Asp Ile Gln Met
    370                 375                 380

Thr Gln Ser Pro Ser Ser Leu Ser Ala Ser Val Gly Asp Arg Val Thr
385                 390                 395                 400

Ile Thr Cys Ser Ala Ser Ser Val Ser Tyr Met Asn Trp Tyr Gln
            405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
        435                 440                 445

Asp Tyr Thr Phe Thr Ile Ser Ser Leu Gln Pro Glu Asp Ile Ala Thr
        450                 455                 460

Tyr Tyr Cys Gln Gln Trp Ser Ser Asn Pro Phe Thr Phe Gly Cys Gly
465                 470                 475                 480

Thr Lys Leu Gln Ile Thr Arg
                485

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Thr Phe Ser Thr Tyr Asp Met Ser
1               5

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ile Ser Ser Gly Gly Ser Tyr Thr Tyr Tyr Leu Asp Ser Val Lys
1               5                   10                  15

Gly

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 39

Thr Thr Val Val Pro Phe Ala Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Ala Ser Gln Asn Val Arg Thr Val Val Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Ala Ser Asn Arg His Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Tyr Trp Ser Tyr Pro Leu Thr
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Ala Ser Asp Arg His Thr
1               5

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Ala Ser Gln Asn Val Arg Thr Leu Val Ala
1               5                   10

<210> SEQ ID NO 45
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln His Trp Ser Tyr Pro Leu Thr
1               5

<210> SEQ ID NO 46
<211> LENGTH: 384
<212> TYPE: PRT
<213> ORGANISM: Homo sapiens

<400> SEQUENCE: 46

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
        290                 295                 300

Leu Leu Met Trp Leu Glu Asp Gln Arg Glu Val Asn Thr Ser Gly Phe
305                 310                 315                 320
```

```
Ala Pro Ala Arg Pro Pro Gln Pro Gly Ser Thr Thr Phe Trp Ala
            325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380

<210> SEQ ID NO 47
<211> LENGTH: 330
<212> TYPE: PRT
<213> ORGANISM: Homo sapiens

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
            325                 330

<210> SEQ ID NO 48
<211> LENGTH: 326
<212> TYPE: PRT
<213> ORGANISM: Homo sapiens

<400> SEQUENCE: 48

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 49
<211> LENGTH: 377
<212> TYPE: PRT
```

<213> ORGANISM: Homo sapiens

<400> SEQUENCE: 49

```
Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Pro Cys Pro Arg
        115                 120                 125
Cys Pro Glu Pro Lys Ser Cys Asp Thr Pro Pro Cys Pro Arg Cys
    130                 135                 140
Pro Glu Pro Lys Ser Cys Asp Thr Pro Pro Pro Cys Pro Arg Cys Pro
145                 150                 155                 160
Ala Pro Glu Leu Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Gln Phe Lys Trp Tyr
        195                 200                 205
Val Asp Gly Val Glu Val His Asn Ala Lys Thr Lys Pro Arg Glu Glu
    210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
        355                 360                 365
Lys Ser Leu Ser Leu Ser Pro Gly Lys
    370                 375
```

<210> SEQ ID NO 50
<211> LENGTH: 452

<212> TYPE: PRT
<213> ORGANISM: Homo sapiens

<400> SEQUENCE: 50

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400
```

```
Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
            435                 440                 445

Gly Thr Cys Tyr
        450

<210> SEQ ID NO 51
<211> LENGTH: 327
<212> TYPE: PRT
<213> ORGANISM: Homo sapiens

<400> SEQUENCE: 51

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 52
<211> LENGTH: 353
<212> TYPE: PRT
<213> ORGANISM: Homo sapiens

<400> SEQUENCE: 52

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335
```

```
Thr His Val Asn Val Ser Val Val Met Ala Glu Val Asp Gly Thr Cys
            340                 345                 350
Tyr
```

<210> SEQ ID NO 53
<211> LENGTH: 340
<212> TYPE: PRT
<213> ORGANISM: Homo sapiens

<400> SEQUENCE: 53

```
Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340
```

<210> SEQ ID NO 54
<211> LENGTH: 106
<212> TYPE: PRT
<213> ORGANISM: Homo sapiens

<400> SEQUENCE: 54

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 55
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Trp Ser Cys Ile Ile Leu Phe Leu Val Ala Thr Ala Thr Gly
1               5                   10                  15

Glu Val Gln Leu Val Glu Ser Gly Gly Gly Leu Val Lys Pro Gly Gly
            20                  25                  30

Ser Leu Arg Leu Ser Cys Ala Ala Ser Gly Phe Ala Phe Ser Thr Tyr
        35                  40                  45

Asp Met Ser Trp Val Arg Gln Ala Pro Gly Lys Arg Leu Glu Trp Val
    50                  55                  60

Ala Thr Ile Ser Ser Gly Gly Ser Tyr Thr Tyr Tyr Leu Asp Ser Val
65                  70                  75                  80

Lys Gly Arg Phe Thr Ile Ser Arg Asp Asn Ala Lys Asn Ser Leu Tyr
                85                  90                  95

Leu Gln Met Asn Ser Leu Arg Ala Glu Asp Thr Ala Val Tyr Tyr Cys
            100                 105                 110

Ala Pro Thr Thr Val Val Pro Phe Ala Tyr Trp Gly Gln Gly Thr Leu
        115                 120                 125

Val Thr Val Ser Ser
    130

<210> SEQ ID NO 56
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 56

Met Gly Trp Ser Cys Ile Ile Leu Phe Leu Val Ala Thr Ala Thr Gly
1               5                   10                  15

Asp Ile Gln Met Thr Gln Ser Gln Ser Ser Leu Ser Thr Ser Val Gly
                20                  25                  30

Asp Arg Val Thr Ile Thr Cys Lys Ala Ser Gln Asn Val Arg Thr Val
            35                  40                  45

Val Ala Trp Tyr Gln Gln Lys Pro Gly Lys Ser Pro Lys Thr Leu Ile
    50                  55                  60

Tyr Leu Ala Ser Asn Arg His Thr Gly Val Pro Ser Arg Phe Ser Gly
65                  70                  75                  80

Ser Gly Ser Gly Thr Glu Phe Thr Leu Thr Ile Ser Asn Val Gln Pro
                85                  90                  95

Glu Asp Phe Ala Asp Tyr Phe Cys Leu Gln His Trp Ser Tyr Pro Leu
            100                 105                 110

Thr Phe Gly Ser Gly Thr Lys Leu Glu Ile Lys Arg
            115                 120

<210> SEQ ID NO 57
<211> LENGTH: 214
<212> TYPE: PRT
<213> ORGANISM: Homo sapiens

<400> SEQUENCE: 57

Ile Ser Val Glu Thr Pro Gln Asp Val Leu Arg Ala Ser Gln Gly Lys
1               5                   10                  15

Ser Val Thr Leu Pro Cys Thr Tyr His Thr Ser Thr Ser Ser Arg Glu
                20                  25                  30

Gly Leu Ile Gln Trp Asp Lys Leu Leu Leu Thr His Thr Glu Arg Val
            35                  40                  45

Val Ile Trp Pro Phe Ser Asn Lys Asn Tyr Ile His Gly Glu Leu Tyr
    50                  55                  60

Lys Asn Arg Val Ser Ile Ser Asn Asn Ala Glu Gln Ser Asp Ala Ser
65                  70                  75                  80

Ile Thr Ile Asp Gln Leu Thr Met Ala Asp Asn Gly Thr Tyr Glu Cys
                85                  90                  95

Ser Val Ser Leu Met Ser Asp Leu Glu Gly Asn Thr Lys Ser Arg Val
            100                 105                 110

Arg Leu Leu Val Leu Val Pro Pro Ser Lys Pro Glu Cys Gly Ile Glu
            115                 120                 125

Gly Glu Thr Ile Ile Gly Asn Asn Ile Gln Leu Thr Cys Gln Ser Lys
130                 135                 140

Glu Gly Ser Pro Thr Pro Gln Tyr Ser Trp Lys Arg Tyr Asn Ile Leu
145                 150                 155                 160

Asn Gln Glu Gln Pro Leu Ala Gln Pro Ala Ser Gly Gln Pro Val Ser
                165                 170                 175

Leu Lys Asn Ile Ser Thr Asp Thr Ser Gly Tyr Tyr Ile Cys Thr Ser
            180                 185                 190

Ser Asn Glu Glu Gly Thr Gln Phe Cys Asn Ile Thr Val Ala Val Arg
        195                 200                 205

Ser Pro Ser Met Asn Val
    210

<210> SEQ ID NO 58
```

```
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 59
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gaggtgcagc tggtggaatc tggcggcgga ctcgtgaagc ctggcggctc tctgagactg      60
tcttgtgccg cctctggctt cgccttctcc acctacgaca tgtcctgggt gcgacaggcc     120
cctggcaaga gactggaatg ggtggccaca atctcctccg gcggtcccta cacctactac     180
ctggactctg tgaagggccg gttcaccatc tcccgggaca cgccaagaa ctccctgtac      240 ctgcagatga acagcctgcg ggccgaggac accgccgtgt actattgtgc tccaccacc     300 gtggtgccct cgcctattg ggacagggc accctcgtga ccgtgtcctc tgcttctacc      360
aagggcccat cggtcttccc cctggcaccc tcctccaaga gcacctctgg ggcacagcg     420 gccctgggct gcctggtcaa ggactacttc cccgaaccgg tgacggtgtc gtggaactca    480
ggcgccctga ccagcggcgt gcacaccttc cggccgtcc tacagtcctc aggactctac     540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacgc cagcacgtac    900
cgtgtggtca gcgtcctcac cgtcctgcac caggactggc tgaatggcaa ggagtacaag    960
tgcaaggtct ccaacaaagc cctcccagcc ccatcgaga aaccatctc caaagccaaa     1020 gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg     1260 aacgtcttct catgctccgt gatgcatgag gctctgcaca accactacac gcagaagagc    1320
ctctccctgt ctccgggtaa a                                              1341

<210> SEQ ID NO 60
<211> LENGTH: 490
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 60

```
Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Gly Ser His Val Gln Leu Val Glu Ser Gly Gly
225                 230                 235                 240

Gly Leu Val Gln Pro Gly Gly Ser Leu Arg Leu Ser Cys Ala Ala Ser
                245                 250                 255

Gly Phe Ser Leu Thr Asp Tyr Gly Val His Trp Val Arg Gln Ala Pro
            260                 265                 270

Gly Lys Gly Leu Glu Trp Leu Gly Val Ile Trp Ser Gly Gly Gly Thr
        275                 280                 285

Ala Tyr Asn Thr Ala Leu Ile Ser Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Arg Arg Gly Ser Tyr Pro Tyr Asn Tyr
                325                 330                 335

Phe Asp Ala Trp Gly Cys Gly Thr Leu Val Thr Val Ser Ser Gly Gly
            340                 345                 350

Gly Gly Ser Gly Gly Gly Ser Gly Gly Gly Ser Gly Gly
        355                 360                 365

Gly Ser Gly Gly Gly Gly Ser Gly Gly Gly Ser Gln Ala Val Val
    370                 375                 380

Thr Gln Glu Pro Ser Leu Thr Val Ser Pro Gly Gly Thr Val Thr Leu
385                 390                 395                 400
```

```
Thr Cys Gly Ser Ser Thr Gly Ala Val Thr Ala Ser Asn Tyr Ala Asn
                405                 410                 415

Trp Val Gln Gln Lys Pro Gly Gln Cys Pro Arg Gly Leu Ile Gly Gly
            420                 425                 430

His Asn Asn Arg Pro Pro Gly Val Pro Ala Arg Phe Ser Gly Ser Leu
        435                 440                 445

Leu Gly Gly Lys Ala Ala Leu Thr Leu Leu Gly Ala Gln Pro Glu Asp
    450                 455                 460

Glu Ala Glu Tyr Tyr Cys Ala Leu Trp Tyr Ser Asp His Trp Val Ile
465                 470                 475                 480

Gly Gly Gly Thr Lys Leu Thr Val Leu Gly
                485                 490

<210> SEQ ID NO 61
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gacatccaga tgacccagtc ccagtcctcc ctgtccacct ccgtgggcga cagagtgacc      60
atcacatgca aggcctccca gaacgtgcgg accgtggtgg cctggtatca gcagaagcct     120
ggcaagtccc ccaagaccct gatctacctg gcctccaaca gacacaccgg cgtgccctcc     180
agattctccg gctctggctc tggcaccgag ttcaccctga ccatctccaa cgtgcagccc     240
gaggacttcg ccgactactt ctgtctgcaa cactggtcct accccctgac cttcggctcc     300
ggcaccaagc tggaaatcaa agaaccgtg gccgctccct ccgtgttcat cttcccacct     360
tccgacgagc agctgaagtc cggcaccgct tctgtcgtgt gcctgctgaa caacttctac     420
ccccgcgagg ccaaggtgca gtggaaggtg acaacgccc tgcagtccgg caactcccag     480
gaatccgtga ccgagcagga ctccaaggac agcacctaca gcctgtcctc taccctgacc     540
ctgtccaagg ccgactacga aagcacaag gtgtacgcct gcgaagtgac ccaccagggc     600
ctgtctagcc ccgtgaccaa gtctttcaac cggggcgagt gcactagtgg cggcggagga     660
tctggcggag gtggaagtgg gggaggcgga tctcatgtgc agctggtgga aagcggaggc     720
ggcctggtgc agcctggggg atctctgaga ctgtcttgtg ccgccagcgg cttctccctg     780
accgattatg gcgtgcactg ggtgcgacag gcccctggca aaggactgga atggctggga     840
gtgatttgga gtggcggagg caccgcctac aacaccgccc tgatctcccg gttcaccatc     900
agccgggaca actccaagaa cacccctgtac ctgcagatga actccctgcg ggccgaggac     960
accgctgtgt actactgcgc cagacggggc tcctaccccct acaactactt cgacgcttgg    1020
ggctgcggca ccctcgtgac agtgtctagc ggagggggag gttctggggg cggaggttca    1080
ggtggtggtg gttccggggg tggtggctct ggtggcggtg gttctggcgg tggcggatct    1140
caggctgtcg tgacccagga acccagcctg actgtgtctc ctggcggaac cgtgaccctg    1200
acctgcggat cttctaccgg cgctgtgacc gccagcaact acgccaattg ggtgcagcag    1260
aaacctggac agtgccctag aggcctgatc ggcggccaca acaacagacc tccaggcgtg    1320
ccagcccggt tctctggatc tctgctgggc ggaaaggccg ctctgacact gctgggtgct    1380
cagcctgagg acgaggccga gtactactgt gccctgtggt actccgacca ctgggtcatc    1440
ggaggcggga ccaagctgac cgtgctggga                                     1470
```

<210> SEQ ID NO 62
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 63
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Gln Ser Ser Leu Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Gly Ser His Val Lys Leu Gln Glu Ser Gly Pro
225                 230                 235                 240

Gly Leu Val Gln Pro Ser Gln Ser Leu Ser Leu Thr Cys Thr Val Ser
                245                 250                 255
```

-continued

```
Gly Phe Ser Leu Thr Asp Tyr Gly Val His Trp Val Arg Gln Ser Pro
            260                 265                 270
Gly Lys Gly Leu Glu Trp Leu Gly Val Ile Trp Ser Gly Gly Gly Thr
        275                 280                 285
Ala Tyr Asn Thr Ala Leu Ile Ser Arg Leu Asn Ile Tyr Arg Asp Asn
    290                 295                 300
Ser Lys Asn Gln Val Phe Leu Glu Met Asn Ser Leu Gln Ala Glu Asp
305                 310                 315                 320
Thr Ala Met Tyr Tyr Cys Ala Arg Arg Gly Ser Tyr Pro Tyr Asn Tyr
                325                 330                 335
Phe Asp Ala Trp Gly Cys Gly Thr Thr Val Thr Val Ser Ser Gly Gly
            340                 345                 350
Gly Gly Ser Gly Gly Gly Gly Ser Gly Gly Gly Gly Ser Gly Gly Gly
        355                 360                 365
Gly Ser Gly Gly Gly Gly Ser Gly Gly Gly Gly Ser Gln Ala Val Val
    370                 375                 380
Ile Gln Glu Ser Ala Leu Thr Thr Pro Pro Gly Glu Thr Val Thr Leu
385                 390                 395                 400
Thr Cys Gly Ser Ser Thr Gly Ala Val Thr Ala Ser Asn Tyr Ala Asn
                405                 410                 415
Trp Val Gln Glu Lys Pro Asp His Cys Phe Thr Gly Leu Ile Gly
            420                 425                 430
His Asn Asn Arg Pro Pro Gly Val Pro Ala Arg Phe Ser Gly Ser Leu
        435                 440                 445
Ile Gly Asp Lys Ala Ala Leu Thr Ile Ala Gly Thr Gln Thr Glu Asp
    450                 455                 460
Glu Ala Ile Tyr Phe Cys Ala Leu Trp Tyr Ser Asp His Trp Val Ile
465                 470                 475                 480
Gly Gly Gly Thr Arg Leu Thr Val Leu Gly
                485                 490

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly Ser
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 65

His His His His His His
1               5

<210> SEQ ID NO 66
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Gly Gly Gly Gly Ser Gly Gly Gly Gly Ser Gly Gly Gly Gly Ser
1               5                   10                  15

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Gly Gly Gly Ser Gly Gly Gly Gly Ser Gly Gly Gly Gly Ser Gly
1               5                   10                  15

Gly Gly Gly Ser
            20

<210> SEQ ID NO 68
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(11)
<223> OTHER INFORMATION: a, c, t, g, unknown or other

<400> SEQUENCE: 68
gctcttcnnn n                                                            11

<210> SEQ ID NO 69
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 69
nnnngaagag c                                                            11

<210> SEQ ID NO 70
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45
```

```
Ala Thr Ile Ser Ser Gly Gly Ser Tyr Thr Tyr Tyr Leu Asp Ser Val
            50                  55                  60

Lys Gly Arg Phe Thr Ile Ser Arg Asp Ser Ser Lys Asn Thr Leu Tyr
 65                  70                  75                  80

Leu Gln Met Asn Ser Leu Gln Ala Glu Asp Ser Ala Ile Tyr Tyr Cys
                 85                  90                  95

Ala Pro Thr Thr Val Val Pro Phe Ala Tyr Trp Gly Gln Gly Thr Leu
            100                 105                 110

Val Thr Val Ser Ser
            115

<210> SEQ ID NO 71
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Lys Leu Val Glu Ser Gly Gly Gly Leu Val Lys Pro Gly Gly
 1               5                  10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Glu Lys Arg Leu Glu Trp Val
            35                  40                  45

Ala Thr Ile Ser Ser Gly Gly Ser Tyr Thr Tyr Tyr Leu Asp Ser Val
            50                  55                  60

Lys Gly Arg Phe Thr Ile Ser Arg Asp Ser Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Pro Thr Thr Val Val Pro Phe Ala Tyr Trp Gly Gln Gly Thr Leu
            100                 105                 110

Val Thr Val Ser Ser
            115

<210> SEQ ID NO 72
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Arg Leu Glu Trp Val
            35                  40                  45

Ala Thr Ile Ser Ser Gly Gly Ser Tyr Thr Tyr Tyr Leu Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

Ala Pro Thr Thr Val Val Pro Phe Ala Tyr Trp Gly Gln Gly Thr Leu
            100                 105                 110

Val Thr Val Ser Ser
        115

<210> SEQ ID NO 73
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Gln Met Thr Gln Ser Pro Ser Ser Leu Ser Val Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Leu Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln His Trp Ser Tyr Pro Leu
                85                  90                  95

Thr Phe Gly Gln Gly Thr Lys Val Glu Val Lys Arg
            100                 105

<210> SEQ ID NO 74
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Gln Ser Phe Met Ser Thr Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Lys Ser Pro Lys Thr Leu Ile
        35                  40                  45

Tyr Leu Ala Ser Asn Arg His Thr Gly Val Pro Asp Arg Phe Ser Gly
    50                  55                  60

Ser Gly Ser Gly Thr Glu Phe Thr Leu Thr Ile Ser Asn Val Gln Ser
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg
            100                 105

<210> SEQ ID NO 75
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 75

Asp Ile Gln Met Thr Gln Ser Gln Ser Ser Leu Ser Ser Val Gly
1               5                   10                  15

Asp Arg Val Thr Ile Thr Cys Lys Ala Ser Gln Asn Val Arg Thr Val
                20                  25                  30

Val Ala Trp Tyr Gln Gln Lys Pro Gly Lys Ser Pro Lys Thr Leu Ile
            35                  40                  45

Tyr Leu Ala Ser Asn Arg His Thr Gly Val Pro Ser Arg Phe Ser Gly
        50                  55                  60

Ser Gly Ser Gly Thr Glu Phe Thr Leu Thr Ile Ser Asn Val Gln Pro
65                  70                  75                  80

Glu Asp Phe Ala Asp Tyr Phe Cys Leu Gln His Trp Ser Tyr Pro Leu
                85                  90                  95

Thr Phe Gly Ser Gly Thr Lys Leu Glu Ile Lys Arg
                100                 105

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 76

Gly Gly Gly Gly Ser
1               5
```

A33 ANTIBODY COMPOSITIONS AND METHODS OF USING THE SAME IN RADIOIMMUNOTHERAPY

CROSS-REFERENCE TO RELATED APPLICATIONS

This application is a National Stage Application of PCT/US2018/052253, filed Sep. 21, 2018, which claims the benefit of and priority to U.S. Provisional Patent Application No. 62/562,373, filed Sep. 23, 2017, and also to U.S. Provisional Patent Application No. 62/562,374, filed Sep. 23, 2017, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 17, 2018, is named 115872-0455_SL.txt and is 157,991 bytes in size.

TECHNICAL FIELD

The present technology relates generally to the preparation of immunoglobulin-related compositions (e.g., antibodies or antigen binding fragments thereof) that specifically bind A33 protein and uses of the same. In particular, the present technology relates to the preparation of A33 neutralizing antibodies and their use in detecting and treating A33 associated cancers.

BACKGROUND

The following description of the background of the present technology is provided simply as an aid in understanding the present technology and is not admitted to describe or constitute prior art to the present technology.

Colorectal cancers (CRCs) constitute the 3$^{rd}$ leading cause of cancer death in the United States (Siegel R L, Miller K D, Jemal A, *CA: A Cancer Journal for Clinicians* 67:7-30 (2017)) and account for 10% of all cancers in men and 9.2% in women worldwide (Ferlay J, Soerjomataram I, Dikshit R, et al., *International Journal of Cancer* 136:E359-E386 (2015)). Although there has been steady yearly 3% decline in the incidence from 2004 to 2013, 135,000 new cases are expected in 2017 in the United States alone. Although localized and regional diseases can be curable, the prognosis of metastatic CRCs (mCRCs) is poor, with a 5-year survival rate of only 14% (Siegel R L, Miller K D, Jemal A, *CA: A Cancer Journal for Clinicians* 67:7-30 (2017)).

Standard treatment for mCRC consists of chemotherapy in combination with monoclonal antibodies that block tumor signaling or angiogenesis. Currently four monoclonal antibody drugs have been FDA approved for CRC treatment: bevacizumab and ramucirumab target the VEGF-VEGFR angiogenesis pathway, while cetuximab and panitumumab target the EGFR pathway. However, cetuximab and panitumumab do not provide clinical benefits for mCRC with RAS mutations (Van Cutsem E, Cervantes A, Adam R, et al., *Annals of Oncology* 27:1386-1422 (2016)), which are found in around 40% of all mCRC (Bencsikova B, Bortlicek Z, Halamkova J, et al., *BMC Gastroenterology* 15:37 (2015)). Moreover, improvement in survival with these antibodies is generally modest (Peeters M et al., *Journal of Clinical Oncology* 28:4706-4713 (2010); Cutsem E V et al., *Journal of Clinical Oncology* 29:2011-2019 (2011); Saltz L B et al., *Journal of Clinical Oncology* 26:2013-2019 (2008)) and can be associated with severe side effects. The benefits of immune checkpoint inhibitors (ICI) have been restricted to subsets of CRC patients with microsatellite instability (MSI). However, the majority of patients with mCRC are microsatellite stable (MSS) and are thus not expected to benefit from ICI monotherapy. Thus far, the use of antibodies to target toxins to tumors, e.g., radioimmunotherapy (RIT) with directly conjugated antibodies, has been met with limited success due in part to suboptimal tumor dose and therapeutic index (TI). Further, because of normal tissue bystander toxicity, dose escalation is not feasible and therefore such therapy results in limited anti-tumor effect.

SUMMARY OF THE PRESENT TECHNOLOGY

In one aspect, the present disclosure provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR1 sequence of FTFSTYDMS (SEQ ID NO: 37), a $V_H$-CDR2 sequence of TISSGG-SYTYYLDSVKG (SEQ ID NO: 38), and a $V_H$-CDR3 sequence of TTVVPFAY (SEQ ID NO: 39); and/or (b) the $V_L$ comprises a $V_L$-CDR1 sequence, a $V_L$-CDR2 sequence, and a $V_L$-CDR3 sequence selected from the group consisting of: KASQNVRTVVA (SEQ ID NO: 40), LASNRHT (SEQ ID NO: 41), and QYWSYPLT (SEQ ID NO: 42); KASQNVRTVVA (SEQ ID NO: 40), LASDRHT (SEQ ID NO: 43), and QYWSYPLT (SEQ ID NO: 42); KASQNVRTLVA (SEQ ID NO: 44), LASNRHT (SEQ ID NO: 41), and QHWSYPLT (SEQ ID NO: 45); and KASQNVRTLVA (SEQ ID NO: 44), LASNRHT (SEQ ID NO: 41), and QYWSYPLT (SEQ ID NO: 42).

The antibody may further comprise an Fc domain of an isotype selected from the group consisting of IgG1, IgG2, IgG3, IgG4, IgA1, IgA2, IgM, IgD, and IgE. In some embodiments, the antibody comprises an IgG1 constant region comprising one or more amino acid substitutions selected from the group consisting of N297A and K322A. Additionally or alternatively, in some embodiments, the antibody comprises an IgG4 constant region comprising a S228P mutation. In certain embodiments, the antigen binding fragment is selected from the group consisting of Fab, F(ab')$_2$, Fab', scF$_v$, and F$_v$. In some embodiments, the antibody is a monoclonal antibody, chimeric antibody, humanized antibody, or a bispecific antibody. In certain embodiments, the antibody or antigen binding fragment binds to an epitope of A33 protein comprising at least five to eight consecutive amino acid residues of SEQ ID NO: 57. In some embodiments, the epitope is a conformational epitope.

In another aspect, the present disclosure provides an antibody comprising a heavy chain (HC) amino acid sequence comprising SEQ ID NO: 5, SEQ ID NO: 6, SEQ ID NO: 15, SEQ ID NO: 19, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 58, SEQ ID NO: 62, or a variant thereof having one or more conservative amino acid substitutions, and/or a light chain (LC) amino acid sequence comprising SEQ ID NO: 9, SEQ ID NO: 10, SEQ ID NO: 17, SEQ ID NO: 21, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 60, SEQ ID NO: 63, or a variant thereof having one or more conservative amino acid substitutions. In certain embodiments, the antibody comprises a HC amino acid sequence and a LC amino acid sequence selected from the group consisting of: SEQ ID NO: 5 and SEQ ID NO: 9 (3A3-H1/L1); SEQ ID NO: 5 and SEQ ID NO: 10 (3A3-H1/L2); SEQ ID NO: 6 and SEQ ID NO: 9 (3A3-H2/L1); SEQ ID NO: 6 and SEQ ID NO: 10 (3A3-H2/L2); SEQ ID NO: 15 and SEQ ID NO: 17 (huA33-IgG1 (H2L2)); SEQ ID NO: 19 and SEQ ID NO: 21 (huA33-BsAb); SEQ ID NO: 23 and SEQ ID NO: 24 (clone 31); SEQ ID NO: 25 and SEQ ID NO: 26 (clone 32); SEQ ID NO: 27 and SEQ ID NO: 28 (clone 48); SEQ ID NO: 29 and SEQ ID NO: 30 (clone 49); SEQ ID NO: 31 and SEQ ID NO: 32 (clone 53); SEQ ID NO: 33 and SEQ ID NO: 34 (clone 56); SEQ ID NO: 35 and SEQ ID NO: 36 (clone 57); SEQ ID NO: 58 and SEQ ID NO: 60 (huA33-huC825); and SEQ ID NO: 62 and SEQ ID NO: 63 (huA33-mC825), respectively.

In one aspect, the present disclosure provides an antibody comprising (a) a light chain immunoglobulin variable domain sequence that is at least 80%, at least 85%, at least 90%, at least 95%, or at least 99% identical to the light chain immunoglobulin variable domain sequence present in any one of SEQ ID NOs: 9, 10, 17, 21, 24, 26, 28, 30, 32, 34, 36, 60, or 63; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 5, 6, 15, 19, 23, 25, 27, 29, 31, 33, 35, 58 or 62.

In another aspect, the present disclosure provides an antibody comprising (a) a LC sequence that is at least 80%, at least 85%, at least 90%, at least 95%, or at least 99% identical to the LC sequence present in any one of SEQ ID NOs: 9, 10, 17, 21, 24, 26, 28, 30, 32, 34, 36, 60, or 63; and/or (b) a HC sequence that is at least 80%, at least 85%, at least 90%, at least 95%, or at least 99% identical to the HC sequence present in any one of SEQ ID NOs: 5, 6, 15, 19, 23, 25, 27, 29, 31, 33, 35, 58 or 62.

In any of the above embodiments, the antibody is a chimeric antibody, a humanized antibody, or a bispecific antibody. Additionally or alternatively, in some embodiments, the antibody comprises an IgG1 constant region comprising one or more amino acid substitutions selected from the group consisting of N297A and K322A. In certain embodiments, the antibody of the present technology comprises an IgG4 constant region comprising a S228P mutation. In any of the above embodiments, the antibody binds to an epitope of A33 protein comprising at least five to eight consecutive amino acid residues of SEQ ID NO: 57. In some embodiments, the epitope is a conformational epitope. Additionally or alternatively, in some embodiments, the antibody of the present technology lacks α-1,6-fucose modifications.

In one aspect, the present disclosure provides a recombinant nucleic acid sequence encoding any of the antibodies described herein. In some embodiments, the recombinant nucleic acid sequence selected from the group consisting of: SEQ ID NOs: 7, 8, 11, 12, 16, 18, 20, 22, 59 and 61.

In another aspect, the present disclosure provides a host cell or vector comprising any of the recombinant nucleic acid sequences disclosed herein.

In one aspect, the present disclosure provides a composition comprising an antibody or antigen binding fragment of the present technology and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In some embodiments of the bispecific antibody of the present technology, the bispecific antibody binds to T cells, B-cells, myeloid cells, plasma cells, or mast-cells. Additionally or alternatively, in some embodiments, the bispecific antibody binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten. The small molecule DOTA hapten may be selected from the group consisting of DOTA, DOTA-Bn, DOTA-desferrioxamine, DOTA-Phe-Lys(HSG)-D-Tyr-Lys(HSG)-NH$_2$, Ac-Lys(HSG)D-Tyr-Lys(HSG)-Lys(Tscg-Cys)-NH$_2$, DOTA-D-Asp-D-Lys(HSG)-D-Asp-D-Lys(HSG)-NH$_2$; DOTA-D-Glu-D-Lys(HSG)-D-Glu-D-Lys(HSG)-NH$_2$, DOTA-D-Tyr-D-Lys(HSG)-D-Glu-D-Lys(HSG)-NH$_2$, DOTA-D-Ala-D-Lys(HSG)-D-Glu-D-Lys(HSG)-NH$_2$, DOTA-D-Phe-D-Lys(HSG)-D-Tyr-D-Lys(HSG)-NH$_2$, Ac-D-Phe-D-Lys(DOTA)-D-Tyr-D-Lys(DOTA)-NH$_2$, Ac-D-Phe-D-Lys(DTPA)-D-Tyr-D-Lys(DTPA)-NH$_2$, Ac-D-Phe-D-Lys(Bz-DTPA)-D-Tyr-D-Lys(Bz-DTPA)-NH$_2$, Ac-D-Lys(HSG)-D-Tyr-D-Lys(HSG)-D-Lys(Tscg-Cys)-NH$_2$, DOTA-D-Phe-D-Lys(HSG)-D-Tyr-D-Lys(HSG)-D-Lys(Tscg-Cys)-NH$_2$, (Tscg-Cys)-D-Phe-D-Lys(HSG)-D-Tyr-D-Lys(HSG)-D-Lys(DOTA)-NH$_2$, Tscg-D-Cys-D-Glu-D-Lys(HSG)-D-Glu-D-Lys(HSG)-NH$_2$, (Tscg-Cys)-D-Glu-D-Lys(HSG)-D-Gu-D-Lys(HSG)-NH$_2$, Ac-D-Cys-D-Lys(DOTA)-D-Tyr-D-Ala-D-Lys(DOTA)-D-Cys-NH$_2$, Ac-D-Cys-D-Lys(DTPA)-D-Tyr-D-Lys(DTPA)-NH$_2$, Ac-D-Lys(DTPA)-D-Tyr-D-Lys(DTPA)-D-Lys(Tscg-Cys)-NH$_2$, and Ac-D-Lys(DOTA)-D-Tyr-D-Lys(DOTA)-D-Lys(Tscg-Cys)-NH$_2$.

In another aspect, the present disclosure provides a method for treating an A33 associated cancer in a subject in need thereof, comprising administering to the subject an effective amount of any one of the antibodies disclosed herein. In certain embodiments, the antibody comprises a HC amino acid sequence and a LC amino acid sequence selected from the group consisting of: SEQ ID NO: 5 and SEQ ID NO: 9 (3A3-H1/L1); SEQ ID NO: 5 and SEQ ID NO: 10 (3A3-H1/L2); SEQ ID NO: 6 and SEQ ID NO: 9 (3A3-H2/L1); SEQ ID NO: 6 and SEQ ID NO: 10 (3A3-H2/L2); SEQ ID NO: 15 and SEQ ID NO: 17 (huA33-IgG1 (H2L2)); SEQ ID NO: 19 and SEQ ID NO: 21 (huA33-BsAb); SEQ ID NO: 23 and SEQ ID NO: 24 (clone 31); SEQ ID NO: 25 and SEQ ID NO: 26 (clone 32); SEQ ID NO: 27 and SEQ ID NO: 28 (clone 48); SEQ ID NO: 29 and SEQ ID NO: 30 (clone 49); SEQ ID NO: 31 and SEQ ID NO: 32 (clone 53); SEQ ID NO: 33 and SEQ ID NO: 34 (clone 56); SEQ ID NO: 35 and SEQ ID NO: 36 (clone 57), SEQ ID NO: 58 and SEQ ID NO: 60 (huA33-huC825); and SEQ ID NO: 62 and SEQ ID NO: 63 (huA33-mC825), respectively, wherein the antibody specifically binds to and neutralizes A33 activity.

In some embodiments, the A33 associated cancer is colorectal cancer, Pseudomyxoma peritonei, appendiceal cancer, pancreatic cancer, or gastric cancer. The A33 associated cancer may be colorectal cancer with a MSI genotype or a MSS genotype. Additionally or alternatively, in some embodiments, the colorectal cancer is associated with a KRAS G12D mutation or a p53 mutation.

Additionally or alternatively, in some embodiments of the method, the antibody is administered to the subject separately, sequentially or simultaneously with an additional therapeutic agent. Examples of additional therapeutic agents include one or more of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents.

In another aspect, the present disclosure provides a method for detecting a tumor in a subject in vivo comprising (a) administering to the subject an effective amount of an antibody of the present technology, wherein the antibody is configured to localize to a tumor expressing A33 and is labeled with a radioisotope; and (b) detecting the presence of a tumor in the subject by detecting radioactive levels emitted by the antibody that are higher than a reference value. In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}Y$, $^{90}Y$, $^{89}Sr$, $^{165}Dy$, $^{186}Re$, $^{188}Re$, $^{177}Lu$, and $^{67}Cu$. In some embodiments of the method, nonspecific FcR-dependent binding in normal tissues is eliminated or reduced (e.g., via N297A mutation in Fc region, which results in aglycosylation).

Also disclosed herein are kits for the detection and/or treatment of A33 associated cancers, comprising at least one immunoglobulin-related composition of the present technology (e.g., any antibody or antigen binding fragment described herein), or a functional variant (e.g., substitutional variant) thereof and instructions for use. In certain embodiments, the immunoglobulin-related composition is coupled to one or more detectable labels. In one embodiment, the one or more detectable labels comprise a radioactive label, a fluorescent label, or a chromogenic label.

Additionally or alternatively, in some embodiments, the kit further comprises a secondary antibody that specifically binds to an anti-A33 immunoglobulin-related composition described herein. In some embodiments, the secondary antibody is coupled to at least one detectable label selected from the group consisting of a radioactive label, a fluorescent label, or a chromogenic label.

In one aspect, the present disclosure provides a method for detecting solid tumors in a subject in need thereof comprising (a) administering to the subject an effective amount of a complex comprising a radiolabeled DOTA hapten and a bispecific antibody of the present technology that binds to the radiolabeled DOTA hapten and an A33 antigen, wherein the complex is configured to localize to a solid tumor expressing the A33 antigen recognized by the bispecific antibody of the complex; and (b) detecting the presence of solid tumors in the subject by detecting radioactive levels emitted by the complex that are higher than a reference value.

In another aspect, the present disclosure provides a method for selecting a subject for pretargeted radioimmunotherapy comprising (a) administering to the subject an effective amount of a complex comprising a radiolabeled DOTA hapten and a bispecific antibody of the present technology that binds to the radiolabeled DOTA hapten and an A33 antigen, wherein the complex is configured to localize to a solid tumor expressing the A33 antigen recognized by the bispecific antibody of the complex; (b) detecting radioactive levels emitted by the complex; and (c) selecting the subject for pretargeted radioimmunotherapy when the radioactive levels emitted by the complex are higher than a reference value.

In one aspect, the present disclosure provides a method for increasing tumor sensitivity to radiation therapy in a subject diagnosed with an A33-positive cancer comprising administering to the subject an effective amount of a complex comprising a radiolabeled-DOTA hapten and a bispecific antibody of the present technology that recognizes and binds to the radiolabeled-DOTA hapten and an A33 antigen target, wherein the complex is configured to localize to a tumor expressing the A33 antigen target recognized by the bispecific antibody of the complex.

In another aspect, the present disclosure provides a method for treating cancer in a subject in need thereof comprising administering to the subject an effective amount of a complex comprising a radiolabeled-DOTA hapten and a bispecific antibody of the present technology that recognizes and binds to the radiolabeled-DOTA hapten and an A33 antigen target, wherein the complex is configured to localize to a tumor expressing the A33 antigen target recognized by the bispecific antibody of the complex.

In any of the above embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments of the methods disclosed herein, the subject is human. Additionally or alternatively, in any of the above embodiments of the methods disclosed herein, the radiolabeled-DOTA hapten comprises $^{213}Bi$, $^{211}At$, $^{225}Ac$, $^{152}Dy$, $^{212}Bi$, $^{223}Ra$, $^{219}R$, $^{215}Po$, $^{211}Bi$, $^{221}Fr$, $^{217}At$, $^{255}Fm$, $^{86}Y$, $^{90}Y$, $^{89}Sr$, $^{165}Dy$, $^{186}Re$, $^{188}Re$, $^{177}Lu$, $^{67}Cu$, $^{111}In$, $^{67}Ga$, $^{51}Cr$, $^{58}Co$, $^{99m}Tc$, $^{103m}Rh$, $^{195m}Pt$ $^{119}Sb$, $^{161}Ho$, $^{189}OS$, $^{192}Ir$, $^{201}Tl$, $^{203}Pb$, $^{68}Ga$, $^{227}Th$, or $^{64}Cu$, and optionally comprises an alpha particle-emitting isotope, a beta particle-emitting isotope, or an Auger-emitter.

In one aspect, the present disclosure provides a method for increasing tumor sensitivity to radiation therapy in a subject diagnosed with an A33-positive cancer comprising (a) administering an effective amount of an anti-DOTA bispecific antibody of the present technology to the subject, wherein the anti-DOTA bispecific antibody is configured to localize to a tumor expressing an A33 antigen target; and (b) administering an effective amount of a radiolabeled-DOTA hapten to the subject, wherein the radiolabeled-DOTA hapten is configured to bind to the anti-DOTA bispecific antibody. In another aspect, the present disclosure provides a method for treating cancer in a subject in need thereof comprising (a) administering an effective amount of an anti-DOTA bispecific antibody of the present technology to the subject, wherein the anti-DOTA bispecific antibody is configured to localize to a tumor expressing an A33 antigen target; and (b) administering an effective amount of a radiolabeled-DOTA hapten to the subject, wherein the radiolabeled-DOTA hapten is configured to bind to the anti-DOTA bispecific antibody. In some embodiments, the methods of the present technology further comprise administering an effective amount of a clearing agent to the subject prior to administration of the radiolabeled-DOTA hapten.

Additionally or alternatively, in any of the above embodiments of the methods disclosed herein, the radiolabeled-DOTA hapten comprises $^{213}Bi$, $^{211}At$, $^{225}Ac$, $^{152}Dy$, $^{212}Bi$, $^{223}Ra$, $^{219}Rn$, $^{215}Po$, $^{211}Bi$, $^{221}Fr$, $^{217}At$, $^{255}Fm$, $^{86}Y$, $^{90}Y$, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$OS, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter. In any of the above embodiments of the methods disclosed herein, the subject is human.

BRIEF DESCRIPTION OF THE DRAWINGS

FIG. 1(A) shows the design and construction of humanized A33-bispecific antibody (huA33-BsAb). FIG. 1(B) shows the accelerated stability test of purified huA33-BsAb at 37° C. over 4 weeks. FIG. 1(C) shows the Surface Plasmon Resonance (SPR) analysis of huA33-BsAb at 25° C. and 37° C. Data were fit to 1:1 binding model. FIG. 1(D) shows the FACS staining of different tumor cell lines and activated T cells. Mean fluorescence intensity (MFI) values were geometric means.

FIG. 2(A) shows the activation of CD25 and CD69 markers in T cells at 24 hours post incubation with Colo205 cells and different antibodies. FIG. 2(B) shows the quantification of dividing cells based on CFSE dye dilution at 96 hours post incubation with Colo205 cells and different antibodies. FIG. 2(C) shows representative images for FIG. 2(B). FIG. 2(D) shows the staining of CD45RO at 96 hours post incubation with Colo205 cells and huA33-BsAb in an independent experiment. FIG. 2(E) shows the in vivo activation and proliferation of T cells by huA33-BsAb. Briefly, CFSE-labeled peripheral blood mononuclear cells (PBMCs) were mixed with Colo205 cells and the mixture was implanted subcutaneously onto DKO mice. HuA33-BsAb was injected intravenously the next day and the tumors were isolated after another 4 days and analyzed by FACS.

FIG. 4(A) shows the cytotoxicity elicited by huA33-BsAb against different target tumor cell lines and control cells. Activated T cells were used as effector cells at an effector to target ratio (E:T) of 10:1. Cells were incubated for 16 hours before obtaining readings. FIG. 4(B) shows the cytotoxicity induced by huA33-BsAb against Colo205 cells. Sorted fresh T cell subsets were used as effector cells (E:T=5:1). Cells were incubated for 48 hours before obtaining readings. EC50 for CD4 memory T cells was 25 pM.

FIG. 6(A) shows the growth of s.c. LS174T tumors in treatment group and control groups. Tumor sizes were assessed by volume (p=0.0133 for tumor+scPBMC versus tumor+scPBMC+huA33-BsAb; p=0.006 for tumor only versus tumor+scPBMC+huA33-BsAb). FIG. 6(B) shows the i.p. LS174T tumor growth in treatment group and control groups (top) (p=0.0125 for tumor+ATC versus tumor+ATC+ huA33-BsAb; p=0.0026 for tumor only versus tumor+ATC+ huA33-BsAb) and survival of mice in treatment group and control groups (bottom). FIG. 6(C) shows luminescence images of abdominal LS174T tumors in different groups. Tumor only group had one mouse (#4) that did not take the tumor after 21 days and was excluded from analysis.

FIG. 8(A) shows the growth of s.c. SNU16 tumors in different groups. FIG. 8(B) shows the engraftment of human cells from mice blood in FIG. 8(A).

FIG. 10 shows the results of FACS analysis of various cell lines stained with huA33-BsAb.

FIG. 11(A) shows the upregulation of PD-1 on T cells activated by huA33-BsAb in the presence of Colo205 cells after 24 hours (left) and 96 hours (right). FIG. 11(B) shows the absence of T cell division after incubating with SKMEL5 in the presence of huA33-BsAb after 96 hours. FIG. 11(C) shows the activation of T cell division by huA33-BsAb in the presence of LS174T cells. FIGS. 11(B) and 11(C) used the same preparation of T cells.

FIG. 12(A): gated on CD4(+) T cells; FIG. 12(B): gated on CD8(+) T cells.

FIG. 13 discloses SEQ ID NOS 68-69, respectively, in order of appearance.

FIG. 14 shows the amino acid sequences of the VH and VL domains of the murine A33 antibody and their corresponding homologous human sequences (SEQ ID NOs: 1-4). The CDR1, CDR2, and CDR3 regions of the $V_H$ and VL domains of the murine A33 antibody are indicated by the underlined boldface font.

FIG. 15 shows the amino acid sequences of the humanized heavy chains of huA33-H1 (3A3-H1) (SEQ ID NO: 5) and huA33-H2 (3A3-H2) (SEQ ID NO: 6). The CDR1, CDR2, and CDR3 regions of 3A3-H1 and 3A3-H2 are indicated by the underlined boldface font.

FIG. 16 shows the cDNA sequences of the humanized heavy chains of huA33-H1 (3A3-H1) (SEQ ID NO: 7) and huA33-H2 (3A3-H2) (SEQ ID NO: 8).

FIG. 17 shows the amino acid sequences of the humanized light chains of huA33-L1 (3A3-L1) (SEQ ID NO: 9) and huA33-L2 (3A3-L2) (SEQ ID NO: 10). The CDR1, CDR2, and CDR3 regions of 3A3-L1 and 3A3-L2 are indicated by the underlined boldface font.

FIG. 18 shows the cDNA sequences of the humanized light chains of huA33-L1 (3A3-L1) (SEQ ID NO: 11) and huA33-L2 (3A3-L2) (SEQ ID NO: 12).

FIG. 20 shows the binding kinetics of the humanized IgG variants of huA33 assayed on GPA33 recombinant protein using SPR (BIACORE®-T100). All four versions retained the high binding affinity of chimeric A33 (chA33).

FIG. 22 shows the binding kinetics of the original humanized hA33 (in hA33-mC825 bispecific format as described in Cheal et al, *Eur. J. Nucl. Med. Mol. Imaging*, 43:925-937 (2016) vs. huA33 (3A3-H2L2) assayed on GPA33 recombinant protein using SPR (BIACORE®-T100). The original humanized hA33 lost considerable affinity compared to huA33.

FIG. 23 shows the humanness analysis of huA33 heavy and light chain sequences (3A3-H1, 3A3-H2, 3A3-L1, 3A3-L2) and the original hA33 sequences. Since all four versions of rehumanization retained high binding affinity of original chA33, H2L2 version was chosen for further development based on its higher humanness T20 score.

FIG. 24 shows the amino acid sequences of the light chain and heavy chain of the chimeric chA33-IgG1, which correspond to SEQ ID NO: 13 and SEQ ID NO: 14 respectively.

FIG. 25 shows the amino acid and cDNA sequences of the heavy chain of huA33-IgG1 (H2L2), which correspond to SEQ ID NO: 15 and SEQ ID NO: 16 respectively.

FIG. 26 shows the amino acid and cDNA sequences of the light chain of huA33-IgG1 (H2L2), which correspond to SEQ ID NO: 17 and SEQ ID NO: 18 respectively.

FIG. 27 shows the amino acid and cDNA sequences of the heavy chain of T-cell engaging huA33-BsAb bispecific antibodies, which correspond to SEQ ID NO: 19 and SEQ ID NO: 20 respectively.

FIG. 28 shows the amino acid and cDNA sequences of the light chain of T-cell engaging huA33-BsAb bispecific antibodies, which correspond to SEQ ID NO: 21 and SEQ ID NO: 22 respectively. The underlined sequences correspond to GS linker sequences.

FIG. 29 shows a summary of potential modifications to the T-cell engaging huA33-BsAb bispecific antibodies disclosed herein.

FIG. 30 shows the amino acid sequences of the heavy chain and light chain of the affinity-matured clone 31 in huA33-BsAb format, corresponding to SEQ ID NO: 23 and SEQ ID NO: 24 respectively. The underlined sequences correspond to GS linker sequences.

FIG. 31 shows the amino acid sequences of the heavy chain and light chain of the affinity-matured clone 32 in huA33-BsAb format, corresponding to SEQ ID NO: 25 and SEQ ID NO: 26 respectively. The underlined sequences correspond to GS linker sequences.

FIG. 32 shows the amino acid sequences of the heavy chain and light chain of the affinity-matured clone 48 in huA33-BsAb format, corresponding to SEQ ID NO: 27 and SEQ ID NO: 28 respectively. The underlined sequences correspond to GS linker sequences.

FIG. 33 shows the amino acid sequences of the heavy chain and light chain of the affinity-matured clone 49 in huA33-BsAb format, corresponding to SEQ ID NO: 29 and SEQ ID NO: 30 respectively. The underlined sequences correspond to GS linker sequences.

FIG. 34 shows the amino acid sequences of the heavy chain and light chain of the affinity-matured clone 53 in huA33-BsAb format, corresponding to SEQ ID NO: 31 and SEQ ID NO: 32 respectively. The underlined sequences correspond to GS linker sequences.

FIG. 35 shows the amino acid sequences of the heavy chain and light chain of the affinity-matured clone 56 in huA33-BsAb format, corresponding to SEQ ID NO: 33 and SEQ ID NO: 34 respectively. The underlined sequences correspond to GS linker sequences.

FIG. 36 shows the amino acid sequences of the heavy chain and light chain of the affinity-matured clone 57 in huA33-BsAb format, corresponding to SEQ ID NO: 35 and SEQ ID NO: 36 respectively. The underlined sequences correspond to GS linker sequences.

FIG. 37 shows the amino acid and cDNA sequences of the heavy chain of bispecific antibodies huA33-huC825 (H2L2), which correspond to SEQ ID NO: 58 and SEQ ID NO: 59, respectively.

FIG. 38 shows the amino acid and cDNA sequences of the light chain of bispecific antibodies huA33-huC825 (H2L2), which correspond to SEQ ID NO: 60 and SEQ ID NO: 61, respectively. The underlined sequences correspond to GS linker sequences.

FIG. 39 shows the amino acid sequence of the heavy chain and light chain of the bispecific antibodies huA33-mC825 (H2L2), which correspond to SEQ ID NO: 62 and SEQ ID NO: 63, respectively. The underlined sequences correspond to GS linker sequences.

DETAILED DESCRIPTION

Figure 3:
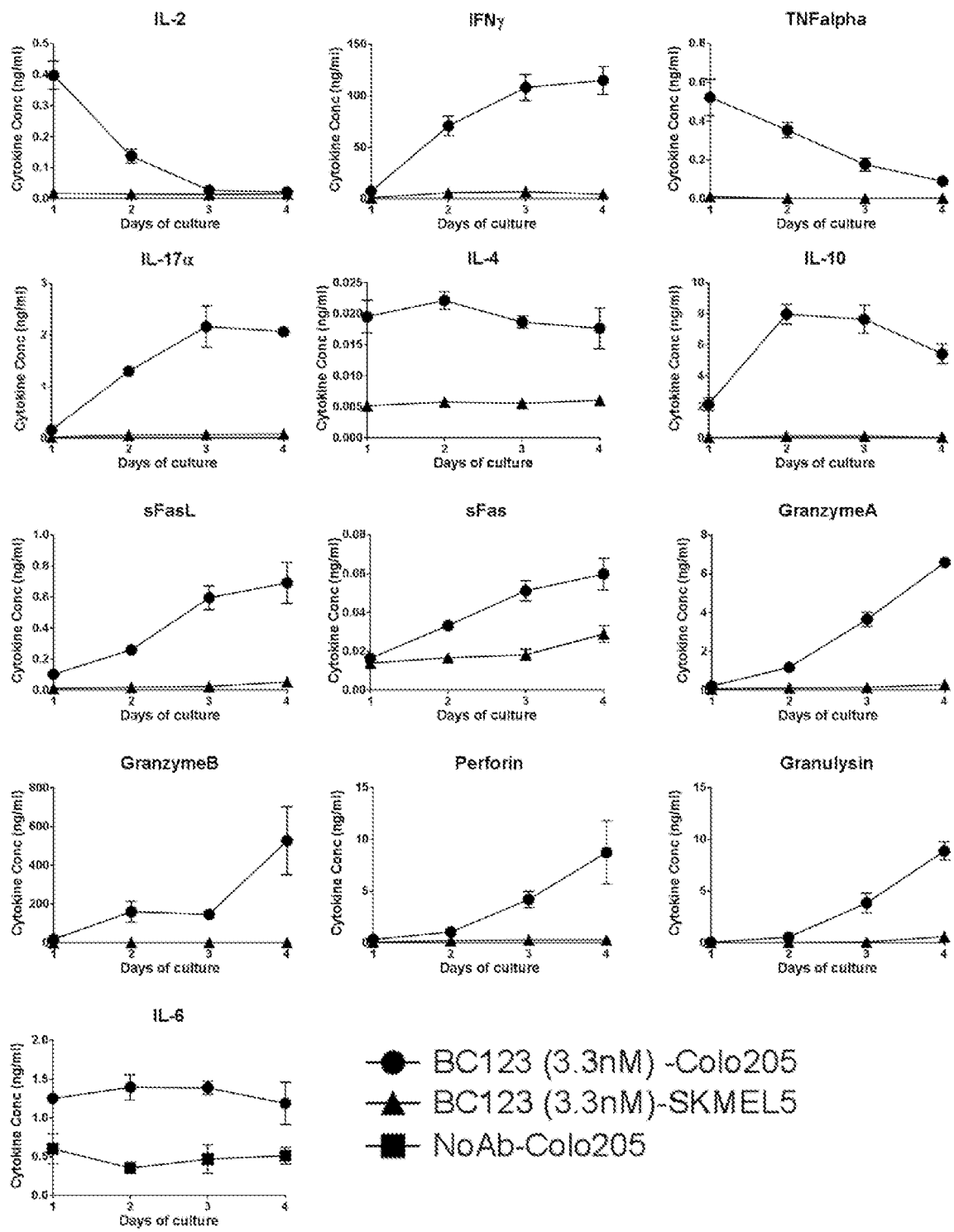
FIG. 3 shows the profile of secreted cytokines and cytotoxic components by huA33-BsAb activated T cells in the presence of a target tumor. The kinetics of cytokine and cytolytic molecule production by T cells in the presence of huA33-BsAb and target cell Colo205 or negative control cell SKMEL5 were determined over 4 days. Because SKMEL5 secreted copious amounts of IL-6, the supernatant from T cells incubated with Colo205 cells in the absence of antibody was used as a negative control in the IL-6 kinetics experiment.

It is to be appreciated that certain aspects, modes, embodiments, variations and features of the present methods are described below in various levels of detail in order to provide a substantial understanding of the present technology.

The present disclosure generally provides immunoglobulin-related compositions (e.g., antibodies or antigen binding fragments thereof), which can specifically bind to and neutralize the biological activity of A33 polypeptides. The immunoglobulin-related compositions of the present technology are useful in methods for detecting or treating A33 associated cancers in a subject in need thereof. Accordingly, the various aspects of the present methods relate to the preparation, characterization, and manipulation of anti-A33 antibodies. The immunoglobulin-related compositions of the present technology are useful alone or in combination with additional therapeutic agents for treating cancer. In some embodiments, the immunoglobulin-related composition is a humanized antibody, a chimeric antibody, or a bispecific antibody.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series Methods in Enzymology (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization;* Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, $3^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a φ-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds A33 protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multispecific antibodies, bispecific antibodies, etc.) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a $F(ab')_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., Nature 341: 544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', $F(ab')_2$, and $F_v$ fragments; diabodies; linear antibodies; single-chain antibody molecules; and multispecific antibodies formed from antibody fragments.

"Bispecific antibody" or "BsAb", as used herein, refers to an antibody that can bind simultaneously to two targets that have a distinct structure, e.g., two different target antigens, two different epitopes on the same target antigen, or a hapten and a target antigen or epitope on a target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), $F(ab')_2$, Fd, Fv, dAB, scFv, etc.) having $V_H$ and/or $V_L$ regions that contain CDRs from a second monoclonal antibody.

As used herein, a "clearing agent" is an agent that binds to excess bispecific antibody that is present in the blood compartment of a subject to facilitate rapid clearance via kidneys. The use of the clearing agent prior to hapten administration (e.g., DOTA) facilitates better tumor-to-background ratios in pretargeted radioimmunotherapy (PRIT) systems. Examples of clearing agents include 500 kD-dextran-DOTA-Bn(Y) (Orcutt et al., Mol Cancer Ther. 11(6): 1365-1372 (2012)), 500 kD aminodextran-DOTA conjugate, antibodies against the pretargeting antibody, etc.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and 30 Hollinger et al., Proc. Natl. Acad. Sci. USA, 90: 6444-6448 (1993).

As used herein, the terms "single-chain antibodies" or "single-chain $F_v$ (scFv)" refer to an antibody fusion molecule of the two domains of the $F_v$ fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ (scF$_v$)). Bird et al. (1988) Science 242:423-426 and Huston et al. (1988) Proc. Natl. Acad Sci. USA 85:5879-5883. Such single-chain antibodies can be prepared by recombinant techniques or enzymatic or chemical cleavage of intact antibodies.

Any of the above-noted antibody fragments are obtained using conventional techniques known to those of skill in the art, and the fragments are screened for binding specificity and neutralization activity in the same manner as are intact antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., an A33 polypeptide). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, scFvFc, Fab, Fab' and F(ab')$_2$, but are not limited thereto.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a breast, lung, colon, or prostate tissue sample obtained by needle biopsy.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 0125, 023; Better et al., *Science* 240: 1041-1043, 1988; Liu et al., *Proc. Natl. Acad. Sci. USA* 84: 3439-3443, 1987; Liu et al., *J. Immunol* 139: 3521-3526, 1987; Sun et al., *Proc. Natl. Acad. Sci. USA* 84: 214-218, 1987; Nishimura et al., *Cancer Res* 47: 999-1005, 1987; Wood et al., *Nature* 314: 446-449, 1885; and Shaw et al., *J. Natl. Cancer Inst.* 80: 1553-1559, 1988.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, an "epitope" of the A33 protein is a region of the protein to which the anti-A33 antibodies of the present technology specifically bind. In some embodiments, the epitope is a conformational epitope. To screen for anti-A33 antibodies which bind to an epitope, a routine cross-blocking assay such as that described in Antibodies, *A Laboratory Manual*, Cold Spring Harbor Laboratory, Ed Harlow and David Lane (1988), can be performed. This assay can be used to determine if an anti-A33 antibody binds the same site or epitope as an anti-A33 antibody of the present technology. Alternatively, or additionally, epitope mapping can be performed by methods known in the art. For example, the antibody sequence can be mutagenized such as by alanine scanning, to identify contact residues. In a different method, peptides corresponding to different regions of A33 protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', F(ab')$_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321: 522-525 (1986); Reichmann et al., *Nature* 332:323-329 (1988); and Presta, *Curr. Op. Struct. Biol.* 2:593-596 (1992). See e.g., Ahmed & Cheung, *FEBS Letters* 588(2):288-297 (2014).

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region) as measured using a BLAST or BLAST 2.0 sequence comparison algorithms with default parameters described below, or by manual alignment and visual inspection, e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the terms "individual", "patient", or "subject" can be an individual organism, a vertebrate, a mammal, or a human. In some embodiments, the individual, patient or subject is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816,567). The "monoclonal antibodies" may also be isolated from phage antibody libraries using the techniques described in Clackson et al., *Nature* 352:624-628 (1991) and Marks et al., *J Mol. Biol.* 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, "PRIT" or "pretargeted radioimmunotherapy" refers to a multistep process that resolves the slow blood clearance of tumor targeting antibodies, which contributes to undesirable toxicity to normal tissues such as bone marrow. In pre-targeting, a radionuclide or other diagnostic or therapeutic agent is attached to a small hapten. A pre-targeting bispecific antibody, which has binding sites for the hapten as well as a target antigen, is administered first. Unbound antibody is then allowed to clear from circulation and the hapten is subsequently administered.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a polypeptide, or an epitope on a polypeptide), as used herein, can be exhibited, for example, by a molecule having a $K_D$ for the molecule to which it binds to of about $10^{-4}$ M, $10^{-5}$ M, $10^{-6}$ M, $10^{-7}$ M, $10^{-8}$ M, $10^{-9}$M, $10^{-10}$M, $10^{-11}$ M, or $10^{-12}$M. The term "specifically binds" may also refer to binding where a molecule (e.g., an antibody or antigen binding fragment thereof) binds to a particular polypeptide (e.g., an A33 polypeptide), or an epitope on a particular polypeptide, without substantially binding to any other polypeptide, or polypeptide epitope.

As used herein, the term "simultaneous" therapeutic use refers to the administration of at least two active ingredients by the same route and at the same time or at substantially the same time.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-A33 antibodies described herein are contemplated. For example, it may be desirable to improve the binding affinity and/or other biological properties of the antibody. Amino acid sequence variants of an anti-A33 antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in the Table below.

TABLE 1

Amino Acid Substitutions

| Original Residue | Exemplary Substitutions | Conservative Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

CRC and A33

CRC is a heterogeneous disease and can be subdivided into 4 consensus molecular subtypes (CMS) based on gene expression analysis, i.e., CMS1-4. MSI tumors mainly belong to CMS1 (14% of all CRC patients) and are characterized by genome hypermutation and microsatellite instability, due to deficiencies in DNA repair pathways. Presumably, hypermutation creates a plethora of neoantigens that are presented on the cell surface and attract T cells into tumors. Indeed, CMS1 has a strong molecular signature of immune system activation and evasion. ICIs function by reinvigorating repressed tumor infiltrating lymphocytes (TILs) to regain tumoricidal capabilities and therefore, MSI tumors are the most responsive CRC tumors to ICIs. However, MSI tumors account for <5% of mCRC; for the majority of mCRC, the efficacy of ICIs so far has been disappointing. Peritoneal carcinomatosis is typically the terminal phase of incurable CRC. Unlike metastasis to liver and lung, it is usually unresectable, unresponsive to chemotherapy and radiation, causing significant morbidity. Current treatment is mostly palliative, consisting of cytoreduction surgery (CRS) and hyperthemic chemotherapy (HIPEC), which are effective in only a small percentage of patients with small volume disease.

Human Glycoprotein A33 (GPA33 or A33) is a single-pass type I membrane protein that belongs to the CTX family of cell adhesion molecular within the immunoglobulin family. A33 is expressed in 95% of CRC tissues with very restricted expression in normal tissues. A33 comprises one Ig-like C2-type domain and one Ig-like V-type domain. The predicted mature protein includes a single transmembrane domain, an extracellular region and an intracellular tail. A33 plays a role in intracellular traffic, cell-cell recognition/signaling and recycling to the cell surface. The amino acid sequence of the ectodomain of A33 (Ile22-Val235) is provided below:

(SEQ ID NO: 57)
ISVETPQDVLRASQGKSVTLPCTYHTSTSSREGLIQWDKLLLTHTERVVI

WPFSNKNYIHGELYKNRVSISNNAEQSDASITIDQLTMADNGTYECSVSL

MSDLEGNTKSRVRLLVLVPPSKPECGIEGETIIGNNIQLTCQSKEGSPTP

QYSWKRYNILNQEQPLAQPASGQPVSLKNISTDTSGYYICTSSNEEGTQF

CNITVAVRSPSMNV.

Immunoglobulin-Related Compositions of the Present Technology

Existing humanized A33 IgG1 antibodies have been found to be immunogenic in colon cancer patients. See Ritter G et al., *Cancer Res* 61:6851-9 (2001). The present technology describes methods and compositions for the generation and use of anti-A33 immunoglobulin-related compositions (e.g., anti-A33 antibodies or antigen binding fragments thereof). The anti-A33 immunoglobulin-related compositions of the present disclosure may be useful in the diagnosis, or treatment of A33-positive cancers. Anti-A33 immunoglobulin-related compositions within the scope of the present technology include, e.g., but are not limited to, monoclonal, chimeric, humanized, and diabodies that specifically bind the target polypeptide, a homolog, derivative or a fragment thereof. The present disclosure also provides antigen binding fragments of any of the anti-A33 antibodies disclosed herein, wherein the antigen binding fragment is selected from the group consisting of Fab, F(ab)'2, Fab', scF$_v$, and F$_v$.

In one aspect, the present technology provides an antibody or antigen binding fragment thereof comprising a heavy chain immunoglobulin variable domain ($V_H$) and a light chain immunoglobulin variable domain ($V_L$), wherein (a) the $V_H$ comprises a $V_H$-CDR$_1$ sequence of FTFSTYDMS (SEQ ID NO: 37), a $V_H$-CDR$_2$ sequence of TISSGG-SYTYYLDSVKG (SEQ ID NO: 38), and a $V_H$-CDR$_3$ sequence of TTVVPFAY (SEQ ID NO: 39); and/or (b) the $V_L$ comprises a $V_L$-CDR$_1$ sequence, a $V_L$-CDR$_2$ sequence, and a $V_L$-CDR3 sequence selected from the group consisting of: KASQNVRTVVA (SEQ ID NO: 40), LASNRHT (SEQ ID NO: 41), and QYWSYPLT (SEQ ID NO: 42); KASQNVRTVVA (SEQ ID NO: 40), LASDRHT (SEQ ID NO: 43), and QYWSYPLT (SEQ ID NO: 42); KASQNVRTLVA (SEQ ID NO: 44), LASNRHT (SEQ ID NO: 41), and QHWSYPLT (SEQ ID NO: 45); and KASQNVRTLVA (SEQ ID NO: 44), LASNRHT (SEQ ID NO: 41), and QYWSYPLT (SEQ ID NO: 42). In some embodiments, the antibody further comprises a Fc domain of any isotype, e.g., but are not limited to, IgG (including IgG1, IgG2, IgG3, and IgG4), IgA (including IgA$_1$ and IgA$_2$), IgD, IgE, or IgM, and IgY. Non-limiting examples of constant region sequences include:

Human IgD constant region, Uniprot: P01880
(SEQ ID NO: 46)
APTKAPDVFPIISGCRHPKDNSPVVLACLITGYHPTSVTVTWYMGTQSQP

QRTFPEIQRRDSYYMTSSQLSTPLQQWRQGEYKCVVQHTASKSKKEIFRW

PESPKAQASSVPTAQPQAEGSLAKATTAPATTRNTGRGGEEKKKEKEKEE

QEERETKTPECPSHTQPLGVYLLTPAVQDLWLRDKATFTCFVVGSDLKDA

HLTWEVAGKVPTGGVEEGLLERHSNGSQSQHSRLTLPRSLWNAGTSVTCT

LNHPSLPPQRLMALREPAAQAPVKLSLNLLASSDPPEAASWLLCEVSGFS

PPNILLMWLEDQREVNTSGFAPARPPPQPGSTTFWAWSVLRVPAPPSPQP

ATYTCVVSHEDSRTLLNASRSLEVSYVTDHGPMK

Human IgG1 constant region, Uniprot: P01857
(SEQ ID NO: 47)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGEYPSDIAVEWESNGQPENNYKTTPPVLDSDGSFFLYSKLTVDKSRW

QQGNVFSCSVMHEALHNHYTQKSLSLSPGK

Human IgG2 constant region, Uniprot: P01859
(SEQ ID NO: 48)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDISVEWESNGQPENNYKTTPPMLDSDGSFFLYSKLTVDKSRWQQGN

VFSCSVMHEALHNHYTQKSLSLSPGK

Human IgG3 constant region, Uniprot: P01860
(SEQ ID NO: 49)
ASTKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVEL

KTPLGDTTHTCPRCPEPKSCDTPPPCPRCPEPKSCDTPPPCPRCPEPKSC

DTPPPCPRCPAPELLGGPSVFLFPPKPKDTLMISRTPEVTCVVVDVSHED

PEVQFKWYVDGVEVHNAKTKPREEQYNSTFRVVSVLTVLHQDWLNGKEYK

CKVSNKALPAPIEKTISKTKGQPREPQVYTLPPSREEMTKNQVSLTCLVK

GFYPSDIAVEWESSGQPENNYNTTPPMLDSGSFFLYSKLTVDKSRWQQG

NIFSCSVMHEALHNRFTQKSLSLSPGK

Human IgM constant region, Uniprot: P01871
(SEQ ID NO: 50)
GSASAPTLFPLVSCENSPSDTSSVAVGCLAQDFLPDSITLSWKYKNNSDI

SSTRGFPSVLRGGKYAATSQVLLPSKDVMQGTDEHVVCKVQHPNGNKEKN

VPLPVIAELPPKVSVFVPPRDGFFGNPRKSKLICQATGFSPRQIQVSWLR

EGKQVGSGVTTDQVQAEAKESGPTTYKVTSTLTIKESDWLGQSMFTCRVD

HRGLTFQQNASSMCVPDQDTAIRVFAIPPSFASIFLTKSTKLTCLVTDLT

TYDSVTISWTRQNGEAVKTHTNISESHPNATFSAVGEASICEDDWNSGER

-continued

FTCTVTHTDLPSPLKQTISRPKGVALHRPDVYLLPPAREQLNLRESATIT

CLVTGFSPADVFVQWMQRGQPLSPEKYVTSAPNIPEPQAPGRYFAHSILT

VSEEEWNTGETYTCVAHEALPNRVTERTVDKSTGKPTLYNVSLVMSDTAG

TCY

Human IgG4 constant region, Uniprot: P01861
(SEQ ID NO: 51)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDGSFFLYSRLTVDKSRWQEGNVFSCSVMHEALHNHYTQKSLSLSL

GK

Human IgA1 constant region, Uniprot: P01876
(SEQ ID NO: 52)
ASPTSPKVFPLSLCSTQPDGNVVIACLVQGFFPQEPLSVTWSESGQGVTA

RNFPPSQDASGDLYTTSSQLTLPATQCLAGKSVTCHVKHYTNPSQDVTVP

CPVPSTPPTPSPSTPPTPSPSCCHPRLSLHRPALEDLLLGSEANLTCTLT

GLRDASGVTFTWTPSSGKSAVQGPPERDLCGCYSVSSVLPGCAEPWNHGK

TFTCTAAYPESKTPLTATLSKSGNTFRPEVHLLPPPSEELALNELVTLTC

LARGFSPKDVLVRWLQGSQELPREKYLTWASRQEPSQGTTTFAVTSILRV

AAEDWKKGDTFSCMVGHEALPLAFTQKTIDRLAGKPTHVNVSVVMAEVDG

TCY

Human IgA2 constant region, Uniprot: P01877
(SEQ ID NO: 53)
ASPTSPKVFPLSLDSTPQDGNVVVACLVQGFFPQEPLSVTWSESGQNVTA

RNFPPSQDASGDLYTTSSQLTLPATQCPDGKSVTCHVKHYTNPSQDVTVP

CPVPPPPPCCHPRLSLHRPALEDLLLGSEANLTCTLTGLRDASGATFTWT

PSSGKSAVQGPPERDLCGCYSVSSVLPGCAQPWNHGETFTCTAAHPELKT

PLTANITKSGNTFRPEVHLLPPPSEELALNELVTLTCLARGFSPKDVLVR

WLQGSQELPREKYLTWASRQEPSQGTTTFAVTSILRVAAEDWKKGDTFSC

MVGHEALPLAFTQKTIDRMAGKPTHVNVSVVMAEVDGTCY

Human Ig kappa constant region, Uniprot: P01834
(SEQ ID NO: 54)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

In some embodiments, the immunoglobulin-related compositions of the present technology comprise a heavy chain constant region that is at least 80%, at least 85%, at least 90%, at least 95%, at least 99%, or is 100% identical to SEQ ID NOS: 46-53. Additionally or alternatively, in some embodiments, the immunoglobulin-related compositions of the present technology comprise a light chain constant region that is at least 80%, at least 85%, at least 90%, at least 95%, at least 99%, or is 100% identical to SEQ ID NO: 54. In some embodiments, the immunoglobulin-related compositions of the present technology bind to an epitope of an A33 polypeptide comprising at least five to eight consecutive amino acid residues of SEQ ID NO: 57. In some embodiments, the epitope is a conformational epitope.

In another aspect, the present disclosure provides an isolated immunoglobulin-related composition (e.g., an antibody or antigen binding fragment thereof) comprising a heavy chain (HC) amino acid sequence comprising SEQ ID NO: 5, SEQ ID NO: 6, SEQ ID NO: 15, SEQ ID NO: 19, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 58, SEQ ID NO: 62, or a variant thereof having one or more conservative amino acid substitutions.

Additionally or alternatively, in some embodiments, the immunoglobulin-related compositions of the present technology comprise a light chain (LC) amino acid sequence comprising SEQ ID NO: 9, SEQ ID NO: 10, SEQ ID NO: 17, SEQ ID NO: 21, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 60, SEQ ID NO: 63, or a variant thereof having one or more conservative amino acid substitutions.

In some embodiments, the immunoglobulin-related compositions of the present technology comprise a HC amino acid sequence and a LC amino acid sequence selected from the group consisting of: SEQ ID NO: 5 and SEQ ID NO: 9 (3A3-H1/L1); SEQ ID NO: 5 and SEQ ID NO: 10 (3A3-H1/L2); SEQ ID NO: 6 and SEQ ID NO: 9 (3A3-H2/L1); SEQ ID NO: 6 and SEQ ID NO: 10 (3A3-H2/L2); SEQ ID NO: 15 and SEQ ID NO: 17 (huA33-IgG1 (H2L2)); SEQ ID NO: 19 and SEQ ID NO: 21 (huA33-BsAb); SEQ ID NO: 23 and SEQ ID NO: 24 (clone 31); SEQ ID NO: 25 and SEQ ID NO: 26 (clone 32); SEQ ID NO: 27 and SEQ ID NO: 28 (clone 48); SEQ ID NO: 29 and SEQ ID NO: 30 (clone 49); SEQ ID NO: 31 and SEQ ID NO: 32 (clone 53); SEQ ID NO: 33 and SEQ ID NO: 34 (clone 56); SEQ ID NO: 35 and SEQ ID NO: 36 (clone 57), SEQ ID NO: 58 and SEQ ID NO: 60 (huA33-huC825); and SEQ ID NO: 62 and SEQ ID NO: 63 (huA33-mC825), respectively.

In any of the above embodiments of the immunoglobulin-related compositions, the HC and LC immunoglobulin variable domain sequences form an antigen binding site that binds to an epitope of an A33 polypeptide comprising at least five to eight consecutive amino acid residues of the ectodomain of A33 (SEQ ID NO: 57). In some embodiments, the epitope is a conformational epitope.

In some embodiments, the HC and LC immunoglobulin variable domain sequences are components of the same polypeptide chain. In other embodiments, the HC and LC immunoglobulin variable domain sequences are components of different polypeptide chains. In certain embodiments, the antibody is a full-length antibody.

In some embodiments, the immunoglobulin-related compositions of the present technology bind specifically to at least one A33 polypeptide. In some embodiments, the immunoglobulin-related compositions of the present technology bind at least one A33 polypeptide with a dissociation constant ($K_D$) of about $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In certain embodiments, the immunoglobulin-related compositions are monoclonal antibodies, chimeric antibodies, humanized antibodies, or bispecific antibodies. In some embodiments, the antibodies comprise a human antibody framework region.

In certain embodiments, the immunoglobulin-related composition includes one or more of the following characteristics: (a) the light chain immunoglobulin variable domain sequence is at least 80%, at least 85%, at least 90%, at least 95%, or at least 99% identical to the light chain immunoglobulin variable domain sequence present in any one of SEQ ID NOs: 9, 10, 17, 21, 24, 26, 28, 30, 32, 34, 36, 60, or 63; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 5, 6, 15, 19, 23, 25, 27, 29, 31, 33, 35, 58 or 62. In another aspect, one or more amino acid residues in the immunoglobulin-related compositions provided herein are substituted with another amino acid. The substitution may be a "conservative substitution" as defined herein.

In some embodiments, the immunoglobulin-related composition comprises (a) a LC sequence that is at least 80%, at least 85%, at least 90%, at least 95%, or at least 99% identical to the LC sequence present in any one of SEQ ID NOs: 9, 10, 17, 21, 24, 26, 28, 30, 32, 34, 36, 60, or 63; and/or (b) a HC sequence that is at least 80%, at least 85%, at least 90%, at least 95%, or at least 99% identical to the HC sequence present in any one of SEQ ID NOs: 5, 6, 15, 19, 23, 25, 27, 29, 31, 33, 35, 58 or 62.

In certain embodiments, the immunoglobulin-related compositions contain an IgG1 constant region comprising one or more amino acid substitutions selected from the group consisting of N297A and K322A. Additionally or alternatively, in some embodiments, the immunoglobulin-related compositions contain an IgG4 constant region comprising a S228P mutation.

In some aspects, the anti-A33 immunoglobulin-related compositions described herein contain structural modifications to facilitate rapid binding and cell uptake and/or slow release. In some aspects, the anti-A33 immunoglobulin-related composition of the present technology (e.g., an antibody) may contain a deletion in the CH2 constant heavy chain region to facilitate rapid binding and cell uptake and/or slow release. In some aspects, a Fab fragment is used to facilitate rapid binding and cell uptake and/or slow release. In some aspects, a F(ab)'$_2$ fragment is used to facilitate rapid binding and cell uptake and/or slow release.

In one aspect, the present technology provides a nucleic acid sequence encoding a heavy chain or a light chain of an immunoglobulin-related composition described herein. Also disclosed herein are recombinant nucleic acid sequences encoding any of the antibodies described herein. In some embodiments, the nucleic acid sequence is selected from the group consisting of SEQ ID NOs: 7, 8, 11, 12, 16, 18, 20, 22, 59 and 61. In another aspect, the present technology provides a host cell expressing any nucleic acid sequence encoding a heavy chain or a light chain of an immunoglobulin-related composition described herein.

The immunoglobulin-related compositions of the present technology (e.g., an anti-A33 antibody) can be monospecific, bispecific, trispecific or of greater multispecificity. Multispecific antibodies can be specific for different epitopes of one or more A33 polypeptides or can be specific for both the A33 polypeptide(s) as well as for heterologous compositions, such as a heterologous polypeptide or solid support material. See, e.g., WO 93/17715; WO 92/08802; WO 91/00360; WO 92/05793; Tutt et al., J. Immunol. 147: 60-69 (1991); U.S. Pat. Nos. 5,573,920, 4,474,893, 5,601, 819, 4,714,681, 4,925,648; 6,106,835; Kostelny et al., J. Immunol. 148: 1547-1553 (1992). In some embodiments, the immunoglobulin-related compositions are chimeric. In certain embodiments, the immunoglobulin-related compositions are humanized.

The immunoglobulin-related compositions of the present technology can further be recombinantly fused to a heterologous polypeptide at the N- or C-terminus or chemically conjugated (including covalently and non-covalently conjugations) to polypeptides or other compositions. For example, the immunoglobulin-related compositions of the present technology can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

In any of the above embodiments of the immunoglobulin-related compositions of the present technology, the antibody or antigen binding fragment may be optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof. For a chemical bond or physical bond, a functional group on the immunoglobulin-related composition typically associates with a functional group on the agent. Alternatively, a functional group on the agent associates with a functional group on the immunoglobulin-related composition.

The functional groups on the agent and immunoglobulin-related composition can associate directly. For example, a functional group (e.g., a sulfhydryl group) on an agent can associate with a functional group (e.g., sulfhydryl group) on an immunoglobulin-related composition to form a disulfide. Alternatively, the functional groups can associate through a cross-linking agent (i.e., linker). Some examples of cross-linking agents are described below. The cross-linker can be attached to either the agent or the immunoglobulin-related composition. The number of agents or immunoglobulin-related compositions in a conjugate is also limited by the number of functional groups present on the other. For example, the maximum number of agents associated with a conjugate depends on the number of functional groups present on the immunoglobulin-related composition. Alternatively, the maximum number of immunoglobulin-related compositions associated with an agent depends on the number of functional groups present on the agent.

In yet another embodiment, the conjugate comprises one immunoglobulin-related composition associated to one agent. In one embodiment, a conjugate comprises at least one agent chemically bonded (e.g., conjugated) to at least one immunoglobulin-related composition. The agent can be chemically bonded to an immunoglobulin-related composition by any method known to those in the art. For example, a functional group on the agent may be directly attached to a functional group on the immunoglobulin-related composition. Some examples of suitable functional groups include, for example, amino, carboxyl, sulfhydryl, maleimide, isocyanate, isothiocyanate and hydroxyl.

The agent may also be chemically bonded to the immunoglobulin-related composition by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; 5,985, 566; and 6,133,038 of Kreatech Biotechnology, B. V., Amsterdam, The Netherlands.

Alternatively, the functional group on the agent and immunoglobulin-related composition can be the same. Homobifunctional cross-linkers are typically used to cross-link identical functional groups. Examples of homobifunctional cross-linkers include EGS (i.e., ethylene glycol bis

[succinimidylsuccinate]), DSS (i.e., disuccinimidyl suberate), DMA (i.e., dimethyl adipimidate.2HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

In other instances, it may be beneficial to cleave the agent from the immunoglobulin-related composition. The web-site of Pierce Biotechnology, Inc. described above can also provide assistance to one skilled in the art in choosing suitable cross-linkers which can be cleaved by, for example, enzymes in the cell. Thus the agent can be separated from the immunoglobulin-related composition. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid HCl).

In another embodiment, a conjugate comprises at least one agent physically bonded with at least one immunoglobulin-related composition. Any method known to those in the art can be employed to physically bond the agents with the immunoglobulin-related compositions. For example, the immunoglobulin-related compositions and agents can be mixed together by any method known to those in the art. The order of mixing is not important. For instance, agents can be physically mixed with immunoglobulin-related compositions by any method known to those in the art. For example, the immunoglobulin-related compositions and agents can be placed in a container and agitated, by for example, shaking the container, to mix the immunoglobulin-related compositions and agents.

The immunoglobulin-related compositions can be modified by any method known to those in the art. For instance, the immunoglobulin-related composition may be modified by means of cross-linking agents or functional groups, as described above.

A. Methods of Preparing Anti-A33 Antibodies of the Present Technology

General Overview. Initially, a target polypeptide is chosen to which an antibody of the present technology can be raised. For example, an antibody may be raised against the full-length A33 protein, or to a portion of the extracellular domain of the A33 protein. Techniques for generating antibodies directed to such target polypeptides are well known to those skilled in the art. Examples of such techniques include, for example, but are not limited to, those involving display libraries, xeno or human mice, hybridomas, and the like. Target polypeptides within the scope of the present technology include any polypeptide derived from A33 protein containing the extracellular domain which is capable of eliciting an immune response. The preparation of antibodies specific for A33 protein is illustrated in Examples 1, 2, 3, and 5.

It should be understood that recombinantly engineered antibodies and antibody fragments, e.g., antibody-related polypeptides, which are directed to A33 protein and fragments thereof are suitable for use in accordance with the present disclosure.

Anti-A33 antibodies that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target polypeptide antigen is obtained. An originating species is any species which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli*.

Due to the degeneracy of nucleic acid coding sequences, other sequences which encode substantially the same amino acid sequences as those of the naturally occurring proteins may be used in the practice of the present technology. These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," *Macromolecule Sequencing and Synthesis, Selected Methods and Applications*, pp. 127-149, 1998, Alan R. Liss, Inc.) so long as such a variant forms an operative antibody which recognizes A33 proteins. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Preparation of Polyclonal Antisera and Immunogens. Methods of generating antibodies or antibody fragments of the present technology typically include immunizing a subject (generally a non-human subject such as a mouse or rabbit) with a purified A33 protein or fragment thereof or with a cell expressing the A33 protein or fragment thereof. An appropriate immunogenic preparation can contain, e.g., a recombinantly-expressed A33 protein or a chemically-synthesized A33 peptide. The ECM of A33 protein, or a portion or fragment thereof, can be used as an immunogen to generate an anti-A33 antibody that binds to the A33 protein, or a portion or fragment thereof using standard techniques for polyclonal and monoclonal antibody preparation.

The full-length A33 protein or fragments thereof, are useful as fragments as immunogens. In some embodiments, an A33 fragment comprises at least five to eight consecutive amino acid residues of the amino acid sequence of SEQ ID NO: 57, and encompasses an epitope of the A33 protein such that an antibody raised against the peptide forms a specific immune complex with A33 protein.

In some embodiments, the antigenic A33 peptide overlapping with the A33 ectodomain (Ile22-Val235) comprises at least 5, 8, 10, 15, 20, or 30 amino acid residues. Longer antigenic peptides are sometimes desirable over shorter antigenic peptides, depending on use and according to methods well known to those skilled in the art. Multimers of a given epitope are sometimes more effective than a monomer.

If needed, the immunogenicity of the A33 protein (or fragment thereof) can be increased by fusion or conjugation to a hapten such as keyhole limpet hemocyanin (KLH) or ovalbumin (OVA). Many such haptens are known in the art. One can also combine the A33 protein with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

In describing the present technology, immune responses may be described as either "primary" or "secondary" immune responses. A primary immune response, which is also described as a "protective" immune response, refers to an immune response produced in an individual as a result of some initial exposure (e.g., the initial "immunization") to a particular antigen, e.g., A33 protein. In some embodiments, the immunization can occur as a result of vaccinating the individual with a vaccine containing the antigen. For example, the vaccine can be an A33 vaccine comprising one or more A33 protein-derived antigens. A primary immune response can become weakened or attenuated over time and can even disappear or at least become so attenuated that it cannot be detected. Accordingly, the present technology also relates to a "secondary" immune response, which is also described here as a "memory immune response." The term secondary immune response refers to an immune response elicited in an individual after a primary immune response has already been produced.

Thus, a secondary immune response can be elicited, e.g., to enhance an existing immune response that has become weakened or attenuated, or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4$^+$ T cells. A first exposure to an antigen primes the immune system and additional exposure(s) results in a DTH.

Following appropriate immunization, the anti-A33 antibody can be prepared from the subject's serum. If desired, the antibody molecules directed against the A33 protein can be isolated from the mammal (e.g., from the blood) and further purified by well-known techniques, such as polypeptide A chromatography to obtain the IgG fraction.

Monoclonal Antibody. In one embodiment of the present technology, the antibody is an anti-A33 monoclonal antibody. For example, in some embodiments, the anti-A33 monoclonal antibody may be a human or a mouse anti-A33 monoclonal antibody. For preparation of monoclonal antibodies directed towards the A33 protein, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256: 495-497); the trioma technique; the human B-cell hybridoma technique (See, e.g., Kozbor, et al., 1983. *Immunol. Today* 4: 72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. *Proc. Natl. Acad. Sci. USA* 80: 2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the A33 protein. Alternatively, hybridomas expressing anti-A33 monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., A33 binding, can be used as expressed by the hybridoma, it can be bound to a molecule such as polyethylene glycol (PEG) to alter its properties, or a cDNA encoding it can be isolated, sequenced and manipulated in various ways. Synthetic dendromeric trees can be added to reactive amino acid side chains, e.g., lysine, to enhance the immunogenic properties of A33 protein. Also, CPG-dinucleotide techniques can be used to enhance the immunogenic properties of the A33 protein. Other manipulations include substituting or deleting particular amino acyl residues that contribute to instability of the antibody during storage or after administration to a subject, and affinity maturation techniques to improve affinity of the antibody of the A33 protein.

Hybridoma Technique. In some embodiments, the antibody of the present technology is an anti-A33 monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, N.Y., 349 (1988); Hammerling et al., *Monoclonal Antibodies And T-Cell Hybridomas*, 563-681 (1981). Other methods for producing hybridomas and monoclonal antibodies are well known to those of skill in the art.

Phage Display Technique. As noted above, the antibodies of the present technology can be produced through the application of recombinant DNA and phage display technology. For example, anti-A33 antibodies, can be prepared using various phage display methods known in the art. In phage display methods, functional antibody domains are displayed on the surface of a phage particle which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al., *Science* 246: 1275-1281, 1989) to allow rapid and effective identification of monoclonal Fab fragments with the desired specificity for an A33 polypeptide, e.g., a polypeptide or derivatives, fragments, analogs or homologs thereof. Other examples of phage display methods that can be used to make the antibodies of the present technology include those disclosed in Huston et al., *Proc. Natl. Acad. Sci U.S.A.*, 85: 5879-5883, 1988; Chaudhary et al., *Proc. Natl. Acad. Sci U.S.A.*, 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-A33 Antibodies. As noted above, the antibodies of the present technology can be produced through the application of recombinant DNA technology. Recombinant polynucleotide constructs encoding an anti-A33 antibody of the present technology typically include an expression control sequence operably-linked to the coding sequences of anti-A33 antibody chains, including naturally-associated or heterologous promoter regions. As such, another aspect of the technology includes vectors containing one or more nucleic acid sequences encoding an anti-A33 antibody of the present technology. For recombinant expression of one or more of the polypeptides of the present technology, the nucleic acid containing all or a portion of the nucleotide sequence encoding the anti-A33 antibody is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-A33 antibody, and the collection and purification of the anti-A33 antibody, e.g., cross-reacting anti-A33 antibodies. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with A33 binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-A33 antibody), include, e.g., but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-A33 antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-A33 antibody, etc.).

Another aspect of the present technology pertains to anti-A33 antibody-expressing host cells, which contain a nucleic acid encoding one or more anti-A33 antibodies. The recombinant expression vectors of the present technology can be designed for expression of an anti-A33 antibody in prokaryotic or eukaryotic cells. For example, an anti-A33 antibody can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-A33 antibody, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-A33 antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl. Acids Res.* 20: 2111-2118). Such alteration of nucleic acid sequences of the present technology can be carried out by standard DNA synthesis techniques.

In another embodiment, the anti-A33 antibody expression vector is a yeast expression vector. Examples of vectors for expression in yeast *Saccharomyces cerevisiae* include pYepSec1 (Baldari, et al., 1987. *EMBO J.* 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (Invitrogen Corp, San Diego, Calif.). Alternatively, an anti-A33 antibody can be expressed in insect cells using baculovirus expression vectors. Baculovirus vectors available for expression of polypeptides, e.g., anti-A33 antibody, in cultured insect cells (e.g., SF9 cells) include the pAc series (Smith, et al., *Mol. Cell. Biol.* 3: 2156-2165, 1983) and the pVL series (Lucklow and Summers, 1989. *Virology* 170: 31-39).

In yet another embodiment, a nucleic acid encoding an anti-A33 antibody of the present technology is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-A33 antibody of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), promoters of T cell receptors (Winoto and Baltimore, *EMBO J.* 8: 729-733, 1989) and immunoglobulins (Banerji, et al., 1983. *Cell* 33: 729-740; Queen and Baltimore, *Cell* 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-A33 antibody can be expressed in bacterial cells such as *E. coli*, insect cells, yeast or mammalian cells. Mammalian cells are a suitable host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Illustrative expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., Molecular Cloning). Suitable methods for transforming or transfecting host cells can be found in Sambrook, et al. (*MOLECULAR CLONING: A LABORATORY MANUAL.* 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-A33 antibody or can be introduced on a separate vector. Cells stably transfected with the introduced nucleic acid can be identified by drug selection (e.g., cells that have incorporated the selectable marker gene will survive, while the other cells die).

A host cell that includes an anti-A33 antibody of the present technology, such as a prokaryotic or eukaryotic host cell in culture, can be used to produce (i.e., express) recombinant anti-A33 antibody. In one embodiment, the method comprises culturing the host cell (into which a recombinant expression vector encoding the anti-A33 antibody has been introduced) in a suitable medium such that the anti-A33 antibody is produced. In another embodiment, the method further comprises the step of isolating the anti-A33 antibody from the medium or the host cell. Once expressed, collections of the anti-A33 antibody, e.g., the anti-A33 antibodies or the anti-A33 antibody-related polypeptides are purified from culture media and host cells. The anti-A33 antibody can be purified according to standard procedures of the art, including HPLC purification, column chromatography, gel electrophoresis and the like. In one embodiment, the anti-A33 antibody is produced in a host organism by the method of Boss et al., U.S. Pat. No. 4,816,397. Usually, anti-A33 antibody chains are expressed with signal sequences and are thus released to the culture media. However, if the anti-A33 antibody chains are not naturally secreted by host cells, the anti-A33 antibody chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-A33 antibodies, e.g., the anti-A33 antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single-Chain Antibodies. In one embodiment, the anti-A33 antibody of the present technology is a single-chain anti-A33 antibody. According to the present technology, techniques can be adapted for the production of single-chain antibodies specific to an A33 protein (See, e.g., U.S. Pat. No. 4,946,778). Examples of techniques which can be used to produce single-chain Fvs and antibodies of the present technology include those described in U.S. Pat. Nos. 4,946,778 and 5,258,498; Huston et al., *Methods in Enzymology,* 203: 46-88, 1991; Shu, L. et al., *Proc. Natl. Acad. Sci. USA,* 90: 7995-7999, 1993; and Skerra et al., *Science* 240: 1038-1040, 1988.

Chimeric and Humanized Antibodies. In one embodiment, the anti-A33 antibody of the present technology is a chimeric anti-A33 antibody. In one embodiment, the anti-A33 antibody of the present technology is a humanized anti-A33 antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-A33 antibodies, such as chimeric and humanized monoclonal antibodies, comprising both human and non-human portions, can be made using standard recombinant DNA techniques, and are within the scope of the present technology. For some uses, including in vivo use of the anti-A33 antibody of the present technology in humans as well as use of these agents in in vitro detection assays, it is possible to use chimeric or humanized anti-A33 antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Patent No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci. USA* 84: 3439-3443; Liu, et al., 1987. *J. Immunol.* 139: 3521-3526; Sun, et al., 1987. *Proc. Natl. Acad. Sci. USA* 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559; Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler, et al., 1988. *J. Immunol.* 141: 4053-4060. For example, antibodies can be humanized using a variety of techniques including CDR-grafting (EP 0 239 400; WO 91/09967; U.S. Pat. Nos. 5,530,101; 5,585,089; 5,859,205; 6,248,516; EP460167), veneering or resurfacing (EP 0 592 106; EP 0 519 596; Padlan E. A., Molecular Immunology, 28: 489-498, 1991; Studnicka et al., *Protein Engineering* 7: 805-814, 1994; Roguska et al., *PNAS* 91: 969-973, 1994), and chain shuffling (U.S. Pat. No. 5,565,332). In one embodiment, a cDNA encoding a murine anti-A33 monoclonal antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) *Science* 240: 1041-1043; Liu et al. (1987) *Proc. Natl. Acad. Sci. USA* 84: 3439-3443; Liu et al. (1987) *J Immunol* 139: 3521-3526; Sun et al. (1987) *Proc. Natl. Acad. Sci. USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559; U.S. Pat. Nos. 6,180,370; 6,300,064; 6,696,248; 6,706,484; 6,828,422.

In one embodiment, the present technology provides the construction of humanized anti-A33 antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for a humanized anti-A33 antibodies, heavy and light chain immunoglobulins.

CDR Antibodies. In some embodiments, the anti-A33 antibody of the present technology is an anti-A33 CDR antibody. Generally the donor and acceptor antibodies used to generate the anti-A33 CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently, all three CDRs in all variable domains of the acceptor antibody will be replaced with the corresponding donor CDRs, though one need replace only as many as necessary to permit adequate binding of the resulting CDR-grafted antibody to A33 protein. Methods for generating CDR-grafted and humanized antibodies are taught by Queen et al. U.S. Pat. Nos. 5,585,089; 5,693,761; 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-A33 CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-A33 CDR-grafted antibody significantly compared to the same antibody with a fully human FR.

Bispecific Antibodies (BsAbs). A bispecific antibody is an antibody that can bind simultaneously to two targets that have a distinct structure, e.g., two different target antigens, two different epitopes on the same target antigen, or a hapten and a target antigen or epitope on a target antigen. BsAbs can be made, for example, by combining heavy chains and/or light chains that recognize different epitopes of the same or different antigen. In some embodiments, by molecular function, a bispecific binding agent binds one antigen (or epitope) on one of its two binding arms (one VH/VL pair), and binds a different antigen (or epitope) on its second arm (a different VH/VL pair). By this definition, a bispecific binding agent has two distinct antigen binding arms (in both specificity and CDR sequences), and is monovalent for each antigen to which it binds.

Bispecific antibodies (BsAb) and bispecific antibody fragments (BsFab) of the present technology have at least one arm that specifically binds to, for example, A33 and at least one other arm that specifically binds to a second target antigen. In some embodiments, the second target antigen is an antigen or epitope of a B-cell, a T-cell, a myeloid cell, a plasma cell, or a mast-cell. Additionally or alternatively, in certain embodiments, the second target antigen is selected from the group consisting of CD3, CD4, CD8, CD20, CD19, CD21, CD23, CD46, CD80, HLA-DR, CD74, CD22, CD14, CD15, CD16, CD123, TCR gamma/delta, NKp46 and KTR. In certain embodiments, the BsAbs are capable of binding to tumor cells that express A33 antigen on the cell surface. In some embodiments, the BsAbs have been engineered to facilitate killing of tumor cells by directing (or recruiting) cytotoxic T cells to a tumor site. Other exemplary BsAbs include those with a first antigen binding site specific for A33 and a second antigen binding site specific for a small molecule hapten (e.g., DTP A, IMP288, DOTA, DOTA-Bn, DOTA-desferrioxamine, other DOTA-chelates described herein, Biotin, fluorescein, or those disclosed in Goodwin, D A. et al, 1994, *Cancer Res.* 54(22):5937-5946).

A variety of bispecific fusion proteins can be produced using molecular engineering. For example, BsAbs have been constructed that either utilize the full immunoglobulin framework (e.g., IgG), single chain variable fragment (scFv), or combinations thereof. In some embodiments, the bispecific fusion protein is divalent, comprising, for example, a scFv with a single binding site for one antigen and a Fab fragment with a single binding site for a second antigen. In other embodiments, the bispecific fusion protein is tetravalent, comprising, for example, an immunoglobulin (e.g., IgG) with two binding sites for one antigen and two identical scFv for a second antigen. BsAbs composed of two scFv units in tandem have been shown to be a clinically successful bispecific antibody format. In some embodiments, BsAbs comprise two single chain variable fragments (scFvs) in tandem have been designed such that an scFv that binds a tumor antigen (e.g., A33) is linked with an scFv that engages T cells (e.g., by binding CD3). In this way, T cells are recruited to a tumor site such that they can mediate cytotoxic killing of the tumor cells. See e.g., Dreier et al., *J. Immunol.* 170:4397-4402 (2003); Bargou et al., *Science* 321:974-977 (2008)).

Recent methods for producing BsAbs include engineered recombinant monoclonal antibodies which have additional cysteine residues so that they crosslink more strongly than the more common immunoglobulin isotypes. See, e.g., FitzGerald et al., *Protein Eng.* 10(10):1221-1225 (1997). Another approach is to engineer recombinant fusion proteins linking two or more different single-chain antibody or antibody fragment segments with the needed dual specificities. See, e.g., Coloma et al., *Nature Biotech.* 15:159-163 (1997). A variety of bispecific fusion proteins can be produced using molecular engineering.

Bispecific fusion proteins linking two or more different single-chain antibodies or antibody fragments are produced in similar manner. Recombinant methods can be used to produce a variety of fusion proteins. In some certain embodiments, a BsAb according to the present technology comprises an immunoglobulin, which immunoglobulin comprises a heavy chain and a light chain, and an scFv. In some certain embodiments, the scFv is linked to the C-terminal end of the heavy chain of any A33 immunoglobulin disclosed herein. In some certain embodiments, scFvs are linked to the C-terminal end of the light chain of any A33 immunoglobulin disclosed herein. In various embodiments, scFvs are linked to heavy or light chains via a linker sequence. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the $V_H$ region of an A33 antibody. The resulting vector can be used to transfect an appropriate host cell, such as a mammalian cell for the expression of the bispecific fusion protein.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second antigen binding sites). In some embodiments, a linker is employed in a BsAb described herein based on specific properties imparted to the BsAb such as, for example, an increase in stability. In some embodiments, a BsAb of the present technology comprises a G4S linker (SEQ ID NO: 64). In some certain embodiments, a BsAb of the present technology comprises a (G4S)$_n$ linker (SEQ ID NO: 76), wherein n is 1, 2, 3, 4, 5, 6, 7, 8, 9, 10, 11, 12, 13, 14, 15 or more.

Fc Modifications. In some embodiments, the anti-A33 antibodies of the present technology comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., Nature, 406:267-273 (2000). Examples of positions within the Fc region that make a direct contact with an Fc receptor such as an FcγR, include amino acids 234-239 (hinge region), amino acids 265-269 (B/C loop), amino acids 297-299 (C7E loop), and amino acids 327-332 (F/G) loop.

In some embodiments, an anti-A33 antibody of the present technology has an altered affinity for activating and/or inhibitory receptors, having a variant Fc region with one or more amino acid modifications, wherein said one or more amino acid modification is a N297 substitution with alanine, or a K322 substitution with alanine.

Glycosylation Modifications. In some embodiments, anti-A33 antibodies of the present technology have an Fc region with variant glycosylation as compared to a parent Fc region. In some embodiments, variant glycosylation includes the absence of fucose; in some embodiments, variant glycosylation results from expression in GnT1-deficient CHO cells.

In some embodiments, the antibodies of the present technology, may have a modified glycosylation site relative to an appropriate reference antibody that binds to an antigen of interest (e.g., A33), without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach.

Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform (huA33-IgG1n) that lacks certain oligosaccharides including fucose and terminal N-acetylglucosamine may be produced in special CHO cells and exhibit enhanced ADCC effector function.

In some embodiments, the carbohydrate content of an immunoglobulin-related composition disclosed herein is modified by adding or deleting a glycosylation site. Methods for modifying the carbohydrate content of antibodies are well known in the art and are included within the present technology, see, e.g., U.S. Pat. No. 6,218,149; EP 0359096B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the carbohydrate content of an antibody (or relevant portion or component thereof) is modified by deleting one or more endogenous carbohydrate moieties of the antibody. In some certain embodiments, the present technology includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, Nat. Biotechnol. 17: 176-180; Davies et al., 2001, Biotechnol. Bioeng. 74:288-294; Shields et al., 2002, J. Biol. Chem. 277:26733-26740; Shinkawa et al., 2003, J. Biol. Chem. 278:3466-3473; U.S. Pat. No. 6,602,684; U.S. patent application Ser. No. 10/277,370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., International Patent Application Publication WO 00/061739; U.S. Patent Application Publication No. 2003/0115614; Okazaki et al., 2004, JIMB, 336: 1239-49.

Fusion Proteins. In one embodiment, the anti-A33 antibody of the present technology is a fusion protein. The anti-A33 antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-A33 antibodies. For instance, a region of additional amino acids, particularly charged amino acids, can be added to the N-terminus of the anti-A33 antibody to improve stability and persistence during purification from the host cell or subsequent handling and storage. Also, peptide moieties can be added to an anti-A33 antibody to facilitate purification. Such regions can be removed prior to final preparation of the anti-A33 antibody. The addition of peptide moieties to facilitate handling of polypeptides are familiar and routine techniques in the art. The anti-A33 antibody of the present technology can be fused to marker sequences, such as a peptide which facilitates purification of the fused polypeptide. In select embodiments, the marker amino acid sequence is a hexa-histidine peptide (SEQ ID NO: 65), such as the tag provided in a pQE vector (QIAGEN, Inc., Chatsworth, Calif.), among others, many of which are commercially available. As described in Gentz et al., Proc. Natl. Acad. Sci. USA 86: 821-824, 1989, for instance, hexa-histidine (SEQ ID NO: 65) provides for convenient purification of the fusion protein. Another peptide tag useful for purification, the "HA" tag, corresponds to an epitope derived from the influenza hemagglutinin protein. Wilson et al., Cell 37: 767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., *J. Biochem.* 270: 3958-3964, 1995.

Similarly, EP-A-O 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting or modifying the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.*, 270: 9459-9471, 1995.

Labeled Anti-A33 antibodies. In one embodiment, the anti-A33 antibody of the present technology is coupled with a label moiety, i.e., detectable group. The particular label or detectable group conjugated to the anti-A33 antibody is not a critical aspect of the technology, so long as it does not significantly interfere with the specific binding of the anti-A33 antibody of the present technology to the A33 protein. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^{3}H$, $^{14}C$, $^{35}S$, $^{125}I$, $^{121}I$, $^{131}I$, $^{112}In$, $^{99m}Tc$), other imaging agents such as microbubbles (for ultrasound imaging), $^{18}F$, $^{11}C$, $^{15}O$, (for Positron emission tomography), $^{99m}TC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene Oreg.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-A33 antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-A33 antibodies. In this case, antigen-coated particles are agglutinated by samples comprising the target antibodies. In this format, none of the components need be labeled and the presence of the target antibody is detected by simple visual inspection.

B. Identifying and Characterizing the Anti-A33 Antibodies of the Present Technology Methods for identifying and/or screening the anti-A33 antibodies of the present technology. Methods useful to identify and screen antibodies against A33 polypeptides for those that possess the desired specificity to A33 protein include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A et al., *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS,* 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells (PBMCs) in response to mitogens or mixed lymphocyte reaction can be measured using $^3$H-thymidine; (4) the phagocytic capacity of granulocytes, macrophages, and other phagocytes in PBMCs can be measured by placing PBMCs in wells together with labeled particles (Peters et al., *Blood,* 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-A33 antibodies of the present technology are selected using display of A33 peptides on the surface of replicable genetic packages. See, e.g., U.S. Pat. Nos. 5,514,548; 5,837,500; 5,871,907; 5,885,793; 5,969, 108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In some embodiments, anti-A33 antibodies of the present technology are selected using display of A33 peptides on the surface of a yeast host cell. Methods useful for the isolation of scF$_v$ polypeptides by yeast surface display have been described by Kieke et al., *Protein Eng.* 1997 November; 10(11): 1303-10.

In some embodiments, anti-A33 antibodies of the present technology are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

In certain embodiments, anti-A33 antibodies of the present technology are selected using tRNA display of A33 peptides. Methods useful for in vitro selection of ligands using tRNA display have been described by Merryman et al., *Chem. Biol.,* 9: 741-46, 2002.

In one embodiment, anti-A33 antibodies of the present technology are selected using RNA display. Methods useful for selecting peptides and proteins using RNA display libraries have been described by Roberts et al. *Proc. Natl. Acad. Sci. USA,* 94: 12297-302, 1997; and Nemoto et al., *FEBS Lett.,* 414: 405-8, 1997. Methods useful for selecting peptides and proteins using unnatural RNA display libraries have been described by Frankel et al., *Curr. Opin. Struct. Biol.,* 13: 506-12, 2003.

In some embodiments, anti-A33 antibodies of the present technology are expressed in the periplasm of gram negative bacteria and mixed with labeled A33 protein. See WO 02/34886. In clones expressing recombinant polypeptides with affinity for A33 protein, the concentration of the labeled A33 protein bound to the anti-A33 antibodies is increased and allows the cells to be isolated from the rest of the library as described in Harvey et al., *Proc. Natl. Acad. Sci.* 22: 9193-98 2004 and U.S. Pat. Publication No. 2004/0058403.

After selection of the desired anti-A33 antibodies, it is contemplated that said antibodies can be produced in large volume by any technique known to those skilled in the art, e.g., prokaryotic or eukaryotic cell expression and the like. The anti-A33 antibodies which are, e.g., but not limited to, anti-A33 hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of A33 Binding. In some embodiments, an A33 binding assay refers to an assay format wherein A33 protein and an anti-A33 antibody are mixed under conditions suitable for binding between the A33 protein and the anti-A33 antibody and assessing the amount of binding between the A33 protein and the anti-A33 antibody. The amount of binding is compared with a suitable control, which can be the amount of binding in the absence of the A33 protein, the amount of the binding in the presence of a non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of A33 protein binding to anti-A33 antibody are, e.g., nuclear magnetic resonance, fluorescence, fluorescence polarization, surface plasmon resonance (BIA-CORE® chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-A33 antibody is at least 1 percent greater than the binding observed in the absence of the candidate anti-A33 antibody, the candidate anti-A33 antibody is useful as an anti-A33 antibody of the present technology.

Measurement of A33 Neutralization. As used here, "A33 neutralization" refers to reduction of the activity and/or expression of A33 protein through the binding of an anti-A33 antibody. The capacity of anti-A33 antibodies of the present technology to neutralize A33 activity/expression may be assessed in vitro or in vivo using methods known in the art.

Uses of the Anti-A33 Antibodies of the Present Technology

General. The anti-A33 antibodies of the present technology are useful in methods known in the art relating to the localization and/or quantitation of an A33 protein (e.g., for use in measuring levels of the A33 protein within appropriate physiological samples, for use in diagnostic methods, for use in imaging the polypeptide, and the like). Antibodies of the present technology are useful to isolate an A33 protein by standard techniques, such as affinity chromatography or immunoprecipitation. An anti-A33 antibody of the present technology can facilitate the purification of natural immunoreactive A33 proteins from biological samples, e.g., mammalian sera or cells as well as recombinantly-produced immunoreactive A33 proteins expressed in a host system. Moreover, anti-A33 antibodies can be used to detect an immunoreactive A33 protein (e.g., in plasma, a cellular lysate or cell supernatant) in order to evaluate the abundance and pattern of expression of the immunoreactive polypeptide. The anti-A33 antibodies of the present technology can be used diagnostically to monitor immunoreactive A33 protein levels in tissue as part of a clinical testing procedure, e.g., to determine the efficacy of a given treatment regimen. As noted above, the detection can be facilitated by coupling (i.e., physically linking) the anti-A33 antibodies of the present technology to a detectable substance.

Detection of A33 protein. An exemplary method for detecting the presence or absence of an immunoreactive A33 protein in a biological sample involves obtaining a biological sample from a test subject and contacting the biological sample with an anti-A33 antibody of the present technology capable of detecting an immunoreactive A33 protein such that the presence of an immunoreactive A33 protein is detected in the biological sample. Detection may be accomplished by means of a detectable label attached to the antibody.

The term "labeled" with regard to the anti-A33 antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-A33 antibodies disclosed herein are conjugated to one or more detectable labels. For such uses, anti-A33 antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. inIn is an exemplary isotope where in vivo imaging is used since its avoids the problem of dehalogenation of the $^{125}$I or $^{131}$I-labeled A33-binding antibodies by the liver. In addition, this isotope has a more favorable gamma emission energy for imaging (Perkins et al, Eur. J. Nucl. Med. 70:296-301 (1985); Carasquillo et al., J Nucl. Med. 25:281-287 (1987)). For example, $^{111}$In coupled to monoclonal antibodies with 1-(P-isothiocyanatobenzyl)-DPTA exhibits little uptake in non-tumorous tissues, particularly the liver, and enhances specificity of tumor localization (Esteban et al., J. Nucl. Med. 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive A33 protein in a biological sample in vitro as well as in vivo. In vitro techniques for detection of an immunoreactive A33 protein include enzyme linked immunosorbent assays (ELISAs), Western blots, immunoprecipitations, radioimmunoassay, and immunofluorescence. Furthermore, in vivo techniques for detection of an immunoreactive A33 protein include introducing into a subject a labeled anti-A33 antibody. For example, the anti-A33 antibody can be labeled with a radioactive marker whose presence and location in a subject can be detected by standard imaging techniques. In one embodiment, the biological sample contains A33 protein molecules from the test subject.

Immunoassay and Imaging. An anti-A33 antibody of the present technology can be used to assay immunoreactive A33 protein levels in a biological sample (e.g., human plasma) using antibody-based techniques. For example, protein expression in tissues can be studied with classical immunohistological methods. Jalkanen, M. et al., J. Cell. Biol. 101: 976-985, 1985; Jalkanen, M. et al., J. Cell. Biol. 105: 3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}$I, $^{121}$I, $^{131}$I), carbon ($^{14}$C), sulfur ($^{35}$S), tritium ($^{3}$H), indium ($^{112}$In), and technetium ($^{99m}$Tc), and fluorescent labels, such as fluorescein, rhodamine, and green fluorescent protein (GFP), as well as biotin.

In addition to assaying immunoreactive A33 protein levels in a biological sample, anti-A33 antibodies of the present technology may be used for in vivo imaging of A33. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-A33 antibodies by labeling of nutrients for the relevant scFv clone.

An anti-A33 antibody which has been labeled with an appropriate detectable imaging moiety, such as a radioisotope (e.g., $^{131}$I $^{112}$In, $^{99m}$Tc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled anti-A33 antibody will then accumulate at the location of cells which contain the specific target polypeptide. For example, labeled anti-A33 antibodies of the present technology will accumulate within the subject in cells and tissues in which the A33 protein has localized.

Thus, the present technology provides a diagnostic method of a medical condition, which involves: (a) assaying the expression of immunoreactive A33 protein by measuring binding of an anti-A33 antibody of the present technology in cells or body fluid of an individual; (b) comparing the amount of immunoreactive A33 protein present in the sample with a standard reference, wherein an increase or decrease in immunoreactive A33 protein levels compared to the standard is indicative of a medical condition.

Affinity Purification. The anti-A33 antibodies of the present technology may be used to purify immunoreactive A33 protein from a sample. In some embodiments, the antibodies are immobilized on a solid support. Examples of such solid supports include plastics such as polycarbonate, complex carbohydrates such as agarose and SEPHAROSE®, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-S1AB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl)propionic acid can be employed as a means for cleaving a polypeptide from a solid support. (Brown et al., *Mol. Divers*, pp, 4-12 (1995); Rothschild et al., *Nucl. Acids Res.*, 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association. An antibody or polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of Anti-A33 Antibodies of the Present Technology

General. The anti-A33 antibodies of the present technology are useful in diagnostic methods. As such, the present technology provides methods using the antibodies in the diagnosis of A33 activity in a subject. Anti-A33 antibodies of the present technology may be selected such that they have any level of epitope binding specificity and very high binding affinity to an A33 protein. In general, the higher the binding affinity of an antibody the more stringent wash conditions can be performed in an immunoassay to remove nonspecifically bound material without removing target polypeptide. Accordingly, anti-A33 antibodies of the present technology useful in diagnostic assays usually have binding affinities of about $10^8$ $M^{-1}$, $10^9$ $M^{-1}$, $10^{10}$ $M^{-1}$, $10^{11}$ $M^{-1}$ or $10^{12}$ $M^{-1}$. Further, it is desirable that anti-A33 antibodies used as diagnostic reagents have a sufficient kinetic on-rate to reach equilibrium under standard conditions in at least 12 h, at least five (5) h, or at least one (1) hour.

Anti-A33 antibodies can be used to detect an immunoreactive A33 protein in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of A33 protein in a sample obtained from the subject. In certain embodiments, the sample is selected from the group consisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., an anti-A33 antibody or a population of anti-A33 antibodies immobilized to a solid phase, and another anti-A33 antibody or a population of anti-A33 antibodies in solution. Typically, the solution anti-A33 antibody or population of anti-A33 antibodies is labeled. If an antibody population is used, the population can contain antibodies binding to different epitope specificities within the target polypeptide. Accordingly, the same population can be used for both solid phase and solution antibody. If anti-A33 monoclonal antibodies are used, first and second A33 monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the A33 protein with the anti-A33 antibody, a sample is incubated for a period that usually varies from about 10 min to about 24 hr and is usually about 1 hr. A wash step is then performed to remove components of the sample not specifically bound to the anti-A33 antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive A33 protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the A33 protein in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-A33 antibodies can be joined to a linker molecule, such as biotin for attachment to a surface bound linker, such as avidin.

In some embodiments, the present disclosure provides an anti-A33 antibody of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the A33 antibodies of the present technology.

Macrocyclic chelates such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, such as radionuclides of gallium, yttrium and copper, respectively. Such metal-chelate complexes can be stabilized by tailoring the ring size to the metal of interest. Examples of other DOTA chelates include (i) DOTA-Phe-Lys(HSG)-D-Tyr-Lys(HSG)-NH$_2$; (ii) Ac-Lys(HSG)D-Tyr-Lys(HSG)-Lys(Tscg-Cys)-NH$_2$; (iii) DOTA-D-Asp-D-Lys(HSG)-D-Asp-D-Lys(HSG)-NH$_2$; (iv) DOTA-D-Glu-D-Lys(HSG)-D-Glu-D-Lys(HSG)-NH$_2$; (v) DOTA-D-Tyr-D-Lys(HSG)-D-Glu-D-Lys(HSG)-NH$_2$; (vi) DOTA-D-Ala-D-Lys(HSG)-D-Glu-D-Lys(HSG)-NH$_2$; (vii) DOTA-D-Phe-D-Lys(HSG)-D-Tyr-D-Lys(HSG)-NH$_2$; (viii) Ac-D-Phe-D-Lys(DOTA)-D-Tyr-D-Lys(DOTA)-NH$_2$; (ix) Ac-D-Phe-D-Lys(DTPA)-D-Tyr-D-Lys(DTPA)-NH$_2$, (x) Ac-D-Phe-D-Lys(Bz-DTPA)-D-Tyr-D-Lys(Bz-DTPA)-NH$_2$; (xi) Ac-D-Lys(HSG)-D-Tyr-D-Lys(HSG)-D-Lys(Tscg-Cys)-NH$_2$; (xii) DOTA-D-Phe-D-Lys(HSG)-D-Tyr-D-Lys(HSG)-D-Lys(Tscg-Cys)-NH$_2$; (xiii) (Tscg-Cys)-D-Phe-D-Lys(HSG)-D-Tyr-D-Lys(HSG)-D-Lys(DOTA)-NH$_2$; (xiv) Tscg-D-Cys-D-Glu-D-Lys(HSG)-D-Glu-D-Lys(HSG)-NH$_2$; (xv) (Tscg-Cys)-D-Glu-D-Lys(HSG)-D-Glu-D-Lys(HSG)-NH$_2$; (xvi) Ac-D-Cys-D-Lys(DOTA)-D-Tyr-D-Ala-D-Lys(DOTA)-D-Cys-NH$_2$; (xvii) Ac-D-Cys-D-Lys(DTPA)-D-Tyr-D-Lys(DTPA)-NH$_2$; (xviii) Ac-D-Lys(DTPA)-D-Tyr-D-Lys(DTPA)-D-Lys(Tscg-Cys)-NH$_2$; and (xix) Ac-D-Lys(DOTA)-D-Tyr-D-Lys(DOTA)-D-Lys(Tscg-Cys)-NH$_2$.

Other ring-type chelates such as macrocyclic polyethers, which are of interest for stably binding nuclides, such as $^{223}$Ra for RAIT are also contemplated.

B. Therapeutic Use of Anti-A33 Antibodies of the Present Technology

The immunoglobulin-related compositions (e.g., antibodies or antigen binding fragments thereof) of the present technology are useful for the treatment of A33 associated cancers. Such treatment can be used in patients identified as having pathologically high levels of the A33 (e.g., those diagnosed by the methods described herein) or in patients diagnosed with a disease known to be associated with such pathological levels. In one aspect, the present disclosure provides a method for treating an A33 associated cancer in a subject in need thereof, comprising administering to the subject an effective amount of an antibody (or antigen binding fragment thereof) of the present technology. Examples of cancers that can be treated by the antibodies of the present technology include, but are not limited to: colorectal cancer, Pseudomyxoma peritonei, appendiceal cancer, pancreatic cancer, and gastric cancer. The A33 associated cancer may be colorectal cancer with a MSI genotype or a MSS genotype. Additionally or alternatively, in some embodiments, the colorectal cancer is associated with a KRAS G12D mutation or a p53 mutation.

The compositions of the present technology may be employed in conjunction with other therapeutic agents useful in the treatment of A33 associated cancers. For example, the antibodies of the present technology may be separately, sequentially or simultaneously administered with at least one additional therapeutic agent-selected from the group consisting of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof.

The compositions of the present technology may optionally be administered as a single bolus to a subject in need thereof. Alternatively, the dosing regimen may comprise multiple administrations performed at various times after the appearance of tumors.

Administration can be carried out by any suitable route, including orally, intranasally, parenterally (intravenously, intramuscularly, intraperitoneally, or subcutaneously), rectally, intracranially, intrathecally, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies of the present technology comprise pharmaceutical formulations which may be administered to subjects in need thereof in one or more doses. Dosage regimens can be adjusted to provide the desired response (e.g., a therapeutic response).

Typically, an effective amount of the antibody compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-A33 antibodies, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-A33 antibodies may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 µg/mL to about 125 µg/mL, 100 µg/mL to about 150 µg/mL, from about 125 µg/mL to about 175 µg/mL, or from about 150 µg/mL to about 200 µg/mL. Alternatively, anti-A33 antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In another aspect, the present disclosure provides a method for detecting a tumor in a subject in vivo comprising (a) administering to the subject an effective amount of an antibody (or antigen binding fragment thereof) of the present technology, wherein the antibody is configured to localize to a tumor expressing A33 and is labeled with a radioisotope; and (b) detecting the presence of a tumor in the subject by detecting radioactive levels emitted by the antibody that are higher than a reference value. In some embodiments, the reference value is expressed as injected dose per gram (% ID/g). The reference value may be calculated by measuring the radioactive levels present in non-tumor (normal) tissues, and computing the average radioactive levels present in non-tumor (normal) tissues±standard deviation. In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{15}$Dy, $^{186}$Re, $^{188}$Re, $^{177}$Lu, and $^{67}$Cu. Examples of alpha particle-emitting isotopes include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Examples of Auger-emitters include $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, and $^{203}$Pb. In some embodiments of the method, nonspecific FcR-dependent binding in normal tissues is eliminated or reduced (e.g., via N297A mutation in Fc region, which results in aglycosylation). The therapeutic effectiveness of such an immunoconjugate may be determined by computing the area under the curve (AUC) tumor: AUC normal tissue ratio. In some embodiments, the immunoconjugate has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

PRIT. In one aspect, the present disclosure provides a method for detecting solid tumors in a subject in need thereof comprising (a) administering to the subject an effective amount of a complex comprising a radiolabeled DOTA hapten and a bispecific antibody of the present technology that binds to the radiolabeled DOTA hapten and an A33 antigen, wherein the complex is configured to localize to a solid tumor expressing the A33 antigen recognized by the bispecific antibody of the complex; and (b) detecting the presence of solid tumors in the subject by detecting radioactive levels emitted by the complex that are higher than a reference value. In some embodiments, the subject is human.

In another aspect, the present disclosure provides a method for selecting a subject for pretargeted radioimmunotherapy comprising (a) administering to the subject an effective amount of a complex comprising a radiolabeled DOTA hapten and a bispecific antibody of the present technology that binds to the radiolabeled DOTA hapten and an A33 antigen, wherein the complex is configured to localize to a solid tumor expressing the A33 antigen recognized by the bispecific antibody of the complex; (b) detecting radioactive levels emitted by the complex; and (c) selecting the subject for pretargeted radioimmunotherapy when the radioactive levels emitted by the complex are higher than a reference value. In some embodiments, the subject is human.

Examples of DOTA haptens include (i) DOTA-Phe-Lys(HSG)-D-Tyr-Lys(HSG)-NH$_2$; (ii) Ac-Lys(HSG)D-Tyr-Lys(HSG)-Lys(Tscg-Cys)-NH$_2$; (iii) DOTA-D-Asp-D-Lys(HSG)-D-Asp-D-Lys(HSG)-NH$_2$, (iv) DOTA-D-Glu-D-Lys(HSG)-D-Glu-D-Lys(HSG)-NH$_2$; (v) DOTA-D-Tyr-D-Lys(HSG)-D-Glu-D-Lys(HSG)-NH$_2$; (vi) DOTA-D-Ala-D-Lys(HSG)-D-Glu-D-Lys(HSG)-NH$_2$; (vii) DOTA-D-Phe-D-Lys(HSG)-D-Tyr-D-Lys(HSG)-NH$_2$; (viii) Ac-D-Phe-D-Lys(DOTA)-D-Tyr-D-Lys(DOTA)-NH$_2$; (ix) Ac-D-Phe-D-

Lys(DTPA)-D-Tyr-D-Lys(DTPA)-NH$_2$; (x) Ac-D-Phe-D-Lys(Bz-DTPA)-D-Tyr-D-Lys(Bz-DTPA)-NH$_2$; (xi) Ac-D-Lys(HSG)-D-Tyr-D-Lys(HSG)-D-Lys(Tscg-Cys)-NH$_2$; (xii) DOTA-D-Phe-D-Lys(HSG)-D-Tyr-D-Lys(HSG)-D-Lys (Tscg-Cys)-NH$_2$; (xiii) (Tscg-Cys)-D-Phe-D-Lys(HSG)-D-Tyr-D-Lys(HSG)-D-Lys(DOTA)-NH$_2$; (xiv) Tscg-D-Cys-D-Glu-D-Lys(HSG)-D-Glu-D-Lys(HSG)-NH$_2$; (xv) (Tscg-Cys)-D-Glu-D-Lys(HSG)-D-Glu-D-Lys(HSG)-NH$_2$; (xvi) Ac-D-Cys-D-Lys(DOTA)-D-Tyr-D-Ala-D-Lys(DOTA)-D-Cys-NH$_2$; (xvii) Ac-D-Cys-D-Lys(DTPA)-D-Tyr-D-Lys (DTPA)-NH$_2$; (xviii) Ac-D-Lys(DTPA)-D-Tyr-D-Lys (DTPA)-D-Lys(Tscg-Cys)-NH$_2$; (xix) Ac-D-Lys(DOTA)-D-Tyr-D-Lys(DOTA)-D-Lys(Tscg-Cys)-NH$_2$ and (xx) DOTA. The radiolabel may be an alpha particle-emitting isotope, a beta particle-emitting isotope, or an Auger-emitter. Examples of radiolabels include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{195m}$Os, $^{192}$Ir, $^{201}$Tl, $^{203}$Pb, $^{68}$Ga, $^{227}$Th, or $^{64}$Cu.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having an A33-positive cancer such as colorectal cancer, Pseudomyxoma peritonei, appendiceal cancer, pancreatic cancer, and gastric cancer.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally or intranasally. In certain embodiments, the complex is administered into the cerebral spinal fluid or blood of the subject.

In some embodiments of the methods disclosed herein, the radioactive levels emitted by the complex are detected between 2 to 120 hours after the complex is administered. In certain embodiments of the methods disclosed herein, the radioactive levels emitted by the complex are expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, *J Nucl Med.* 45(9):1431-4 (2004). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with an A33-positive cancer comprising (a) administering an effective amount of an anti-DOTA bispecific antibody of the present technology to the subject, wherein the anti-DOTA bispecific antibody is configured to localize to a tumor expressing an A33 antigen target; and (b) administering an effective amount of a radiolabeled-DOTA hapten to the subject, wherein the radiolabeled-DOTA hapten is configured to bind to the anti-DOTA bispecific antibody. In some embodiments, the subject is human.

The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the radiolabeled-DOTA hapten is administered after a time period that may be sufficient to permit clearance of unbound anti-DOTA bispecific antibody.

The radiolabeled-DOTA hapten may be administered at any time between 1 minute to 4 or more days following administration of the anti-DOTA bispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled-DOTA hapten may be administered at any time after 4 or more days following administration of the anti-DOTA bispecific antibody.

Additionally or alternatively, in some embodiments, the method further comprises administering an effective amount of a clearing agent to the subject prior to administration of the radiolabeled-DOTA hapten. A clearing agent can be any molecule (dextran or dendrimer or polymer) that can be conjugated with C825-hapten. In some embodiments, the clearing agent is no more than 2000 kD, 1500 kD, 1000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, or 5kD. In some embodiments, the clearing agent is a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.).

In some embodiments, the clearing agent and the radiolabeled-DOTA hapten are administered without further administration of the anti-DOTA bispecific antibody of the present technology. For example, in some embodiments, an anti-DOTA bispecific antibody of the present technology is administered according to a regimen that includes at least one cycle of: (i) administration of the anti-DOTA bispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Additionally or alternatively, in some embodiments of the method, the anti-DOTA bispecific antibody and/or the radiolabeled-DOTA hapten is administered intravenously, intramuscularly, intraarterially, intrathecally, intracapsularly, intraorbitally, intradermally, intraperitoneally, transtracheally, subcutaneously, intracerebroventricularly, orally or intranasally.

In one aspect, the present disclosure provides a method for increasing tumor sensitivity to radiation therapy in a subject diagnosed with an A33-positive cancer comprising administering to the subject an effective amount of a complex comprising a radiolabeled-DOTA hapten and a bispecific antibody of the present technology that recognizes and binds to the radiolabeled-DOTA hapten and an A33 antigen target, wherein the complex is configured to localize to a tumor expressing the A33 antigen target recognized by the bispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments, the subject is human.

In another aspect, the present disclosure provides a method for treating cancer in a subject in need thereof comprising (a) administering an effective amount of an anti-DOTA bispecific antibody of the present technology to the subject, wherein the anti-DOTA bispecific antibody is configured to localize to a tumor expressing an A33 antigen target; and (b) administering an effective amount of a radiolabeled-DOTA hapten to the subject, wherein the radiolabeled-DOTA hapten is configured to bind to the anti-DOTA bispecific antibody. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the radiolabeled-DOTA hapten is administered after a time period that may be sufficient to permit clearance of unbound anti-DOTA bispecific antibody. In some embodiments, the subject is human.

Accordingly, in some embodiments, the method further comprises administering an effective amount of a clearing agent to the subject prior to administration of the radiolabeled-DOTA hapten. The radiolabeled-DOTA hapten may be administered at any time between 1 minute to 4 or more days following administration of the anti-DOTA bispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled-DOTA hapten may be administered at any time after 4 or more days following administration of the anti-DOTA bispecific antibody.

The clearing agent may be a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.). In some embodiments, the clearing agent and the radiolabeled-DOTA hapten are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Also provided herein are methods for treating cancer in a subject in need thereof comprising administering to the subject an effective amount of a complex comprising a radiolabeled-DOTA hapten and a bispecific antibody of the present technology that recognizes and binds to the radiolabeled-DOTA hapten and an A33 antigen target, wherein the complex is configured to localize to a tumor expressing the A33 antigen target recognized by the bispecific antibody of the complex. The therapeutic effectiveness of such a complex may be determined by computing the area under the curve (AUC) tumor: AUC normal tissue ratio. In some embodiments, the complex has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Toxicity. Optimally, an effective amount (e.g., dose) of anti-A33 antibody described herein will provide therapeutic benefit without causing substantial toxicity to the subject. Toxicity of the anti-A33 antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-A33 antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Formulations of Pharmaceutical Compositions. According to the methods of the present technology, the anti-A33 antibody can be incorporated into pharmaceutical compositions suitable for administration. The pharmaceutical compositions generally comprise recombinant or substantially purified antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, Pa. $18^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-A33 antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. An anti-A33 antibody named in this technology can be present in unsalified or unesterified form, or in salified and/or esterified form, and the naming of such anti-A33 antibody is intended to include both the original (unsalified and unesterified) compound and its pharmaceutically-acceptable salts and esters. Also, certain embodiments of the present technology can be present in more than one stereoisomeric form, and the naming of such anti-A33 antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-A33 antibody, use thereof in the compositions is contemplated. Supplementary active compounds can also be incorporated into the compositions.

A pharmaceutical composition of the present technology is formulated to be compatible with its intended route of administration. The anti-A33 antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-A33 antibody can optionally be administered in combination with other agents that are at least partly effective in treating various A33 associated cancers.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating an anti-A33 antibody of the present technology in the required amount in an appropriate solvent with one or a combination of ingredients enumerated above, as required, followed by filtered sterilization. Generally, dispersions are prepared by incorporating the anti-A33 antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-A33 antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-A33 antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-A33 antibody is formulated into ointments, salves, gels, or creams as generally known in the art.

The anti-A33 antibody can also be prepared as pharmaceutical compositions in the form of suppositories (e.g., with conventional suppository bases such as cocoa butter and other glycerides) or retention enemas for rectal delivery.

In one embodiment, the anti-A33 antibody is prepared with carriers that will protect the anti-A33 antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

C. Kits

The present technology provides kits for the detection and/or treatment of A33 associated cancers, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of A33 associated cancers. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive A33 protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, or bispecific anti-A33 antibodies of the present technology (or antigen binding fragments thereof) capable of binding an A33 protein in a biological sample; means for determining the amount of the A33 protein in the sample; and means for comparing the amount of the immunoreactive A33 protein in the sample with a standard. One or more of the anti-A33 antibodies may be labeled. The kit components, (e.g., reagents) can be packaged in a suitable container. The kit can further comprise instructions for using the kit to detect the immunoreactive A33 protein.

For antibody-based kits, the kit can comprise, e.g., 1) a first antibody, e.g. a humanized, chimeric or bispecific A33 antibody of the present technology (or an antigen binding fragment thereof), attached to a solid support, which binds to an A33 protein; and, optionally; 2) a second, different antibody which binds to either the A33 protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of an A33 protein in vitro or in vivo, or for treatment of A33 associated cancers in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative A33 antibodies of the present technology. The following Examples demonstrate the production of chimeric, humanized, and bispecific antibodies of the present technology, and characterization of their binding specificities and in vivo biological activities.

Example 1: Materials and Methods for Generating and Characterizing the Anti-A33 Antibodies of the Present Technology Cell lines and human white cells. Cell lines LS174T, Colo205, SNU-16 and 293T cells were purchased from ATCC® (Manassas, Va.); SW1222 was ECACC (Salisbury, United Kingdom). All cells were authenticated by STR typing. Cells were maintained in RPMI medium supplemented with 10% FBS (Sigma, St. Louis, Mo.), 0.03% L-Glutamine (Gibco Laboratories, Gaithersburg, Md.) and Pen/Strep (Gibco Laboratories, Gaithersburg, Md.). Buffy coats from healthy donors were purchased from New York Blood Center (New York City, N.Y.) and human PBMCs were isolated by Ficoll gradient of Buffy coats.

Establishment of luciferase expressing cell lines. 293T cells were first transfected with a retroviral construct containing luciferase and GFP genes using POLYJET™ transfection reagent (SIGNAGEN LABORATORIES®, Rockville, Md.) according to the manufacturer's instructions. Thirty-six hours later virus-containing supernatant was collected and filtered with a 0.45 μm filter. Two milliliter filtered supernatant was aliquoted into each well of a 12 well plate pre-coated with Retronectin (CLONTECH® Laboratories, Mountain View, Calif.). The plate was spun at 3500 rpm at 4° C. for 45 min. The process was repeated 2 to 3 times. After spinning, the plate was washed once with PBS, after which $0.2 \times 10^6$ tumor cells were plated and incubated at 37° C. Spinoculation was repeated once more after 24 hours. Cells were then further incubated for at least 48 hours before sorting for GFP expressing cells. For cell sorting, transduced cells were sorted into at least 4 plates of 96-well plate at 1 cell/well density and incubated for 2 weeks before colony picking. Picked colonies were assessed and selected based on luciferase, GFP and GPA33 expression in comparison to parental cell lines.

SEC-HPLC analysis. Size and purity of huA33-BsAb was analyzed using HPLC system (Shimadzu Scientific Instruments Inc., Columbia, Md.). Monomeric species were identified using a molecular weight standard (Bio-Rad Laboratories, Hercules, Calif.) and percent monomer was calculated based on the relative area under curve (AUC) of different non-buffer peaks.

Humanization of murine A33. Using CDR grafting, mouse A33 was humanized as $IgG_1$. Two different VH and VL sequences were combined to generate 4 different humanized A33 antibodies. Binding kinetics was compared with that of chimeric antibody chA33 using Surface Plasmon resonance (SPR) analysis. The heavy chain sequence is SEQ ID NO: 6 (3A3-H2) and the light chain sequence is SEQ ID NO: 10 (3A3-L2).

The heavy chain sequence including the leader sequence is (SEQ ID NO: 55)
MGWSCIILFLVATATGEVQLVESGGGLVKPGGSLRLSCAASGFAFSTYDM

SWVRQAPGKRLEWVATISSGGSYTYYLDSVKGRFTISRDNAKNSLYLQMN

SLRAEDTAVYYCAPTTVVPFAYWGQGTLVTVSS and the light chain sequence including the leader sequence is (SEQ ID NO: 56)
MGWSCIILFLVATATGDIQMTQSQSSLSTSVGDRVTITCKASQNVRTVVA

WYQQKPGKSPKTLIYLASNRHTGVPSRFSGSGSGTEFTLTISNVQPEDFA

DYFCLQHWSYPLTFGSGTKLEIKR.

The underlined sequence corresponds to the leader sequence.

SPR analysis. Human GPA33 (Novoprotein, Summit, N.J.) was immobilized on CM5 chips. Five concentrations of 2-fold serially diluted huA33 IgG1 or huA33-BsAbs (starting at 20 nM) were flowed over the chip using a BIACORE® T100 system (GE Healthcare, Chicago, Ill.). Binding kinetics of huA33 were measured at 25° C. and binding kinetics of huA33-BsAbs were measured at both 25° C. and 37° C. The sensorgrams were fitted with 1:1 binding model for both to derive kinetic parameters.

Generation of huA33-BsAb bispecific antibody. HuA33-BsAb was constructed by fusing the humanized OKT3 scFv onto the C-terminus of the light chain of huA33 antibody via a $(G4S)_3$ linker (SEQ ID NO: 66) as previously described in Xu H et al., *Cancer Immunology Research* 3:266-277 (2015) and Lopez-Albaitero A et al., *OncoImmunology* 6:e1267891 (2017). N297A and K322A mutations were introduced in the Fc region of the antibody to eliminate FcR and complement binding activities, respectively (Shields R L et al., *Journal of Biological Chemistry* 276:6591-6604 (2001); Idusogie E E et al., *Journal of Immunology* 164:4178-4184 (2000)). The DNA construct was then transfected into CHO-S cells and stable clones were selected for high levels of antibody production. For larger-scale antibody purification, the selected stable clone was expanded in shaker flasks. Bispecific antibody was purified from supernatant using one-step protein A affinity chromatography.

T-cell dependent cytotoxicity (TDCC) assays. Cytotoxicity assays were performed using both $^{51}$Cr-release assay and Pierce LDH-release assay (Thermo Fisher Scientific, Cambridge, Mass.). For both assays, T cells activated by exposure to anti-CD3/anti-CD28 Dynabeads for 14 days were subsequently used as effector cells, excepted for sorted cells from PBMCs, which were used for TDCC assay without prior stimulation. $^{51}$Cr assay was performed as previously described in Cheng M et al., *International Journal of Cancer* 136:476-486 (2015). LDH assay was conducted according to the manufacturer's instructions with the following modifications. Briefly, for each assay well of a 96-well round-bottom plate, $1.5 \times 10^4$ target cells were incubated with variable number of effector cells, depending on the intended E:T ratios. Antibodies were then added at different dilutions and the plates were incubated at 37° C. for 16 hours. Each condition was done in triplicates. Supernatant was then transferred to a flat bottom plate with reaction substrate and incubated for 30 min before reading at 490 nm, with 680 nm as a reference wavelength. $EC_{50}$ values were calculated by fitting the curves to a 4-parameter nonlinear regression model using GraphPad Prism.

Cytokines and cytolytic molecules release assay. T cells were purified from PBMCs using pan T cell isolation kit (Miltenyi Biotec, Cambridge, Mass.). Target and control tumor cells were incubated with $2 \times 10^6$ cells/well at an effector to target ratio of 5:1 in 24-well plates in triplicates, with 2 ml total volume per well. Culture supernatants were collected at 24 hours, 48 hours, 72 hours and 96 hours and cytokine levels were measured with flow cytometry using LEGENDplex™ human CD8/NK Panel (BIOLEGEND®, San Diego, Calif.) according to the manufacturer's protocol.

T cell proliferation assay. Fresh PBMCs from healthy donors were labeled with 2.5 nM CFSE (Life Technologies Corp., Carlsbad, Calif.) for 5 min at room temperature, followed by neutralization using PBS containing 5% FBS. Target cells were then incubated with labeled PBMCs under different conditions at 37° C. before analyzing the expression of surface activation markers and T cell proliferation at 24 hours and 96 hours.

In vivo tumor therapy. For subcutaneous (s.c.) tumor models, LS174T, Colo205 or SNU16 cells were combined with fresh PBMCs at a 1:1 ratio, mixed with MATRIGEL® (volume of cell:gel=1:2), and implanted (100 µl/mouse) at the flank of Balb/c Rag2$^{-/-}$IL2Rγ$^{-/-}$ (DKO) mice (now commercially available from Taconic as CIEA BRG mice). Treatment started after confirmation of tumor presence with a BIW schedule at 100 µg/mouse and continued for 3-4 weeks. Tumor growth was monitored by weekly measurement of tumor volume using a caliper or a digital device Peira TM900 Scanner (Peira Scientific Instruments, Turnhout, Belgium).

For intraperitoneal (i.p.) tumor models, luciferase expressing LS174T-luc or SW1222-luc cells were resuspended in RPMI medium and injected intraperitoneally into DKO mice. Human effector cells were supplied as activated T cells and injected intravenously. Mice were treated with 2-3 weekly cycles of antibody-T cell-antibody regimen, with each component separated by 3-4 days. Growth of tumors was followed weekly by measuring luminescence signals on an IVIS Spectrum in vivo imaging system (PERKINELMER® Inc., Waltham, Mass.) after injection of 3.3 mg/mouse of luciferin. Luminescence was analyzed and quantified using Living Image Software (PERKINELMER®-Inc., Waltham, Mass.).

Antibodies and flow cytometry. Antibodies anti-hCD25-PE, anti-CD69-PE, anti-hCD8-APC, anti-hCD45-PECy7, anti-hCD4-PE, anti-hCD4-BV421, anti-hCD62L-PercpCy5.5, anti-hPD1-BV421, anti-hCD45RO-PECy7, were purchased from BIOLEGEND® (San Diego, Calif.). Goat anti-human IgG-PE was purchased from SouthernBiotech (Birmingham, Ala.). Streptavidin-PE, anti-hCD4-APC and anti-hCD25-APC were purchased from BD Biosciences (San Jose, Calif.). All FACS analysis was done using FACSCalibur or LSRII system (BD Biosciences, San Jose, Calif.) and analyzed using FlowJo (FLOWJO, Ashland, Oreg.).

Figure 13:
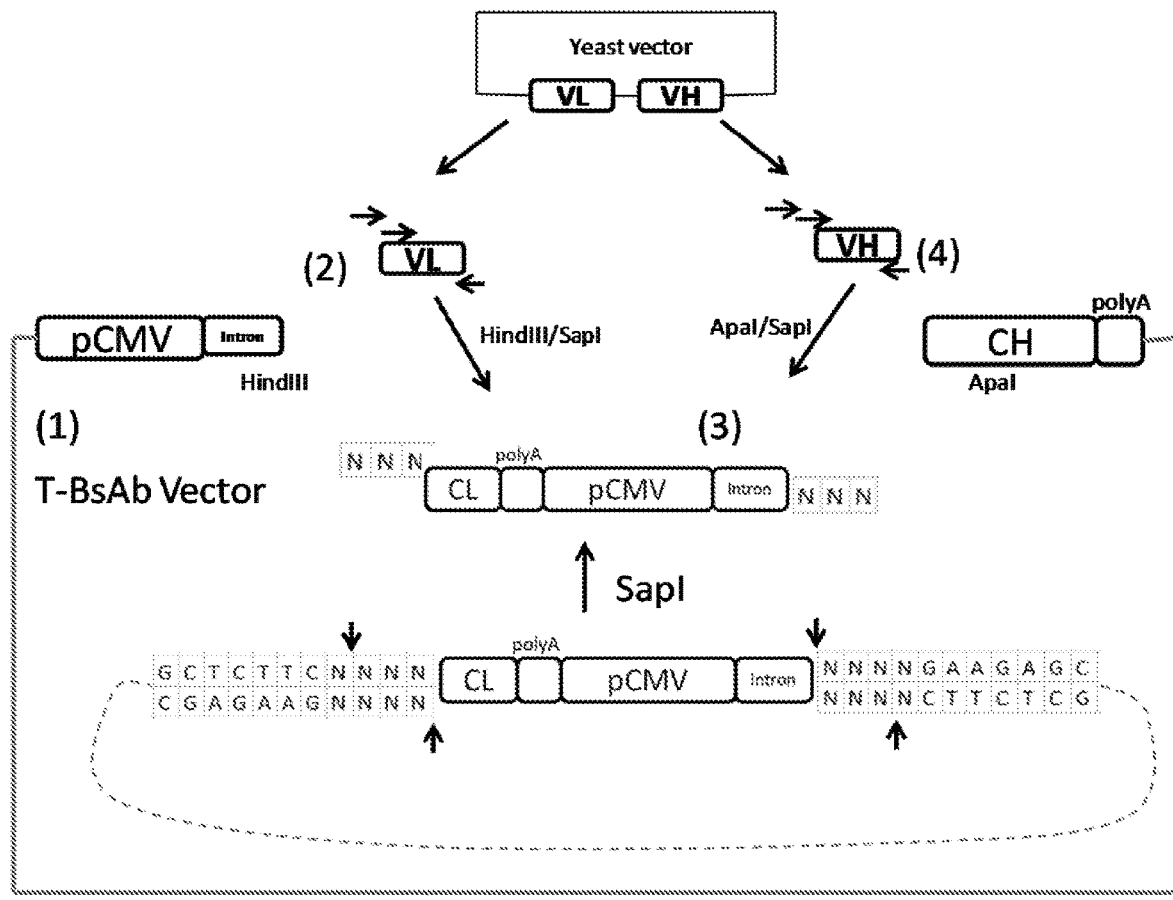
FIG. 13 shows the strategy for rapid reformation of scFv to huA33-BsAb format. Expression vector (1) was linearized with HindIII/ApaI. Promoter fragment (3) was prepared from SapI digested promoter-containing vector. Both vector and promoter fragment could be prepared in large amounts for higher throughput cloning. VH (4) and VL (2) were amplified directly from yeast with two 5' primers to add the leader sequences and digested with HindIII/SapI (VL) or ApaI/SapI (VH). The 4 fragments were ligated in a one-step reaction.

Affinity maturation using yeast display. Parental huA33 was converted into scFv format with a 20 amino acid (G4S)$_4$ linker (SEQ ID NO: 67) and cloned into a yeast display vector. HuA33 scFv was randomly mutated using GeneMorph II mutagenesis kit (Agilent Technologies, Santa Clara, Calif.). PCR products were electroporated together with linearized vector into yeast and the library was subjected to 4 rounds of sorting using biotinylated GPA33. Individual clones from the last round were PCR amplified and sequenced to analyze the mutation pattern. Conversion of selected scFv clones into huA33-BsAb format was done using a one-step 4-fragment ligation method with 50 ng linearized vector and a 1:3 vector to insert molar ratio for the other 3 components. Ligation was done with Rapid DNA ligation kit (Thermo Fisher Scientific, Cambridge, Mass.) at room temperature for 1 hour. Type II restriction enzyme SapI (New England Biolabs, Ipswich, Mass.) was used to ensure seamless linkage among the different components (FIG. 13). Selected clones were transiently expressed using EXPI293™ expression system (Thermo Fisher Scientific, Cambridge, Mass.) according to the manufacturer's instructions. Supernatant from EXPI293™-cells after 4-5 days of culture in shaking flasks was used to purify antibodies using MABSELECT™ SURE™ (GE Healthcare, Chicago, Ill.) and dialyzed against pH 8.0 citrate buffer in dialysis membrane (Spectrum Laboratories, Inc., Rancho Dominguez, Calif.).

Statistical analysis. Significance (p<0.05) was tested using Student's t-test.

Figure 19:
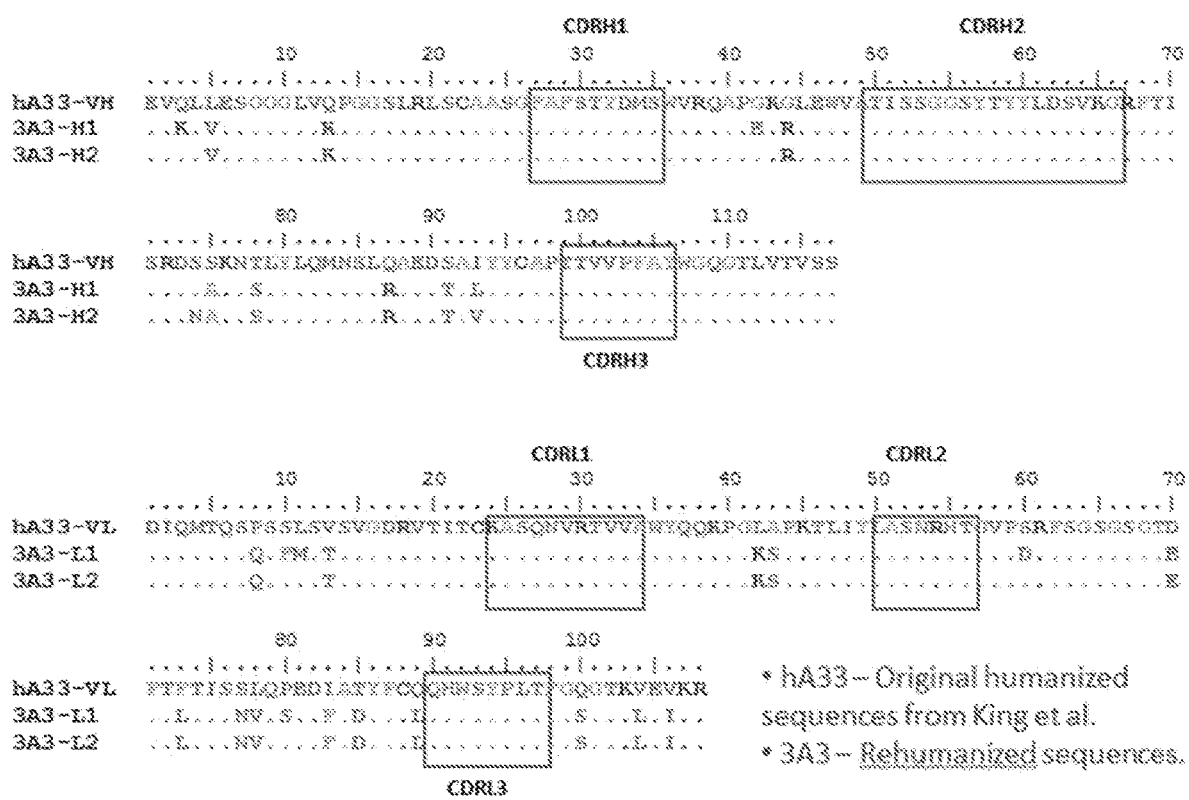
FIG. 19 shows the alignment of the original humanized sequences hA33 from King et al. (1995) supra, versus the newly rehumanized huA33 (3A3) sequences (SEQ ID NOS 70-75, respectively, in order of appearance).

Example 2: Structure and Binding Affinity of the Humanized Anti-A33 Antibodies of the Present Technology FIG. 14 shows the amino acid sequences of the $V_H$ and $V_L$ domains of the murine A33 antibody and their corresponding homologous human sequences (SEQ ID NOs: 1-4). The amino acid sequences of the $V_H$ and $V_L$ domains of 3A3-H1/L1, 3A3-H1/L2, 3A3-12/L1 and 3A3-H2/L2 humanized A33 antibodies of the present technology are shown in FIG. 15 and FIG. 17. The cDNA sequences of the $V_H$ and $V_L$ domains of 3A3-H1/L1, 3A3-H1/L2, 3A3-H2/L1 and 3A3-H2/L2 humanized A33 antibodies are shown in FIG. 16 and FIG. 18. FIG. 19 shows the alignment of the original humanized amino acid sequences hA33 from King et al. (1995) supra, versus the newly rehumanized huA33 (3A3) amino acid sequences.

FIG. 24 shows the amino acid sequences of the light chain and heavy chain of the chimeric chA33-IgG1, which correspond to SEQ ID NO: 13 and SEQ ID NO: 14 respectively. FIG. 25 shows the amino acid and cDNA sequences of the heavy chain of huA33-IgG1 (H2L2), which correspond to SEQ ID NO: 15 and SEQ ID NO: 16 respectively. FIG. 26 shows the amino acid and cDNA sequences of the light chain of huA33-IgG1 (H2L2), which correspond to SEQ ID NO: 17 and SEQ ID NO: 18 respectively.

Figure 9:
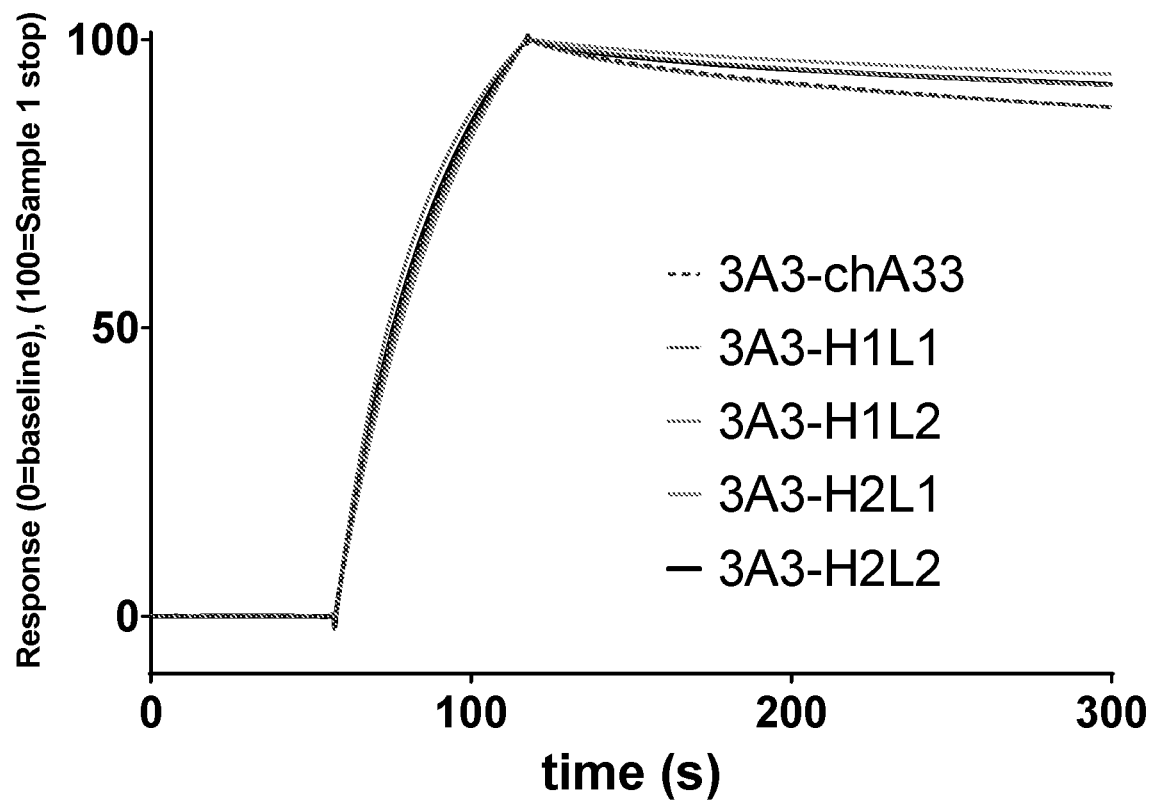
FIG. 9 shows the SPR analysis of 4 versions of humanized A33. All antibodies comprised a IgG1 constant domain. 3A3-HIL1, 3A3-HIL2, 3A3-H2L1 and 3A3-H2L2 were 4 versions of humanized 3A3. 3A3-chA33 was chimeric 3A3.
Figure 21:
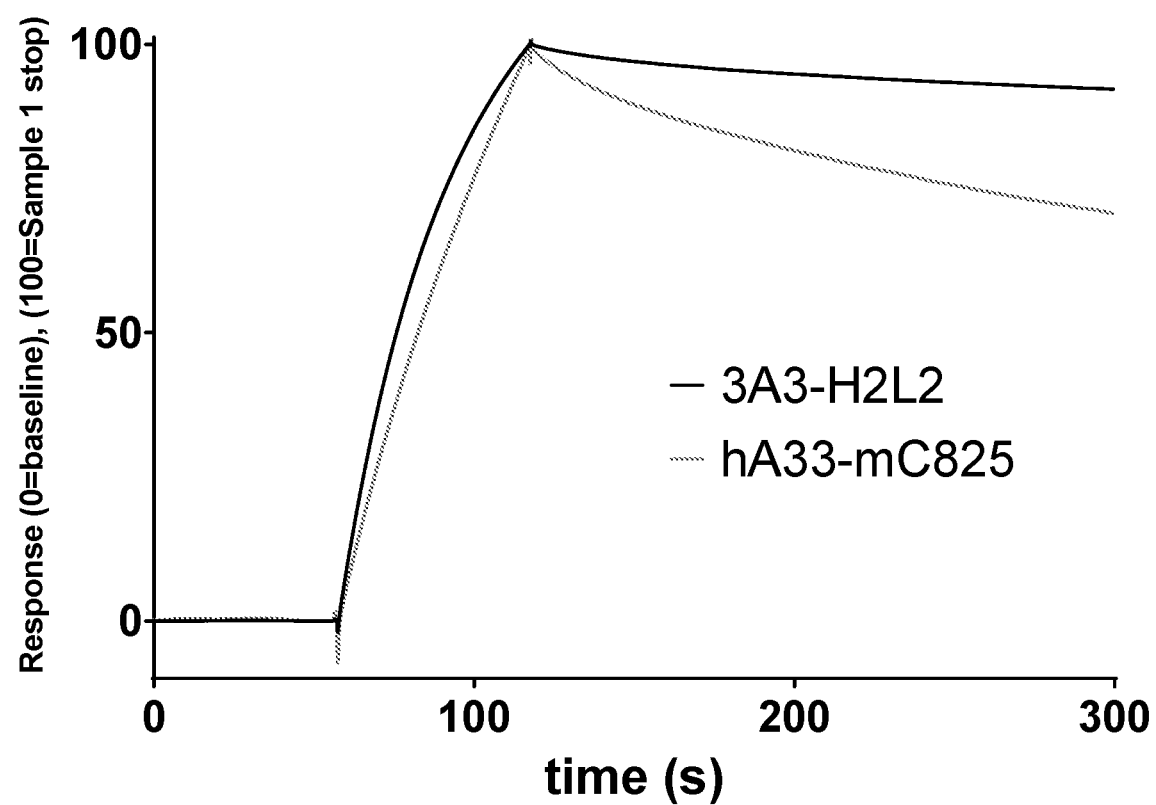
FIG. 21 shows the binding kinetics of the original humanized hA33 (in hA33-mC825 bispecific format as described in Cheal et al, *Eur. J. Nucl. Med. Mol. Imaging*, 43:925-937 (2016) vs. huA33 (3A3-H2L2) assayed on GPA33 recombinant protein using SPR (BIACORE®-T100). The original humanized hA33 lost considerable affinity compared to huA33.

When compared to chimeric A33, all four newly humanized A33 antibodies have slightly improved $k_{off}$ in binding to immobilized GPA33 in SPR analysis (FIG. 9 and FIG. 20). Based on the $K_D$, stability at 37° C. and T20 humanness score, the H2L2 huA33 clone was chosen for further development. See FIG. 23. FIG. 21 and FIG. 22 demonstrate that the original humanized hA33 (hA33-mC825 BsAb) described in Cheal et al. (2016) supra exhibited a considerable reduction in binding affinity compared to huA33-H2L2.

These results demonstrate that the antibodies of the present technology or antigen binding fragments thereof, specifically bind to A33 antigen with high binding affinity. Accordingly, the immunoglobulin-related compositions disclosed herein are useful for detecting A33 protein in a sample.

Example 3: Structure and Binding Affinity of T-Cell Engaging HuA33-BsAb Antibodies of the Present Technology The huA33 antibody was reformatted into bispecific format by fusing scFv of humanized OKT3 to the C-terminus of light chain via a flexible GS linker (FIG. 1(A)). The DNA construct was used to establish a CHO-S stable cell line and huA33-BsAb was purified from the supernatant. Protein yield using protein A chromatography was 50 mg/L to 100 mg/L without extensive optimization. Similar yields were observed using EXPI293™ transient expression system (data not shown). One-step protein A purification routinely produced protein with purity above 90%, as measured by SEC-HPLC. Four cycles of freeze-thaw did not cause noticeable changes in SEC-HPLC profile (data not shown). After incubating the molecule at 37° C. for 4 weeks, there was only a minimal decrease in the percentage of monomers, as shown in FIG. 1(B). These data suggest that huA33-BsAb had good solubility, purity and thermal stability, all of which are critical characteristics for further downstream development.

FIG. 27 shows the amino acid and cDNA sequences of the heavy chain of T-cell engaging huA33-BsAb bispecific antibodies, which correspond to SEQ ID NO: 19 and SEQ ID NO: 20 respectively. FIG. 28 shows the amino acid and cDNA sequences of the light chain of T-cell engaging huA33-BsAb bispecific antibodies, which correspond to SEQ ID NO: 21 and SEQ ID NO: 22 respectively. FIG. 29 shows a summary of potential modifications to the T-cell engaging huA33-BsAb bispecific antibodies disclosed herein.

The avidities of huA33-BsAb towards GPA33 at both 25° C. and 37° C. were measured using GPA33 immobilized CM5 chips. As shown in FIG. 1(C), huA33-BsAb bound GPA33 with a high apparent affinity of around 0.2 nM, which is slightly lower than the 0.13 nM value observed for parental huA33. FACS analysis of a panel of cell lines derived from different cancers showed that huA33-BsAb stained colon cancer cell lines and one gastric cancer cell line but not GPA33(-) neuroblastoma cell line IMR32, osteosarcoma cell line TC32 or melanoma cell line SKMEL5 (FIG. 1(D) and FIG. 10), demonstrating that huA33-BsAb retained the specificity of parental antibody A33 in binding to target antigens on colon cancer cells and a subset of gastric cancer cells. Staining of activated T cells also showed that huA33-BsAb bound to CD3 on T cell surface. See FIG. 1(D).

These results demonstrate that the antibodies of the present technology or antigen binding fragments thereof, specifically bind to A33 antigen with high binding affinity. Accordingly, the immunoglobulin-related compositions disclosed herein are useful for detecting A33 protein in a sample.

Example 4: Biological Activity of T-Cell Engaging HuA33-BsAb Antibodies of the Present Technology HuA33-BsAb activated and induced cell cycle entry of fresh T cells. To test the ability of huA33-BsAb to activate unstimulated T cells, CFSE-labeled PBMCs were mixed with Colo205 cells at an E:T ratio of 5, and cultured in the presence of huA33-BsAb (1 µg/ml). huA33-C825 that carried an irrelevant scFv (Cheal S M et al., *Eur J Nucl Med Mol Imaging* 43:925-37 (2016)) instead of the anti-CD3 $scF_v$, as well as an irrelevant T cell engaging-BsAb antibody L1CAM-BsAb against the antigen L1CAM (L1CAM×CD3) that did not bind to L1CAM(-) Colo205 by FACS were used as negative controls.

After 24 and 96 hours, cells were stained with different T cell activation markers to assess T cell activation status and proliferation. As early as 24 hours, huA33-BsAb caused activation of both CD4(+) and CD8(+) T cells, as shown by the upregulation of CD25 and CD69 markers on cell surface (FIG. 2(A)). In contrast, huA33-C825 and L1CAM-BsAb caused only minimal upregulation of CD25. L1CAM-BsAb did increase the expression of CD69, especially in CD4(+) T cells, possibly due to the expression of L1CAM on T cells. Similarly, PD-1 upregulation was observed after 24 hours and persisted until 96 hours (FIG. 11(A)). Cell division, as measured by CFSE dye dilution, was observed in both CD4(+) and CD8(+) T cells after 96 hours (FIG. 2(B)). CD8(+) T cells showed higher cell division cycles, suggesting that CD8(+) T cells divided faster than CD4(+) T cells (FIG. 2(C)). Control antibodies huA33-C825 did not stimulate significant amount of cell division in either T cell subset, confirming the requirement of CD3 activation for T cell division. A low level of cell division was induced by L1CAM-BsAb, consistent with the low level of activation observed above. When GPA33(-) SKMEL5 target cells were used, huA33-BsAb did not activate T cells (FIG. 11(B)). These results demonstrate that activation of T cells by huA33-BsAb is dependent on the presence of cognate antigens on tumor cells. We also observed that cell division was associated with expansion of CD45RO(+) effector/memory cells (FIG. 2(D)), suggesting the importance of this subset in mediating T-BsAb activity which was confirmed below. These assays were repeated using a different colon cancer cell line LS174T with similar conclusions (FIG. 11(C)).

To determine if T cells can be activated in vivo, an in vivo proliferation assay was conducted by mixing CFSE-labeled PBMCs with Colo205 cells and the mixture was implanted subcutaneously onto DKO mice. huA33-BsAb was injected intravenously the next day and the tumors were isolated after another 4 days and analyzed by FACS. As shown in FIG. 2(E), around 25% of CD4(+) and CD8(+) T cells upregulated CD25 expression while undergoing cell division (progressive halving of CFSE fluorescence), suggesting that huA33-BsAb was also able to stimulate T cell activation and proliferation in vivo.

HuA33-BsAb induced secretion of inflammatory cytokines and cytolytic molecules. The secreted cytokine profile of T cells activated by huA33-BsAb in the presence of target tumors was examined. Total T cells were purified from PBMCs and cultured in the presence of Colo205 tumor cells at an effector to target ratio of 5:1. To estimate nonspecific activation, SKMEL5 cells were used as a negative control. Cell culture supernatants were collected daily over 4 days and the levels of cytokines and cytotoxic molecules were measured using a flow cytometry based multiplex method. As shown in FIG. 3, both Th1 cytokines (IL-2, IFNγ, TNFα) and Th2 cytokines (IL-4, IL-10) were secreted by activated T cells, although IL-4 was secreted at a much lower level than other cytokines. Similarly, a significant amount of IL-6 was secreted by activated T cells. Th17 cytokine IL-17a was also secreted at high levels. Cytotoxic components sFasL, sFas, Granzyme A, Granzyme B, Perforin and Granulysin were all released in the supernatant.

HuA33-BsAb redirected T cells to specifically kill colon cancer and gastric cancer cells. The ability of huA33-BsAb to redirect T cells to kill cancer cells was tested. Based on a survey of GPA33 expression on multiple human cancer cell lines (FIG. 10), 3 colon cancer cell lines (LS174T, SW1222 and Colo205) and one gastric cancer cell line (SNU16) were selected for cytotoxicity studies. These cell lines were classified as MSI (LS174T) subtype or MSS (SW1222, Colo205, SNU16) subtype based on their microsatellite instability profile (Williams D S et al., *PLOS ONE* 5:e16012 (2011); Yoon K et al., *Genome Research* 23:1109-1117 (2013); Suter C M et al., *Br J Cancer* 88:413-419 (2003)). Moreover, LS174T cells carried a KRAS G12D mutation while the others carried p53 mutations or deletions (Ahmed D et al., *Oncogenesis* 2:e71 (2013); Liu Y & Bodmer W F, *Proceedings of the National Academy of Sciences of the United States of America* 103:976-981 (2006); Ku J-L & Park J-G: *Cancer Research and Treatment: Official Journal of Korean Cancer Association* 37:1-

19 (2005); Ikediobi O N, Davies H, Bignell G, et al., *Molecular cancer therapeutics* 5:2606-2612 (2006)).

Cancer cells were incubated with activated T cells at an effector to target ratio of 10:1 in the presence of 10-fold serial dilutions of huA33-BsAb. GPA33(−) melanoma cell line SKMEL5 and osteosarcoma cell line TC32 were used as negative controls. As shown in FIG. 4(A), huA33-BsAb redirected T cells to specifically kill all GPA33-expressing cancer cells regardless of their genetic backgrounds, while sparing SKMEL5 and TC32, confirming the antigen specificity of huA33-BsAb mediated TDCC. Maximal level of cytotoxicity seemed to correlate with the level of FACS staining (FIG. 1(D) and FIG. 4(A)). Moreover, TDCC induced by huA33-BsAb was potent, with $EC_{50}$ values in the pM range. See FIG. 4(A).

To determine which subsets of T cells were mobilized by huA33-BsAb, CD45RA(+)CD62L(+) and CD45RA(−)CD45RO(+)CD62L(−) memory subsets from both CD4(+) and CD8(+) T cells were sorted. Sorted cells were cultured in the presence of Colo205 tumors cells at an E:T ratio of 5:1 for 48 hours before measuring cytotoxicity using the LDH assay. As shown in FIG. 4(B), both CD4(+) and CD8(+) memory T cell subsets were capable of inducing cytotoxicity, with CD8(+) memory T cells mediating more efficient killing at higher concentration. CD45RA(+)CD62L(+) subsets of both CD4(+) and CD8(+) populations, with the majority being naïve T cells, were capable of inducing cytotoxicity after 48 hours, although the potency was less compared to memory T cells.

Figure 12:
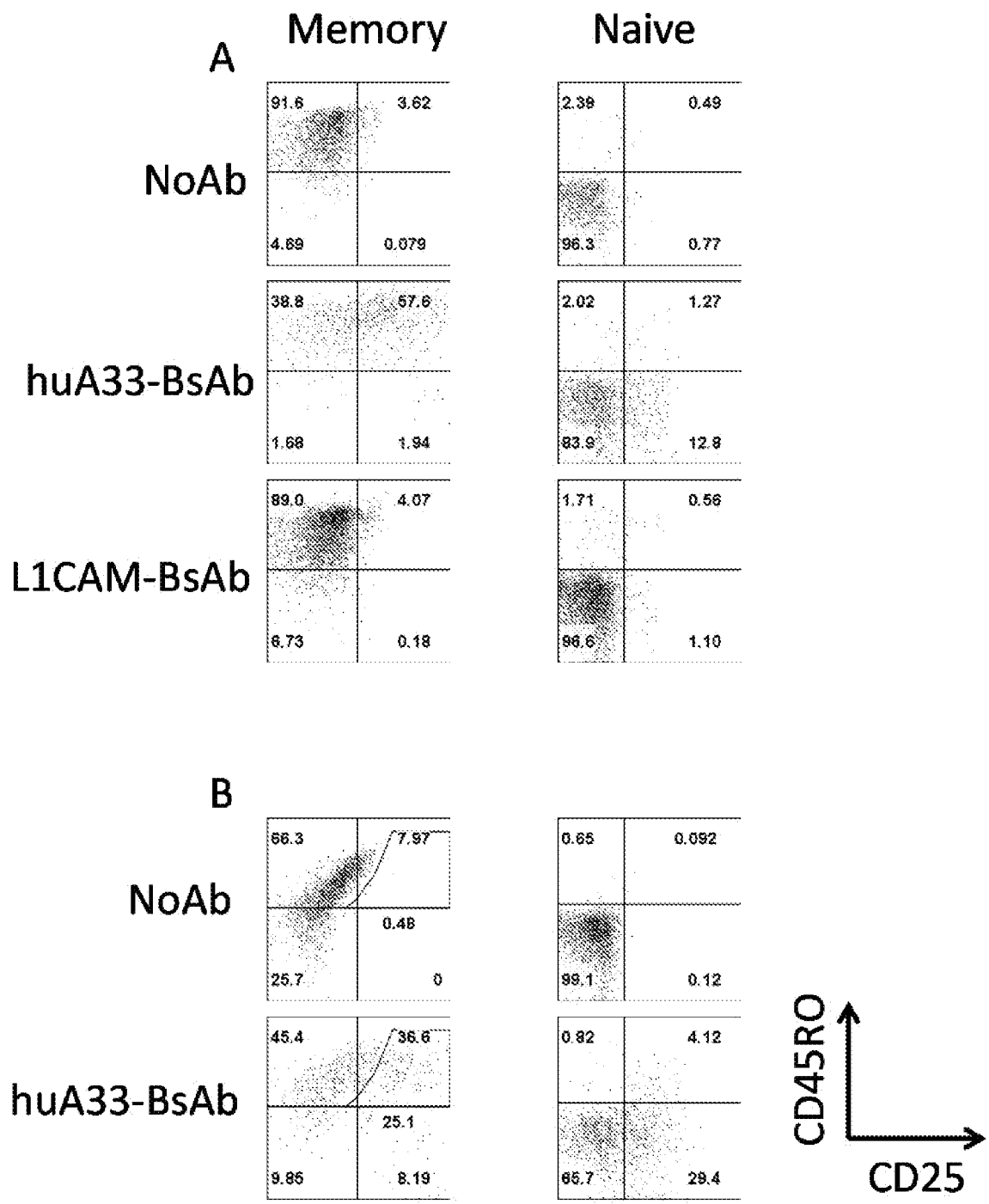
FIGS. 12(A) and 12(B) show the staining of CD45RO and CD25 markers on T cells 48 hours post incubation with Colo205 cells in the presence of different antibodies. Cells were obtained from the TDCC assay after the supernatant was used for LDH measurement.

When T cells from the TDCC assay were stained with CD45RO and CD25, it was found that CD25 expression was upregulated in the presence of huA33-BsAb, in both CD45RO+ and CD45RO− fractions (FIG. 12(A) and FIG. 12(B)), confirming that both naïve and memory T cells could be activated by huA33-BsAb. The majority of CD45RA(+)CD62L(+) T cells stayed CD45RO(−) after incubation, with a small but significant population increasing their CD45RO expression, especially among the CD8(+) cells. See FIG. 12(B). However, this population could have been derived from either the maturation of naïve T cells or from expansion of rare CD45RO+ cells present in the initial culture. Taken together, these data demonstrated that huA33-BsAb could induce potent cytotoxicity against colon and gastric cancer cells in a GPA33 dependent manner, by mobilizing both CD4 and CD8 T cells, especially those of the memory phenotype.

These results demonstrate that the antibodies of the present technology or antigen binding fragments thereof, specifically bind to A33 antigen with high binding affinity. Accordingly, the immunoglobulin-related compositions disclosed herein are useful for detecting A33 protein in a sample.

Example 5: Affinity Maturation of huA33-BsAb by Yeast Display

In an attempt to further improve the potency of huA33-BsAb, yeast display method was used to affinity mature scFv derived from huA33. Since scFv tends to aggregate easily, a method to rapidly reformat scFv to T cell engaging huA33-BsAbs (which is a more relevant format and could be readily produced in high yield and purity) was developed (FIG. 13).

The method was based on a one-step 4-fragment ligation approach that made use of the type II enzyme SapI to allow seamless linkage of different fragments and could be readily adapted to other vectors or scaled up to a high-throughput workflow. Multi-fragment In-Fusion® cloning (CLON-TECH® Laboratories, Mountain View, Calif.) was also tested with success but was less robust (data not shown), possibly due to the specific sequences of the expression vector.

Figure 5:
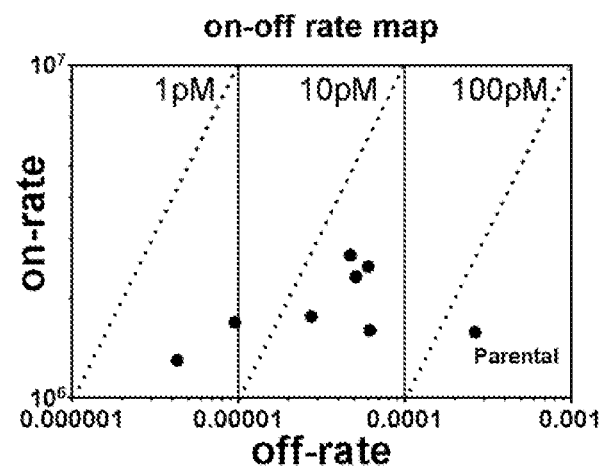
FIG. 5(A) shows a summary of the affinity maturation of huA33 (H2L2) by yeast screening.
FIG. 5(B) shows a summary of $K_D$ of parental and affinity matured huA33-BsAb (top) and the on-off rate map of different huA33-BsAbs derived from SPR analysis (bottom).
FIG. 5(C) shows the results of the T-cell dependent cytotoxicity (TDCC) assay of the parental and affinity matured huA33-BsAbs.

From sequence analysis of 60 single clones, 7 clones (FIG. 5(A)) were selected for further characterization by SPR and TDCC assay. All 7 clones showed increased binding affinity as compared to the parental antibody, ranging from 4.3 to 51-fold (FIG. 5(B)). The amino acid sequences of the heavy chain and light chain of the seven affinity-matured clones are shown in FIGS. 30-36. Majority of improvement was attributable to the slower off-rate. All clones showed slight improvement in maximal killing in TDCC assays (FIG. 5(C)).

These results demonstrate that the antibodies of the present technology or antigen binding fragments thereof, specifically bind to A33 antigen with high binding affinity. Accordingly, the immunoglobulin-related compositions disclosed herein are useful for detecting A33 protein in a sample.

Example 6: In Vivo Therapy Studies Using huA33-BsAb

Efficacy of huA33-BsAb was tested in vivo in the following xenograft models in humanized DKO mice using two different tumor models: (1) s.c. tumor plus s.c. effectors and (2) i.p. tumor plus i.v. effectors.

HuA33-BsAb cured MSI tumor LSI74T in a s.c. xenograft model and suppressed tumor growth in an i.p. model. LS174T cells were mixed with PBMCs at a 1:1 ratio and implanted subcutaneously in DKO mice. As shown in FIG. 6(A), without antibody treatment, both tumor only and tumor+PBMC groups exhibited rapid tumor growth. Mice from tumor+PBMC group developed tumor ulceration and had to be euthanized. In contrast, 6 doses of huA33-BsAb over 3 weeks effectively cured the mice, which remained tumor free for at least 120 days.

To simulate malignant ascites, a common occurrence in colon cancers, luciferase-expressing LS174T cells were planted intraperitoneally into DKO mice. When tumor growth was confirmed by luminescence, mice were randomized into different treatment groups, treated with no antibody group (tumor only), tumor+T cell only group (tumor+ATC), or i.v. huA33-BsAb (7 doses over 3 weeks), plus weekly T cell injections over 3 weeks. Treatment was started on day 5 after tumor implantation. All T cells were injected through retro-orbital route.

As shown in FIG. 6(B) and FIG. 6(C), all control groups (no antibody group, or tumor+T cell only group) showed exponential growth of tumor in the abdomen. By day 28, 3 out of 4 mice in the no antibody group, and 3 out of 5 mice from tumor+T cell group, respectively, succumbed to tumors. In contrast, huA33-BsAb significantly suppressed metastatic growth of LS174T tumor in the abdominal areas of treated mice. All mice remained alive until at least 60 days without further treatment. These results demonstrate that huA33-BsAb was effective against CRC tumors with an MSI genotype. However, as mentioned before, MSI tumors account for only a minority of CRC cancer patients. Majority of CRC patients are MSS. Therefore, efficacy of huA33-BsAb was tested further using MSS tumors.

HuA33-BsAb cured MSS tumor COLO205 in a s.c. xenograft model and suppressed tumor growth of metastatic MSS tumor SW1222. Two MSS colon cancer cell lines Colo205 and SW1222 were tested. For Colo205 cells, tumors were implanted subcutaneously with PBMCs as effector cells. In this model, 4 doses of huA33-BsAb were enough to completely eradicate Colo205 tumors and the mice remained tumor free for at least 4 months after a total of 6 doses of antibody treatment (FIG. 7(A) and FIG. 7(B)).

Figure 7:
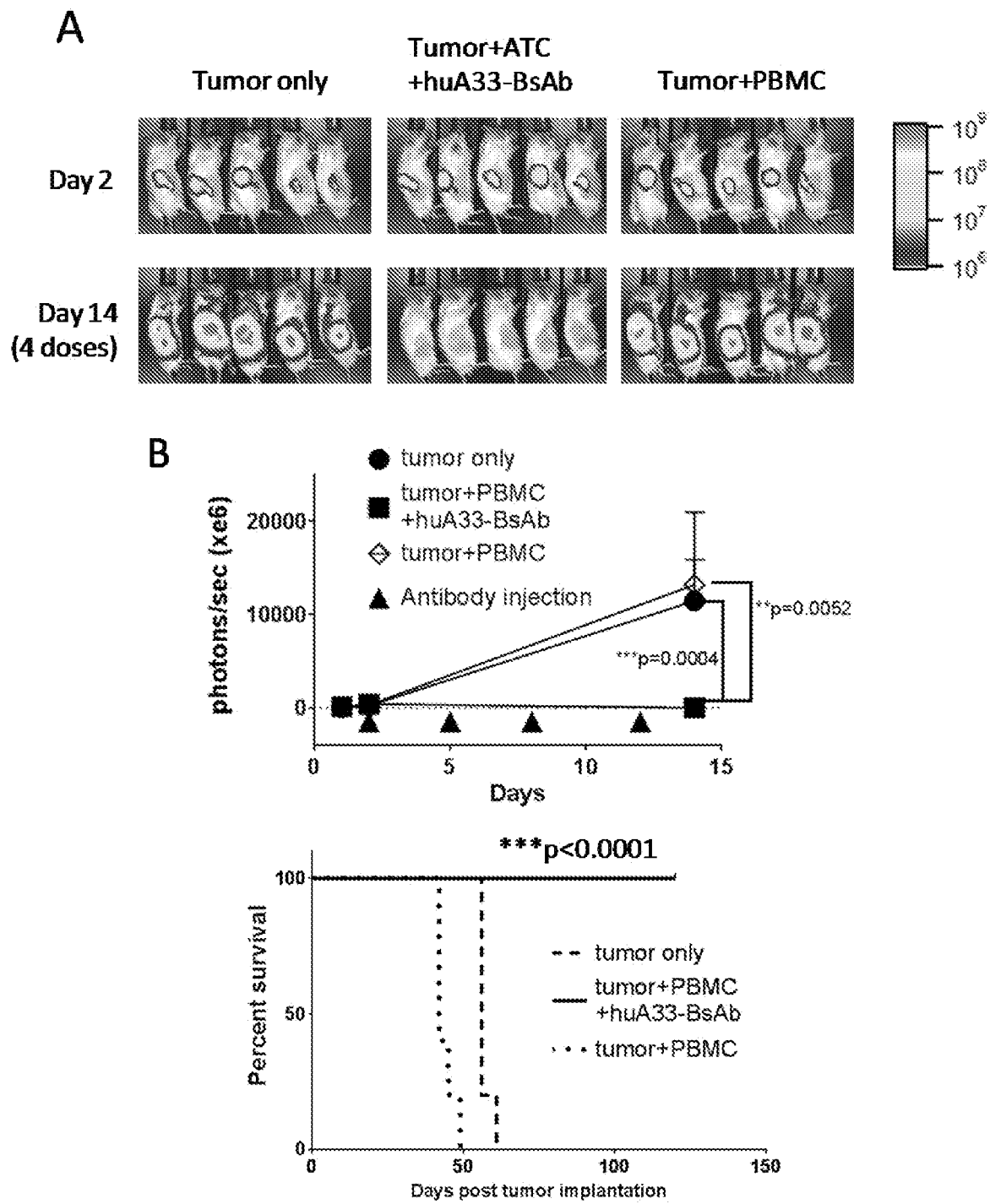
FIG. 7(A) shows luminescence images showing growth of s.c. Colo205 tumors in different groups.
FIG. 7(B) shows the quantification of signals from FIG. 7(A) (top) and the survival of mice from different groups in FIG. 7(A) (bottom).
FIG. 7(C) shows luminescence images of i.p. SW1222 tumor; mouse #1 from tumor only group and mouse #3 from tumor+ATC group which did not take tumor after 21 days were excluded from imaging at later time points and were not included in survival analysis in FIG. 7(D).
FIG. 7(D) shows the survival of mice with i.p. SW1222 tumor.

For the SW1222 cell line, tumors were planted intraperitoneally and treated with 6 doses of i.v. antibody over 3 weeks, and i.v. T cell weekly over 2 weeks. As shown in FIG. 7(C) and FIG. 7(D), the two control groups had tumor growth spread throughout the whole abdominal area, whereas treatment with huA33-BsAb suppressed tumor growth and significantly prolonged mice survival (p=0.0125). These results demonstrate that the efficacy of huA33-BsAb in treating MSS tumors was comparable to that observed when treating MSI tumors. It is anticipated that additional treatment cycles will completely eradicate the growth of tumors, as in subcutaneous models.

HuA33-BsAb inhibited growth of gastric cancers in a s.c. xenograft model. GPA33 is expressed in a subset of gastric cancer cells. FACS analysis and in vitro TDCC assays demonstrated that SNU16 expressed GPA33 and was sensitive to huA33-BsAb redirected T cell killing. SNU16 cells were xenografted subcutaneously after mixing with human PBMCs. huA33-BsAb effectively cured the mice harboring s.c. tumors (FIG. 8(A)) and significantly prolonged survival. Unlike NSG mice, DKO mice were more resistant to engraftment of human PBMCs. In s.c. SNU16 model on day 58 (FIG. 8(B)), most mice showed low levels of blood chimerism with large variation.

As demonstrated above, the efficacy of huA33-BsAb was independent of the genetic background or mutational status of the CRC tumors, which is a critical biological property if applicability to the majority of CRC is desired. Unlike CAR modified T cells, the huA33-BsAb-redirected T cells did not undergo cellular exhaustion and exhibited continual quantitative tumor-homing properties >3 weeks. Tumors were cured despite the presence of PD1 and PD-L1, and the addition of checkpoint blockade at subtherapeutic doses of huA33-BsAb further enhanced these anti-tumor properties. The A33 immunoglobulin-related compositions disclosed herein offer both FcR-dependent and T cell-dependent immunotherapeutic strategies for the diagnosis and therapy of A33 associated cancers.

Taken together, these results demonstrate that the antibodies or antigen binding fragments of the present technology can detect tumors and inhibit the progression of tumor growth and/or metastasis. Accordingly, the immunoglobulin-related compositions disclosed herein are useful for detecting and treating an A33-positive cancer in a subject in need thereof.

Example 7: Use of huA33-C825 Antibodies of the Present Technology in Pretargeted Radioimmunotherapy Major drawbacks in the development of antibody agents for pretargeted radioimmunotherapy (PRIT) are radiation overexposure in normal tissues, immunogenicity, suboptimal tumor dose and a low therapeutic index. This Example will demonstrate that the huA33-DOTA bispecific antibodies of the present technology are useful in PRIT for treating cancers expressing the human A33 antigen such as colorectal cancer.

The A33-DOTA bispecific antibodies of the present technology comprise a first antigen-binding site based on the humanized A33 antibodies described herein and a second antigen-binding site that binds to a small molecule hapten (e.g., benzyl-1,4,7,10-tetraazacyclododecane-1,4,7,10-tetraacetic acid [DOTA-Bn]). An anti-DOTA-Bn single chain Fv fragment (ScFv) based on an affinity matured 2D 12.5 antibody will be linked to the carboxyl end of a humanized A33 light chain. FIG. 37 shows the amino acid and cDNA sequences of the heavy chain of bispecific antibodies huA33-huC825 (H2L2), which correspond to SEQ ID NO: 58 and SEQ ID NO: 59, respectively. FIG. 38 shows the amino acid and cDNA sequences of the light chain of bispecific antibodies huA33-huC825 (H2L2), which correspond to SEQ ID NO: 60 and SEQ ID NO: 61, respectively. FIG. 39 shows the amino acid sequence of the heavy chain and light chain of the bispecific antibodies huA33-mC825 (H2L2), which correspond to SEQ ID NO: 62 and SEQ ID NO: 63, respectively.

Tumor cell lines and cell culture reagents. The human colorectal cancer cell line SW1222 will be maintained by serial passage. The cells are cultured in Minimal Essential Medium supplemented with 10% heat inactivated fetal calf serum, 2.0 mM glutamine, 100 units/mL penicillin, and 100 units/mL streptomycin in a 37° C. environment containing 5% $CO_2$. Cultures are established and cryopreserved in small aliquots to limit passages to less than three months, and periodically tested for *Mycoplasma* according to manufacturer's specifications using a commercial kit (Lonza, Portsmouth, N.H.). For trypsinization during passage and harvesting of cells, a solution of 0.25% trypsin/0.53 mM EDTA in Hanks Buffered Salt Solution without calcium and magnesium is used. huA33-huC825 and huA33-mC825 will be produced in CHO cells in a mammalian expression vector and purified by protein A affinity chromatography.

Surface plasmon resonance studies. BIACORE® T100 Biosensor, CM5 sensor chip, and related reagents are purchased from GE Healthcare (Chicago, Ill.). Recombinant human A33 protein will be purchased from Novoprotein Scientific, Inc. (Summit, N.J.). A BSA-(Y)-DOTA-Bn conjugate will be prepared as described in Cheal et al, *Mol. Cancer Ther.* 13(7) (2014). A33 and DOTA antigens are immobilized using the Amine Coupling kit (GE Healthcare, Chicago, Ill.). Purified bispecific antibodies and control antibodies are analyzed, and data will be fit to a bivalent analyte model using the BIACORE® T100 evaluation software as described in Cheal et al, (2014).

PRIT reagents, protocol and xenograft studies. All animal experiments will be approved by the Institutional Animal Care and Use Committee of Memorial Sloan Kettering Cancer Center and institutional guidelines for the proper and humane use of animals in research will be followed. Athymic nu/nu female mice (6-8 weeks old; Harlan Sprague Dawley) are allowed to acclimate in the vivarium for at least one week. Groups of animals are injected s.c. with A33-positive SW1222 in the left flank with $5 \times 10^6$ tumor cells formulated with MATRIGEL® (BD Biosciences, San Jose, Calif.) in a 1:1 ratio, and established tumors (100-900 $mm^2$) will be observed in 7-10 days using the formula for the volume of an ellipsoid (V=4/3π(length/2×width/2×height/2). All reagents will be given intravenously (i.v.) via the lateral tail vein. PRIT protocol includes injections of: huA33-huC825 or huA33-mC825 [t=−28 h], followed by clearing agent (a 500 KDa dextran-(Y)-DOTA-Bn conjugate, prepared according to Orcutt et al., *Nucl. Med Biol.* 38:223-233 (2011) and formulated in saline for injection 24 h later. The substitution ratio of moles of (Y)-DOTA-Bn per moles of dextran will be 61(Y)-DOTA-Bn/dextran)) [t=−4 h], and $^{177}$Lu-DOTA-Bn (prepared as previously described by incubating aminobenzyl-DOTA(p-$NH_2$-Bn-DOTA) from MACROCYCLICS™ and $^{177}LuCl_3$ (specific activity ~30 Ci/mg; PERKINELMER®, Inc.) and formulated in saline for injection) after 4 h [t=0 h]. In addition, huA33-C825 is trace radiolabeled with $I^{131}$ to estimate tumor uptake during PRIT.

The IODOGEN method (Cheal, S. et al., *Mol. Cancer Ther.* 13(7): 1-10 (2014)) is used to prepare $^{131}$I-huA33-mC825 or $^{131}$I-huA33-huC825 (final specific activity 95.5 MBq/mg, with cold huA33-huC825 or huA33-mC825 added to achieve desired mg dose, radiochemical purity >98% using size-exclusion high pressure liquid chromatography), and the in vitro cell binding immunoreactivity will be evaluated using SW1222 cells essentially as described by Lindmo, T. et al., *J. Immunol. Meth.* 126(2): 183-189 (1990)). For PRIT with non-specific IgG-C825, an equivalent mg dose of a GD2-targeted bispecific antibody (hu3F8-C825) is used in place of huA33-mC825 or huA33-huC825.

For ex vivo biodistribution analysis, mice are euthanized by C02 (g) asphyxiation, and tumor and selected organs are harvested, rinsed with water and allowed to air-dry, weighed and radioassayed by gamma scintillation counting (PERKINELMER® Wallac Wizard 3", PERKINELMER®-Inc., Waltham, Mass.). Count rates will be background and decay corrected, converted to activities using a system calibration factor, normalized to the administered activity, and expressed as percent injected dose per gram (% ID/g). Differences in $^{177}$Lu-activity concentration in tumor and various tissues will be analyzed by Student's unpaired t-test when appropriate.

Estimation of absorbed doses. Groups of A33-positive SW1222 tumor-bearing mice (n=4-5) are given 0.25 mg of huA33-C825 (either huA33-huC825 or huA33-mC825), Clearing Agent (62.5 µg; 25% (w/w)), and 1.85-2.0 MBq (~10 pmol) of $^{177}$Lu-DOTA-Bn, and are sacrificed at 2, 24, and 120 h p.i. For each tissue, the non-decay-corrected time-activity concentration data are fit using Excel to a 1-component, a 2-component, or a more complex exponential function as appropriate, and will be analytically integrated to yield the cumulated activity concentration per unit administered activity (MBq-h/g per MBq). The $^{177}$Lu equilibrium dose constant for non-penetrating radiations (8.49 g-cGy/MBq-h) will be used to estimate the tumor-to-tumor and select organ-to-organ self-absorbed doses, assuming complete local absorption of the $^{177}$Lu beta rays only and ignoring the gamma ray and non-self dose contributions. To determine the effect of the $^{177}$Lu-DOTA-Bn dose on the relative uptake of $^{177}$Lu-DOTA-Bn in tumor and select tissues with the highest absorbed doses (i.e., blood, liver, spleen, and kidneys), groups of SW1222 tumor-bearing female athymic nude mice (n=5/group) will be given 0.25 mg (1.19 nmol) of huA33-C825 (either huA33-huC825 or huA33-mC825) at t=−28 h and 62.5 µg of Clearing Agent at t=−4 h, followed with either 11.1 MBq (11.14-11.40 MBq), 55.5 MBq (54.61-55.06 MBq), or 111 MBq (109.52-112.5 MBq). All groups are sacrificed at 24 h p.i. of $^{177}$Lu-DOTA-Bn (i.e., time of maximum tumor uptake) for biodistribution analysis of $^{177}$Lu-activity.

PET imaging of PRIT+$^{86}$Y-DOTA-Bn. A single group of mice bearing A33-positive SW1222 tumors in the shoulder (n=5) are given 0.25 mg of huA33-C825 (huA33-huC825 or huA33-mC825), Clearing Agent (62.5µ 25% (w/w)), and 8.6-8.8 MBq (~50 pmol) of $^{86}$Y-DOTA-Bn, and are non-invasively imaged using a microPET Focus 120 (CTI Molecular Imaging, Inc. Knoxville, Tenn.) at approximately 2 and 20 h p.i. The following imaging acquisition parameters will be used: energy window of 350-750 keV, coincidence timing window of 6 nsec, and an acquisition time of 20 min. The resulting list-mode data are sorted into 2D histograms by Fourier re-binning and transverse images reconstructed by filtered back-projection into a 128×128×95 matrix (reconstructed spatial resolution is 2.6 mm full-width half maximum (FWHM)). The image data are corrected for non-uniformity of response of the scanner, deadtime count losses, physical decay (to the time of injection), and the $^{86}$Y positron branching ratio. No attenuation, scatter, or partial-volume averaging correction will be applied. An empirically determined system calibration factor (i.e. pCi/mL/cps/voxel) for mice is used to convert voxel count rates to activity concentrations. The resulting image data are then normalized to the administered activity to determine by region-of-interest analysis the percent of the injected dose per gram (% ID/g) of tissue corrected for radioactive decay to the time of injection. AsiPRO VM 5.0 software (Concorde Microsystems, Knoxville, Tenn.) is used to perform imaging and region of interest (ROI) analyses (as ROI maximum, % ID/g). The animals are sacrificed at 24 h p.i. for ex vivo biodistribution analysis.

Autoradiography and immunohistochemistry. Frozen and OCT-embedded tumor and kidney from select mice administered huA33-C825 (huA33-huC825 or huA33-mC825) PRIT followed with either 11.1 (11.14-11.40 MBq), 55.5 (54.61-55.06 MBq), or 111 MBq (109.52-112.5 MBq) of $^{177}$Lu-DOTA-Bn (time of sacrifice: 24 hours p.i.) are cut into 10 m sections using a cryostat (Avantik, Springfield, N.J.), and are immediately exposed to an imaging plate (Fuji Photo Film, Kanagawa, Japan) for 72 h and subsequently scanned using TYPHOON™ FLA 7000 scanner (GE, Pittsburgh, Pa.). The same sections will be subjected to hematoxylin and eosin staining and will be scanned under Olympus BX60 microscope equipped with controlled moving stage (Olympus, Central Valley, Pa.). Both autoradiogram and microscope images are processed and analyzed using ImageJ (NIH, Bethesda, Md.).

Therapy and scintigraphy studies. Groups of mice bearing established s.c. A33-positive SW1222 xenografts are injected with either huA33-C825 (huA33-huC825 or huA33-mC825) or non-specific (n.s.) IgG-C825 PRIT (i.e., single-cycle treatment, $^{177}$Lu-DOTA-Bn injection on day 7 post tumor-inoculation) or two cycles of PRIT (i.e., dual-cycle treatment study, $^{177}$Lu-DOTA-Bn injections given on day 10 and day 17 post tumor-inoculation). For the dual-cycle treatment study, the tumor volume on day 10-post tumor inoculation (TV 10) is described (i.e., day of first $^{177}$Lu-DOTA-Bn injection) and expressed when appropriate as average±SD. The following definitions are used to describe treatment response: a complete response (CR) is defined as tumor shrinkage to <100 mm$^3$. A durable response (DR) is defined as survival at 140 days post treatment. Excessive tumor burden is defined as >2000 mm$^3$. For scintigraphy studies, select groups of A33-positive SW1222 tumor-bearing mice undergoing treatment are placed under anesthesia by gas inhalation before scanning in a nano-SPECT (Bioscan, Washington D.C.) at 20 hours p.i. for 30 minutes (~10$^5$ counts per image) using a low-energy high-resolution collimator and a window set at 208 keV. Images are reconstructed to a 256×256 matrix using Bioscan HiS-PECT software and are uploaded into ASIPro VM for analysis.

Results. A dose of huA33-C825 (huA33-huC825 or huA33-mC825) is selected based on pilot biodistribution studies in SW1222-tumor bearing mice at 24 h p.i. of $^{177}$Lu-DOTA-Bn using 0.1-0.6 mg of huA33-C825 (0.48-2.86 nmol), and fixed ratios of Clearing Agent and $^{177}$Lu-DOTA-Bn (5.6 MBq). Next, additional biodistribution experiments are performed to optimize the Clearing Agent dose during PRIT. Groups of tumor-bearing mice (n=3 to 4 per group) are injected with huA33-C825 (huA33-huC825 or huA33-mC825), followed 24 h later with either: saline (i.e., vehicle), 2.4% (w/w, with respect to a preselected huA33-C825 dose), 5% (w/w), 10% (w/w), or 25% (w/w) Clearing Agent doses (0-62.5 µg/mouse). After an additional 4 h, mice are injected with 5.6 MBq of $^{177}$Lu-DOTA-Bn, and sacrificed 24 h later for biodistribution analysis. It is expected that the Clearing Agent dose will have a significant impact on the circulating (i.e., blood) $^{177}$Lu-activity and may reduce the capacity for subsequent $^{177}$Lu-DOTA-Bn uptake at the tumor.

Next, $^{177}$Lu-DOTA-Bn dose titration studies are performed using the optimized PRIT doses for huA33-C825 (huA33-huC825 or huA33-mC825) and Clearing Agent. For Lu-DOTA-Bn dose titration studies, the $^{177}$Lu-activity biodistribution data for tumor and critical select tissues (blood, liver, spleen, and kidneys) is compared between $^{177}$Lu-DOTA-Bn dose groups as both % ID/g and absolute uptake (kBq/g). Finally, a single-time point biodistribution experiment at 24 h p.i. of $^{131}$I-trace labeled huA33-C825 (0.39-0.40 MBq with cold huA33-C825 added to 1.19 nmol) is performed in SW1222-tumor bearing mice to estimate the absolute antibody uptake of huA33-C825 (huA33-huC825 or huA33-mC825) in tumor (as pmol/g) during PRIT.

Biodistribution of radiolabeled DOTA-Bn and estimates of absorbed doses in mice implanted with SW1222 tumor cells are determined. PRIT is carried out in groups of A33-positive SW1222 tumor-bearing mice with the optimum doses of huA33-C825 and Clearing Agent, followed with 2.0 MBq (~10 pmol) of $^{177}$Lu-DOTA-Bn and biodistribution studies are carried out from 2-120 h p.i. of $^{177}$Lu-DOTA-Bn to determine the $^{177}$Lu-activity residence time in tumor and various normal tissues. Briefly, $^{177}$Lu-activity in tumor and various normal tissues are determined using a biodistribution assay following PRIT with optimum A33-C825 (huA33-huC825 or huA33-mC825) and dextran-clearing agent doses and 2.0 MBq (~10 pmol) of $^{177}$Lu-DOTA-Bn. Groups of SW1222 tumor-bearing mice (n=4 to 5) are given huA33-C825, followed 24 h later with dextran-clearing agent, and after an additional 4 h, 2.0 MBq (~10 pmol) of $^{177}$Lu-DOTA-Bn. A single group of animals is sacrificed at 2, 24, and 120 h p.i. of $^{177}$Lu-DOTA-Bn for biodistribution analysis. These data will be used as described herein to estimate absorbed doses for radioimmunotherapy with $^{177}$Lu-DOTA-Bn. It is anticipated that tumor uptake of $^{177}$Lu will occur very rapidly following administration, and will decrease over the next 96 h at 120 h p.i. For each target region, the absorbed dose is calculated as the product of the $^{177}$Lu equilibrium dose constant for non-penetrating radiations (i.e., beta rays) and the target regions $^{177}$Lu cumulated activity, assuming complete local absorption of the $^{177}$Lu beta rays and ignoring the gamma ray and non-self dose contributions. It is anticipated that a high tumor to blood therapeutic index will be observed during a single-cycle treatment, and that little to no toxicity will be observed over prolonged periods in the subjects that exhibit durable responses. Similar results in tumor uptake after PRIT are expected when assessed using PET imaging.

This Example demonstrates the efficacy of PRIT using the A33-DOTA bispecific antibodies of the present technology on A33-positive tumors. It is anticipated that a progressive increase in therapeutic index and a reduction in absolute tumor uptake will be observed with increasing doses. Accordingly, the huA33-DOTA bispecific antibodies of the present technology are useful in treating cancers expressing the human A33 antigen such as colorectal cancer.

Example 8: In Vivo Therapeutic Effects of huA33-C825 Antibodies of the Present Technology This Example illustrates the in vivo efficacy of a huA33-C825 bispecific antibody in PRIT to mediate a reduction in tumor burden in mice bearing A33-positive cancer cells. In particular, this Example describes effect of single- and dual-cycle therapy on tumor burden in SW1222-tumor bearing mice.

During the single-cycle therapy study, 5 groups of tumor-bearing mice (n=6 to 8 per group) are treated with either: vehicle (i.e., untreated, n=8, TV$_7$: 76±15 mm$^3$), 33.3 MBq $^{177}$Lu-DOTA-Bn alone (vehicle given during bispecific antibody and Clearing Agent injections, n=6, TV 7: 116±23 mm$^3$), single-cycle IgG-C825 PRIT+33.3 MBq $^{177}$Lu-DOTA-Bn (n.s. IgG-C825 given in place of huA33-C825, n=8, TV$_7$: 100±10 mm$^3$), or single-cycle huA33-C825 (huA33-huC825 or huA33-mC825) PRIT+either 11.1 MBq or 33.3 MBq $^{177}$Lu-DOTA-Bn (both n=8, TV$_7$: 103±17 mm$^3$ and TV$_7$: 93±15 mm$^3$, respectively). It is expected that the relative tumor uptake will decrease as the $^{177}$Lu-DOTA-Bn dose increases during treatment. It is anticipated that the groups of tumor-bearing mice receiving either no treatment, treatment consisting of either 33.3 MBq $^{177}$Lu-DOTA-Bn alone, or single-cycle IgG-C825 PRIT+33.3 MBq $^{177}$Lu-DOTA-Bn will show no tumor responses. Scintigraphy of the two latter groups given $^{177}$Lu-DOTA-Bn is expected to show minimal activity in the tumor region. In contrast, groups treated with single-cycle huA33-C825 PRIT (huA33-huC825 or huA33-mC825)+either 11.1 MBq or 33.3 MBq $^{177}$Lu-DOTA-Bn are expected to show a delay in tumor growth following treatment.

In a second therapy study, dual-cycle huA33-C825 PRIT (huA33-huC825 or huA33-mC825) treatment is investigated. When mice are given either no treatment (n=5/TV$_{10}$: 314±77 mm$^3$), all mice will be sacrificed within 30 days due to excessive tumor burden. It is anticipated that treatment with two cycles of PRIT+11.1 MBq $^{177}$Lu-DOTA-Bn (total $^{177}$Lu-DOTA-Bn dose 22.2 MBq) (n=5/TV$_{10}$: 462±179 mm$^3$) will lead to a complete tumor response and/or delay tumor growth in the treated subjects.

Toxicity studies. Briefly, a total of six mice treated with either two cycles of PRIT+11.1 MBq of $^{177}$Lu-DOTA-Bn (n=3) or two cycles of PRIT+1.5 mCi of $^{177}$Lu-DOTA-Bn (n=3) are submitted for anatomic pathology assessment of kidney, bone marrow, liver, and spleen up to 9 weeks following treatment. It is anticipated that the kidney, bone marrow, liver, and spleen will be normal in the treated animals, and that the PRIT treatment will not be associated with radiation-induced toxicity.

Curative theranostic PRIT. Nude mice bearing established SW1222 s.c. xenografts (n=20; tumor volume=102±40 mm$^3$; average±standard deviation (SD)) will undergo treatment (n=5-10/group) with either: no treatment (n=5), $^{177}$Lu-DOTA-Bn only (n=5), or a three-cycle PRIT regimen consisting of huA33-C825 PRIT (huA33-huC825 or huA33-mC825)+55 MBq of $^{177}$Lu-DOTA-Bn (n=10; total: 165 MBq). Serial nanoSPECT/CT imaging is conducted on five randomly selected mice undergoing DPRIT up to 160 hours post-injection of the first cycle of $^{177}$Lu-DOTA-Bn for dosimetry calculations. It is anticipated that DPRIT will induce complete tumor response in all treated animals and no obvious toxicities in kidney, liver, spleen, and bone/marrow. Lutetium-177 nanoSPECT/CT imaging of three-cycle PRIT regimen treated animals are expected to show high contrast with visible uptake in tumors and minimal tissue background. These results demonstrate that the huA33-DOTA bispecific antibodies of the present technology are useful in reducing tumor burden in vivo and that a PRIT-based theranostic may have curative effects and/or be useful in detecting tumors in a subject.

Theranostic "real-time" simultaneous treatment and image-guided dosimetry. NanoSPECT/CT is utilized for high-resolution quantitative imaging of mice undergoing $^{177}$Lu-DPRIT treatment for "real-time" dosimetry. A SW1222-tumor bearing nude mouse (volume: 100 mm$^3$ according to Vernier caliper measurement) is treated with a single cycle of huA33-C825 PRIT (huA33-huC825 or huA33-mC825)+55 MBq of $^{177}$Lu-DOTA-Bn and is imaged by nanoSPECT/CT at three times following injection of $^{177}$Lu-DOTA-Bn: at 1, 24, and 160 hours post-injection. The images are decay corrected to the time of injection and calibrated using known activity standards. The activity concentration in tumor is determined using region-of-interest analysis of the calibrated images.

Accordingly, the huA33-DOTA bispecific antibodies of the present technology are useful in treating A33-positive cancers and are useful in detecting tumors in a subject.

Example 9: Ex Vivo Biodistribution Studies with the huA33-DOTA Bispecific Antibodies of the Present Technology The GPA33(+) human colorectal cancer cell line SW1222 was obtained from the Ludwig Institute for Cancer Immunotherapy (New York, N.Y.). SW1222 cells were cultured in Minimal Essential Medium supplemented with 10% heat-inactivated fetal calf serum, 2.0 mM glutamine, 100 units/mL penicillin, and 100 µg/mL streptomycin. All cells were maintained in a 37° C. environment containing 5% $CO_2$ (g). Upon receipt of the cell line, cultures were established and cryopreserved in small aliquots to limit passages to less than three months, and were periodically tested for *Mycoplasma* negativity using a commercial kit (Lonza, Basel, Switzerland). A solution of 0.25% trypsin/0.53 mM EDTA in Hanks Buffered Salt Solution without calcium and magnesium was used for trypsinization during cell passaging and harvesting. For establishment of SW1222 tumors, groups of mice were inoculated with 5.0×10$^6$ cells in a 200 µL cell suspension of a 1:1 mixture of media with reconstituted basement membrane (BD MATRIGEL®, Collaborative Biomedical Products Inc., Bedford, Mass.) on lower flank via subcutaneous (s.c.) injection, and established tumors (100-300 mm$^3$) were observed within 7-10 d.

For all intravenous injections, mice were gently warmed with a heat lamp and placed on a restrainer. Mice tails were sterilized with alcohol pads, and injections were placed into the lateral tail vein.

For biodistribution analysis following radiotracer administration, mice were euthanized by $CO_2$ (g) asphyxiation, and tumor and selected organs were harvested, rinsed with water and allowed to air-dry, weighed, and radioassayed by gamma scintillation counting (Wallac Wizard 3", PERKINELMER®, Inc., Waltham, Mass.). Count rates were corrected for background and decay, converted to activities using a system calibration factor specific for the isotope, normalized to the administered activity, and expressed as average±SD % ID/g unless otherwise noted.

To determine the biodistribution of the huA33-DOTA BsAb, SW1222 tumor bearing mice (group sizes: n=2 for those given Clearing Agent (CA) step, and n=1 for saline vehicle control; tumor masses ex vivo ranged from 225-571 mg at time of biodistribution) were intravenously administered via lateral tail-vein, three separate reagents: 0.25 mg (1.19 nmol) of huA33-C825 (BC155-3 Clone 2G7) at t=−28 hours, followed by 500 kD dextran-DOTA(Y) clearing agent at t=−4 hours, and [$^{177}$Lu]Lu-DOTA-Biotin (50 µCi) at t=0 hours. Biodistribution studies were conducted at 24 hours post-injection of the [$^{177}$Lu]Lu-DOTA-Biotin tracer. 500 kD dextran-DOTA(Y) clearing agent and [$^{177}$Lu]Lu-DOTA-Biotin was prepared using methods described in Orcutt, K. D. et al., *Mol Cancer Ther* 11:1365-1372 (2012); an identical radiochemistry protocol described for [$^{177}$Lu]Lu-DOTA-benzene was used for [$^{177}$Lu]Lu-DOTA-Biotin. % ID/gm=percent injected dose per gram of tissue.

Figure 40:
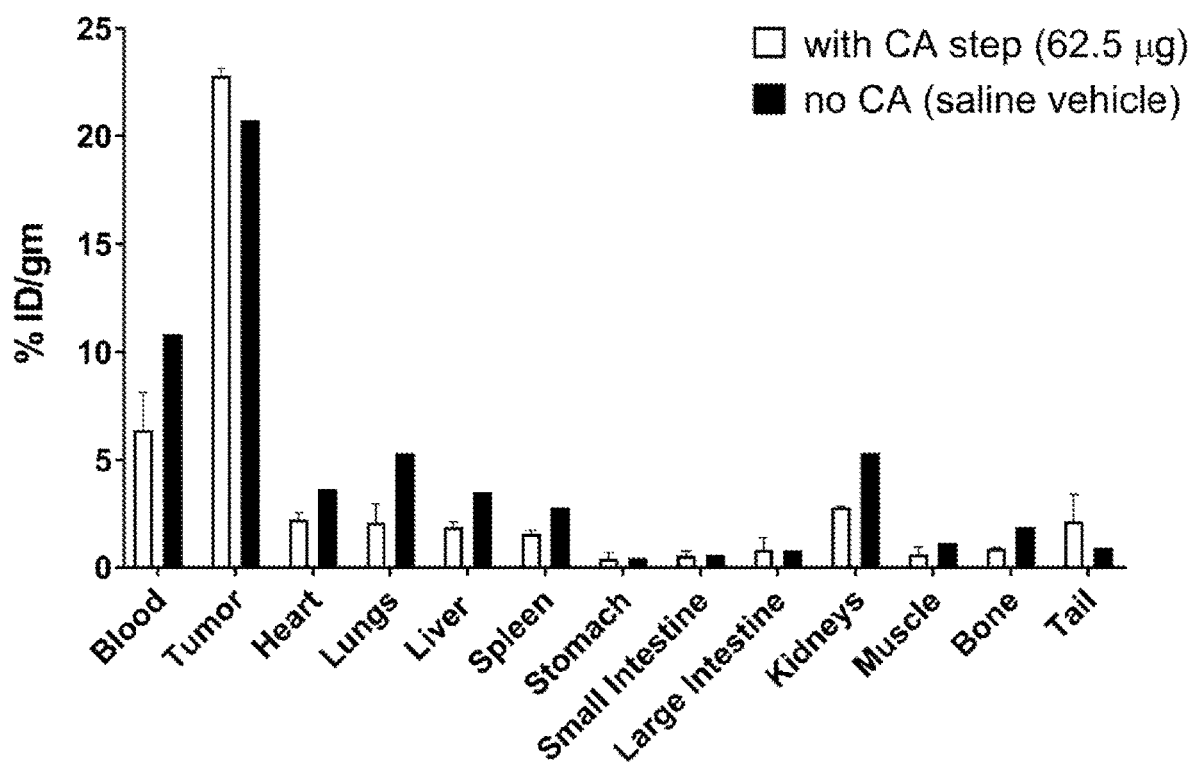
FIG. 40 shows ex vivo biodistribution results for GPA33-positive (GPA33(+)) human colorectal tumor xenograft targeting in mice bearing subcutaneous GPA33(+) SW1222 human colorectal xenografts that were treated with the rehumanized huA33-DOTA bispecific antibody disclosed herein and tracer doses of $^{177}$Lu-DOTA-biotin.

As shown in FIG. 40, animals undergoing PRIT with the huA33-DOTA bispecific antibodies of the present technology exhibited a high degree of tumor penetration with or without the clearing agent administration step (approximately 20-25% ID/g localizing to the GPA33(+) tumors), thus demonstrating that the huA33-DOTA bispecific antibodies can effectively target tumors in vivo.

Accordingly, the huA33-DOTA bispecific antibodies of the present technology are useful in treating A33-positive cancers and are useful in detecting tumors in a subject.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. An anti-A33 antibody or antigen binding fragment thereof comprising a heavy chain immunoglobulin variable domain (VH) and a light chain immunoglobulin variable domain (VL), wherein:
   (a) the $V_H$ comprises a $V_H$-CDR1 sequence of FTFSTY-DMS (SEQ ID NO: 37), a $V_H$-CDR2 sequence of TISSGGSYTYYLDSVKG (SEQ ID NO: 38), and a $V_H$-CDR3 sequence of TTVVPFAY (SEQ ID NO: 39); and
   (b) the $V_L$ comprises a $V_L$-CDR1 sequence, a $V_L$-CDR2 sequence, and a $V_L$-CDR3 sequence selected from the group consisting of:
   KASQNVRTVVA (SEQ ID NO: 40), LASNRHT (SEQ ID NO: 41), and QYWSYPLT (SEQ ID NO: 42);
   KASQNVRTVVA (SEQ ID NO: 40), LASDRHT (SEQ ID NO: 43), and QYWSYPLT (SEQ ID NO: 42);
   KASQNVRTLVA (SEQ ID NO: 44), LASNRHT (SEQ ID NO: 41), and QHWSYPLT (SEQ ID NO: 45); and
   KASQNVRTLVA (SEQ ID NO: 44), LASNRHT (SEQ ID NO: 41), and QYWSYPLT (SEQ ID NO: 42), optionally wherein
   the antibody is a monoclonal antibody, a chimeric antibody, a humanized antibody, or a bispecific antibody, or the antigen binding fragment is selected from the group consisting of Fab, F(ab')$_2$, Fab', scF$_v$, and F$_v$
   and optionally wherein the bispecific antibody binds to T cells, B-cells, myeloid cells, plasma cells, mast-cells, CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten.

2. The antibody or antigen binding fragment of claim 1, further comprising a Fc domain of an isotype selected from the group consisting of IgG1, IgG2, IgG3, IgG4, IgA1, IgA2, IgM, IgD, and IgE, optionally wherein
   IgG1 comprises one or more amino acid substitutions selected from the group consisting of N297A and K322A; or
   IgG4 comprises a S228P mutation, or
   the antibody lacks α-1,6-fucose modifications.

3. A composition comprising the antibody or antigen binding fragment of claim 1 and a pharmaceutically-acceptable carrier, wherein the antibody or antigen binding fragment is optionally conjugated to an agent selected from the group consisting of dyes, chromagens, contrast agents, drugs, metals, liposomes, nanoparticles, RNA, and DNA, or any combination thereof, optionally wherein
   the drugs comprise one or more of toxins, cytokines, enzymes, enzyme inhibitors, hormones, hormone antagonists, growth factors, and radionuclides, optionally wherein the radionuclides comprise isotopes.

4. An anti-A33 antibody or antigen binding fragment thereof comprising a heavy chain immunoglobulin variable domain (VH) amino acid sequence present in SEQ ID NO: 5, SEQ ID NO: 6, SEQ ID NO: 15, SEQ ID NO: 19, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 58, or SEQ ID NO: 62, and a light chain immunoglobulin variable domain (VL) amino acid sequence present in SEQ ID NO: 9, SEQ ID NO: 10, SEQ ID NO: 17, SEQ ID NO: 21, SEQ ID NO: 24, SEQ ID NO: 26, SEQ ID NO:

28, SEQ ID NO: 30, SEQ ID NO: 32, SEQ ID NO: 34, SEQ ID NO: 36, SEQ ID NO: 60, or SEQ ID NO: 63, optionally wherein
   the antibody is a chimeric antibody, a humanized antibody, or a bispecific antibody
   and optionally wherein the bispecific antibody binds to T cells, B-cells, myeloid cells, plasma cells, mast-cells, CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten.

5. A recombinant nucleic acid sequence encoding the antibody or antigen binding fragment of claim 4 selected from the group consisting of: SEQ ID NOs: 7, 8, 11, 12, 16, 18, 20, 22, 59 and 61.

6. A host cell or vector comprising the recombinant nucleic acid sequence of claim 5.

7. An anti-A33 antibody comprising a HC amino acid sequence and a LC amino acid sequence selected from the group consisting of:
   SEQ ID NO: 5 and SEQ ID NO: 9;
   SEQ ID NO: 5 and SEQ ID NO: 10;
   SEQ ID NO: 6 and SEQ ID NO: 9;
   SEQ ID NO: 6 and SEQ ID NO: 10;
   SEQ ID NO: 15 and SEQ ID NO: 17;
   SEQ ID NO: 19 and SEQ ID NO: 21;
   SEQ ID NO: 23 and SEQ ID NO: 24;
   SEQ ID NO: 25 and SEQ ID NO: 26;
   SEQ ID NO: 27 and SEQ ID NO: 28;
   SEQ ID NO: 29 and SEQ ID NO: 30;
   SEQ ID NO: 31 and SEQ ID NO: 32;
   SEQ ID NO: 33 and SEQ ID NO: 34;
   SEQ ID NO: 35 and SEQ ID NO: 36;
   SEQ ID NO: 58 and SEQ ID NO: 60; and
   SEQ ID NO: 62 and SEQ ID NO: 63, respectively, optionally wherein the antibody is a chimeric antibody, a humanized antibody, or a bispecific antibody, and optionally wherein the bispecific antibody binds to T cells, B-cells, myeloid cells, plasma cells, mast-cells, CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten.

8. The antibody of claim 7, wherein the antibody comprises an IgG1 constant region comprising one or more amino acid substitutions selected from the group consisting of N297A and K322A, or wherein the antibody comprises an IgG4 constant region comprising a S228P mutation or wherein the antibody lacks α-1,6-fucose modifications.

9. The bispecific anti-A33 antibody of claim 7, wherein the bispecific antibody binds to a radiolabeled DOTA hapten.

10. A composition comprising the antibody of claim 7 and a pharmaceutically-acceptable carrier, wherein the antibody is optionally conjugated to an agent selected from the group consisting of dyes, chromagens, contrast agents, drugs, metals, liposomes, nanoparticles, RNA, and DNA, or any combination thereof, optionally wherein
   the drugs comprise one or more of toxins, cytokines, enzymes, enzyme inhibitors, hormones, hormone antagonists, growth factors, and radionuclides, optionally wherein the radionuclides comprise isotopes.

11. A method for treating an A33 expressing cancer in a subject in need thereof, comprising administering to the subject an effective amount of the antibody of claim 7, wherein the antibody specifically binds to and neutralizes A33 activity, optionally wherein the A33 expressing cancer is colorectal cancer, Pseudomyxoma peritonei, appendiceal cancer, pancreatic cancer, or gastric cancer.

12. The method of 11, wherein the antibody is administered to the subject separately, sequentially or simultaneously with an additional therapeutic agent.

13. The method of claim 12, wherein the additional therapeutic agent is one or more of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, and bisphosphonate therapy agents.

14. The method of claim 11, wherein the A33 expressing cancer is colorectal cancer with a MSI genotype or a MSS genotype, or wherein the colorectal cancer is associated with a KRAS G12D mutation or a p53 mutation.

15. A method for detecting a tumor in a subject in vivo comprising
   (a) administering to the subject an effective amount of an antibody of claim 9, wherein the antibody is labeled with a radioisotope; and
   (b) detecting the presence of a tumor expressing A33 in the subject by detecting radioactive levels emitted by the antibody that are higher than a reference value, optionally wherein
   the radioactive levels emitted by the antibody are detected using positron emission tomography or single photon emission computed tomography, or
   the subject is diagnosed with or is suspected of having cancer.

16. The method of claim 15, further comprising administering to the subject an effective amount of an immunoconjugate comprising the antibody of claim 9 conjugated to a radionuclide.

17. The method of claim 16, wherein the radionuclide is an alpha particle-emitting isotope, a beta particle-emitting isotope, an Auger-emitter, or any combination thereof, optionally wherein the beta particle-emitting isotope is selected from the group consisting of $^{86}$Y, $^{90}$Y, $^{89}$Sr, $^{165}$Dy, $^{186}$Re, $^{88}$Re, $^{177}$Lu, and $^{67}$Cu.

18. A method for detecting solid tumors in a subject in need thereof comprising
   (a) administering to the subject an effective amount of a complex comprising a radiolabeled DOTA hapten and the bispecific antibody of claim 9; and
   (b) detecting the presence of solid tumors expressing A33 in the subject by detecting radioactive levels emitted by the complex that are higher than a reference value.

19. A method for selecting a subject for pretargeted radioimmunotherapy comprising
   (a) administering to the subject an effective amount of a complex comprising a radiolabeled DOTA hapten and the bispecific antibody of claim 9;
   (b) detecting the presence of solid tumors expressing A33 in the subject by detecting radioactive levels emitted by the complex; and
   (c) selecting the subject for pretargeted radioimmunotherapy when the radioactive levels emitted by the complex are higher than a reference value.

20. A method for treating A33 expressing cancer in a subject in need thereof or increasing tumor sensitivity to radiation therapy in a subject with A33 expressing cancer comprising administering to the subject an effective amount of a complex comprising a radiolabeled DOTA hapten and the bispecific antibody of claim 9.

21. A method for treating A33 expressing cancer in a subject in need thereof or increasing tumor sensitivity to radiation therapy in a subject with A33 expressing cancer comprising
   (a) administering an effective amount of the bispecific antibody of claim 9; and
   (b) administering an effective amount of the radiolabeled-DOTA hapten to the subject.

* * * * *